United States Patent
Yoo et al.

(10) Patent No.: US 9,079,867 B2
(45) Date of Patent: Jul. 14, 2015

(54) POLYAZAMACROCYCLIC COMPOUND, AND A PRODUCTION METHOD AND A BIOMEDICAL USE THEREFOR

(75) Inventors: Jeongsoo Yoo, Daegu (KR); Darpan Navinchandra Pandya, Daegu (KR)

(73) Assignee: KYUNGPOOK NATIONAL UNIVERSITY INDUSTRY-ACADEMIC COOPERATION FOUNDATION, Buk-gu, Daegu (KR)

( * ) Notice: Subject to any disclaimer, the term of this patent is extended or adjusted under 35 U.S.C. 154(b) by 0 days.

(21) Appl. No.: 13/521,177

(22) PCT Filed: Feb. 14, 2011

(86) PCT No.: PCT/KR2011/000977
§ 371 (c)(1),
(2), (4) Date: Jul. 9, 2012

(87) PCT Pub. No.: WO2011/102626
PCT Pub. Date: Aug. 25, 2011

(65) Prior Publication Data
US 2013/0004423 A1    Jan. 3, 2013

(30) Foreign Application Priority Data

Feb. 16, 2010 (KR) .......... 10-2010-0013781
Feb. 1, 2011 (KR) .......... 10-2011-0010062

(51) Int. Cl.
| | | |
|---|---|---|
| *C07D 257/02* | (2006.01) | |
| *C07K 7/64* | (2006.01) | |
| *A61P 35/00* | (2006.01) | |
| *A61K 31/395* | (2006.01) | |
| *A61K 49/00* | (2006.01) | |
| *A61K 31/555* | (2006.01) | |
| *C07F 1/08* | (2006.01) | |
| *C07K 16/18* | (2006.01) | |
| *A61K 51/08* | (2006.01) | |
| *A61K 51/10* | (2006.01) | |

(52) U.S. Cl.
CPC ............ *C07D 257/02* (2013.01); *A61K 51/082* (2013.01); *A61K 51/088* (2013.01); *A61K 51/1051* (2013.01); *A61K 51/1093* (2013.01)

(58) Field of Classification Search
None
See application file for complete search history.

(56) References Cited

FOREIGN PATENT DOCUMENTS

| WO | WO 89/12631 | 12/1989 |
|---|---|---|
| WO | WO 2006/065266 A2 | 6/2006 |
| WO | WO 2009/143101 A2 | 11/2009 |
| WO | WO 2012/037648 A1 | 3/2012 |

OTHER PUBLICATIONS

Karfeld et al. (2007) Bioconjugate Chemistry vol. 18, No. 6, pp. 1697-1700.*
Chapman et al. J Chem Soc Dalton Trans Issue 3 pp. 345-353; publication year: 1992.*
Zimmermann et al. Nuclear Medicine and Biology vol. 30, pp. 417-427; publication year: 2003.*
Carolyn J. Anderson, et al., Radiometal-Labeled Agents (Non-Technetium) for Diagnostic Imaging, 2219-2234, Aug. 11, 1999, Chem. Rev., Web.
Maggie S. Cooper, et al., Comparison of 64Cu-Complexing Bifunctional Chelators for Radioimmunoconjugation: Labeling Efficiency, Specific Activity, and in Vitro/in Vivo Stability, 1029-1039, Apr. 4, 2012, Bioconjugate Chemistry, ACS Publications.
Dr. Mark Daniel Bartholoma, Recent Developments in the Design of Bifunctional Chelators for Metal-Based Radiopharmaceuticals used in Positron Emission Tomography, 36-51, 2012, Inorganica Chimica Acta.
Luciano Lattuada, et al., The Synthesis and Application of Polyamino Polycarboxylic Bifunctional Chelating Agents, 3019-3049, Mar. 8, 2011, Chem Soc. Rev., RSC Publishing.
Monica Shokeen, et al., Medicinal Chemistry, 2011, 7, 413-429.
Carolyn J. Anderson, et al., Exp. Opin. Ther. Patents (2000) 10(7): 1057-1069.
Boswell, et al., Bioconjugate Chem. 2008, 19,1476-1484.
Elizabeth A. Lewis, et al. Chem. Commun., 2004, 2212-2213, doi: 10.1039/b406906d.
Shuang Liu, et al., Bioconjugate Chem. 2001, 12, 7-34.
Jesse J. Parry, et al., Bioconjugate Chem. 2007, 18, 1110-1117.
Ingrid Dijkgraaf, et al., Nuclear Medicine and Biology 34 (2007) 29-35.
Lin Li, et al., Bioconjugate Chem. 2006, 17, 68-76.
Shuang Liu, Advanced Drug Delivery Reviews 60 (2008) 1347-1370.
Lindsay S. Karfield, et al., Bioconjugate Chem. 2007, vol. 18, No. 6, 1697-1700.
Jason S. Kim, et al., J. Am. Chem. Soc. 2007, vol. 129, 8962-8963.
Chuqiao Tu, et al., Chem. Commun., vol. 13, 2007, 1331-1333.
Koji Machitani, et al., Analytical Sciences Apr. 2008, vol. 24 463-469.
Shuang Liu, et al., Bioconjugate Chem. 2002, vol. 13, 902-913.
Guiyang Hao, et al., Current Radiopharmaceuticals, 2011, 4, 109-121.
Carolyn J. Anderson, et al., Cancer Biotherapy and Radiopharmaceuticals vol. 24, 2009, 379-393.

(Continued)

*Primary Examiner* — Johann R Richter
*Assistant Examiner* — Katherine Peebles
(74) *Attorney, Agent, or Firm* — Renner, Kenner, Greive, Bobak, Taylor & Weber

(57) ABSTRACT

According to the present invention, a novel polyazamacrocyclic compound which is used as a bifunctional chelating agent (BFC) can be synthesized selectively and in high yield. The novel polyazamacrocyclic compound synthesized by this method chelates with metals and thus can be conjugated with bioactive molecules such as peptides, and can be used in the diagnosis and treatment of medical conditions.

7 Claims, 20 Drawing Sheets

(56) References Cited

OTHER PUBLICATIONS

Monica Shokken, et al., Accounts of Chemical Research Jul. 2009 vol. 42, No. 7, 832-841.
Michelle T. Ma, et al., Current Topics in Medicinal Chemistry, 2001, 11, 500-520.
Pandya, Darpan N., et al., "Revival of TE2A; a better chelate for Cu(II) ions than TETA?" Chem. Commun. 2910, 46, 3517-3519, publication date: Mar. 23, 2010.
Pandya, Darpan N., et al., "New Bifunctional Chelator for 64Cu-Immuno-Positron Emission Tomography," Bioconjugate Chemistry. 2013, 24, 1356-1366.
Wertz, Sebastian, et al., "Cross Dehydrogenative Coupling via Base-Promoted Homolytic Aromatic Substitution (BHAS): Synthesis of Fluorenones and Xanthones," ACS Med. Chem. Lett. 2013, 4, 928-931.
Wong, Edward H., et al., "Synthesis and Characterization of Cross-Bridged Cyclams and Pendant-Armed Derivatives and Structural Studies of Their Copper(II) Complexes," J. Am. Chem. Soc., 2000, 122, 10561-10572.
Baker, William C., et al., "Synthesis of Lipophilic Paramagnetic Contrast Agents," J. Org. Chem. 1999, 64, 2683-2689.
Pandya, Darpan N., et. al., "New Macrobicyclic Chelator for the Development of Ultrastable 64Cu-Radiolabeled Bioconjugate," Bioconjugate Chemistry. 2012, 23, 330-335.
Office Action issued by Korean Patent Office for KR20110095143, dated Sep. 28, 2012, and English-Language Summary.
Medicinal Chemistry, 2011, 7, 413-429.
Exp. Opin. Ther. Patents (2000) 10(7): 1057-1069.
Bioconjugate Chem. 2008, 19,1476-1484.
Chem. Commun., 2004, 2212-2213.
Bioconjugate Chem. 2001, 12, 7-34.
Bioconjugate Chem. 2007, 18, 1110-1117.
Nuclear Medicine and Biology 34 (2007) 29-35.
Bioconjugate Chem. 2006, 17, 68-76.
Advanced Drug Delivery Reviews 60 (2008) 1347-1370.
Bioconjugate Chem. 2007, vol. 18, No. 6, 1697-1700.
J. Am. Chem. Soc. 2007, vol. 129, 8962-8963.
Chem. Commun., 2007, 1331-1333.
Analytical Sciences Apr. 2008, vol. 24 463-469.
Bioconjugate Chem. 2002, vol. 13, 902-913.
Current Radiopharmaceuticals, 2001, 4, 109-121.
Cancer Biotherapy and Radiopharmaceuticals vol. 24, 2009, 379-393.
Accounts of Chemical Research Jul. 2009 vol. 42, No. 7, 832-841.
Current Topics in Medicinal Chemistry, 2001, 11, 500-520.

* cited by examiner

205 µCi
$^{64}$Cu-TE2A-c(RGDyK)

POLYAZAMACROCYCLIC COMPOUND, AND A PRODUCTION METHOD AND A BIOMEDICAL USE THEREFOR

TECHNICAL FIELD

The present invention relates to novel polyazamacrocyclic compounds which are capable of chelating a bioactive molecule with metal ions as a bifunctional chelator (BFC) and can be used for treatment and diagnosis, a method of preparation and biomedical use of the same.

BACKGROUND

Due to the ability of the macrocyclic molecules to coordinate with various metal cations, the discovery and synthesis of tetraazacycloalkane derivatives have attracted an increasing amount of attention for the past few years. Among them, cyclen (1,4,7,10-tetraazacyclododecane) and cyclam (1,4,8,11-tetraazacyclotetradecane) have been the focus of research, where it has been found that their macrocyclic molecular structure is very advantageous for forming metal complexes. Since such cyclic polyamines exhibit strong affinity to certain metal ions where they are capable of selectively binding with the metal ions, they can be used as metal catalysts, reaction sites for methalloenzyme, cleavers for phosphoric esters such as DNA and RNA, radioactive diagnosis and treatment, as well as MRI contrast agent, etc.

Among metal ions of high interest in the medical field, ions forming stable complexes with cyclen or cyclam derivatives include radioactive isotopes which can be used in nuclear medicine, as well as Gd which can be used as MRI contrast agent. $^{64}$Cu, $^{111}$In, $^{67}$Ga, $^{86}$Y, etc. are radioactive isotopes that can be used in diagnoses employing positron emission tomography (PET) or single photon emission computed tomography (SPECT), while $^{90}$Y is a radioactive isotope that can be used for therapy [Anderson C J, Welch M J. Radiometal-Labeled Agents (Non-Technetium) for Diagnostic Imaging. *Chem. Rev.* 1999, 99, 2219-2234; Anderson C J, Lewis J S. Radiopharmaceuticals for targeted radiotherapy of cancer. *Expert Opinion on Therapeutic Patents* 2000, 10, 1057-1069].

For instance, the use of radionuclides such as $^{64}$Cu in nuclear medicine or preclinical applications has been on the rise, and BFC is used to safely attach a radionuclide to a bioactive molecule, i.e. the target molecule. Thus, the development of BFC having excellent in vivo stability is very critical in designing a system for delivering a radionuclide in vivo.

A great deal of effort has been made to develop a ligand which is capable of chelating in a stable manner in vivo. The most common and general BFCs that has been studied are DOTA (1,4,7,10-tetraazacyclododecan-1,4,7,10-tetracetic acid) and TETA (1,4,8,11-tetraazacyclotetradecane-1,4,8,11-tetracetic acid). However, recent studies show that such generally used BFCs are rather unstable in vivo than the more recently developed BFCs such as cross-bridged tetraamine ligands and sarcophagine ligands due to the increased dissociation of metal.

Boswell et al. recently reported about cross-bridged cyclam derivatives for peptide conjugation and $^{64}$Cu radioactive labeling [C. Andrew Boswell. Celeste A. S. Regino, Kwamena E. Baidoo, Karen J. Wong, Ambika Bumb. Heng Xu, Diane E. Milenic, James A. Kelley. Christopher C. Lai. and Martin W. Brechbiel. Synthesis of a Cross-Bridged Cyclam Derivative for Peptide Conjugation and $^{64}$Cu Radiolabeling. *Bioconjugate Chem.* 2008, 19, 1476-1484]. They synthesized a $^{64}$Cu-cross-bridged(CB)-TE2A(1,8-bis-(carboxymethyl)-1,4,8,11-tetraazacyclotetradecane)-propeptide linker, and conjugated c[RGDfK(s)]. Furthermore, the Archibald group reported about NCSBz-CB-TE2A derivatives for bio-conjugation [Elizabeth A. Lewis, Ross W. Boyle and Stephen J. Archibald, Ultrastable complexes for in vivo use: a bifunctional chelator incorporating a cross-bridged macrocycle. *Chem. Commun.*, 2004, 2212-2213]. However, the selective functionalization of nitrogen in cyclic polyamines is not obvious, and is still a difficult task in the organic synthesis field. For example, the synthesis of NCSBz-CB-TE2A involves 13 steps including the preparation of starting materials, and the overall yield of the final product is only 8.7%. Therefore, there is a need to design novel polyazamacrocyclic compounds that can be effectively used as BFCs, and to develop synthetic methods for preparing such compounds easily in a high yield.

DETAILED DESCRIPTION

Technical Problem

The present invention is to overcome the above-mentioned problems of conventional techniques. The object of the invention is to provide novel polyazamacrocyclic compounds useful as BFC, to which various substituents may be introduced and which can be easily synthesized in high yield, as well as a process for preparing the same.

Another object of the invention is to provide a method of using novel polyazamacrocyclic compounds for biomedical use.

Technical Solution

In the present disclosure, a chelate means a compound in which a multi-dentate (at least bi-dentate) ligand is coordinated to a metal ion. The ligand here is referred to as a chelator.

Further, a conjugate compound in the present disclosure indicates a compound where a chelator is bound to a protein, a peptide or an antibody via conjugation. A metal chelating conjugate compound means a compound where a chelate is bound to a protein, a peptide or an antibody via conjugation, or where a conjugate compound is bound to a metal ion (complex ion).

A pharmaceutical formulation for diagnosis or treatment according to the present invention is comprised by conjugation of a chelate of metal radionuclide to a target molecule such as a protein, a peptide, an antibody or an antibody fragment by means of a BFC. Thus, BFC contains a reactive functional group such as an aromatic isothiocyanate group or an activated ester, and reacts with a nucleophilic binding site such as —$NH_2$, —SH or —OH of the target molecule [Liu, S., and Edwards, D. S. Bifunctional chelators for therapeutic lanthanide radiopharmaceuticals. *Bioconjugate Chem.* 2001, 12, 7-34]. The activated ester may be activated by those such as the functional groups shown below, but not limited thereto.

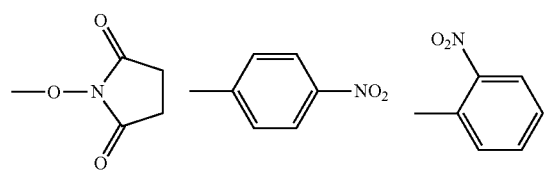

-continued

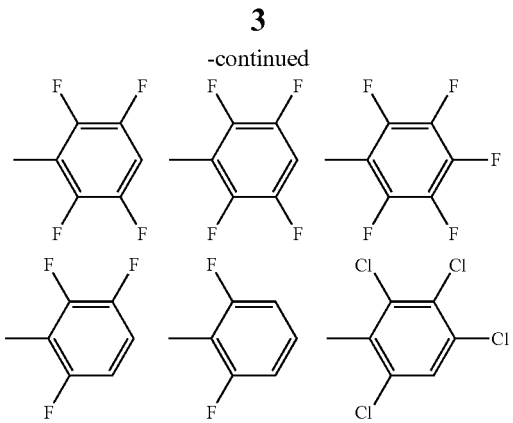

In a pharmaceutical formulation for diagnosis or treatment according to the present invention, a linker may be incorporated between the chelator and the target molecule for the purpose of controlling the pharmacokinetic properties and distribution in vivo, if necessary [Parry, J. J., Kelly, T. S., Andrews, R., and Rogers, B. E. In vitro and in vivo evaluation of 64Cu-labeled DOTA-linkerbombesin (7-14) analogues containing different amino acid linker moieties. Bioconjugate Chem. 2007, 18, 1110-1117; Dijkgraaf, I., Liu, S., Kruijtzer, J. A. W., Soede, A. C., Oyen, W. J. G., Liskamp, R. M. J., Corstens, F. H. M., and Boerman, O. C. Effects of linker variation on the in vitro and in vivo characteristics of an 111In-labeled RGD peptide. Nucl. Med. Biol. 2007, 34, 29-35; Li, L., Yazaki, P. J., Anderson, A.-L., Crow, D., Colcher, D., Wu, A. M., Williams, L. E., Wong, J. Y. C., Raubitschek, A., and Shively, J. E. Improved biodistribution and radioimmunoimaging with poly(ethylene glycol)-DOTA-conjugated anti-CEA diabody. Bioconjugate Chem. 2006, 17, 68-76]. Useful linkers include those represented by one of the following chemical formulas, but not limited thereto.

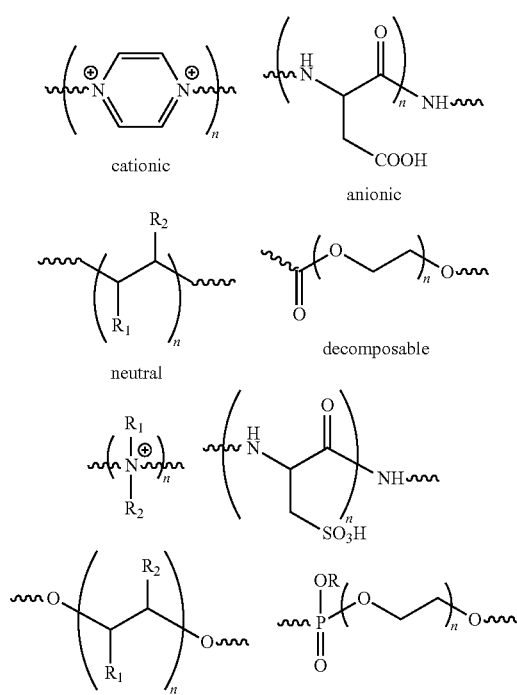

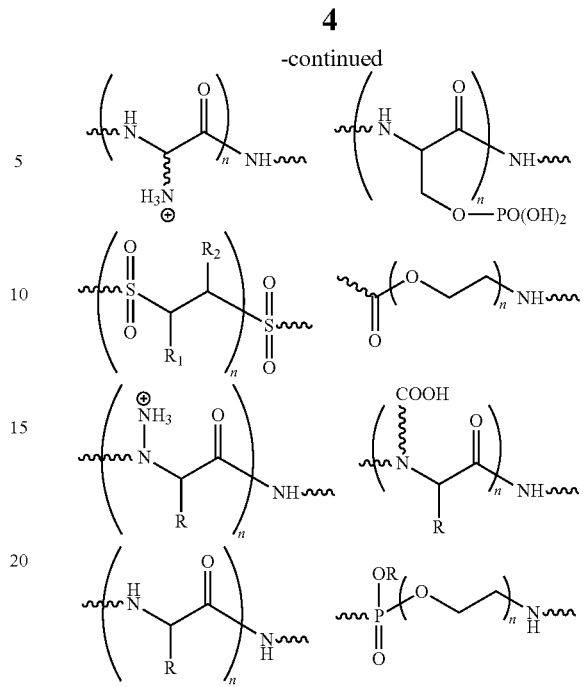

A polyazamacrocyclic compound according to the present invention, or a pharmaceutically acceptable salt thereof can be represented by Chemical Formula 1:

[Chemical Formula 1]

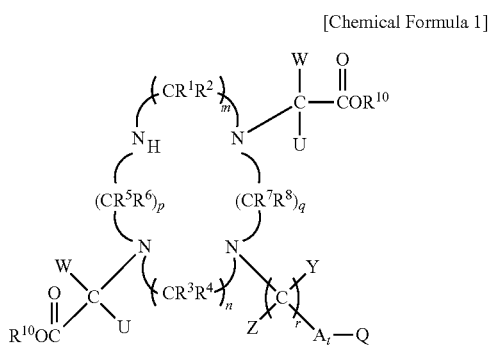

wherein,
m, n, p and q are identical to or different from one another, and individually represent an integer of 2 or 3,
r is an integer from 0 to 5,
t is an integer of 0 or 1,
r+t>0,
$R^1, R^2, R^3, R^4, R^5, R^6, R^7$ and $R^8$ are identical to or different from one another, and individually represent H, $C_{1-5}$ alkyl or $C_{3-6}$ cycloalkyl,
$R^{10}$ represents H, $C_{1-5}$ alkyl, $C_{3-6}$ cycloalkyl, or $C_{7-14}$ aralkyl,
U and W are identical to or different from one another, and individually represent H, $C_{1-5}$ alkyl or $C_{3-6}$ cycloalkyl,
Y and Z are identical to or different from one another, and individually represent H, $C_{1-5}$ alkyl or $C_{3-6}$ cycloalkyl,
A represents $C_{6-10}$ aryl,
Q represents H, nitro, amino, isothiocyanato, maleimido, ester, alkyne, aminoxy, thiol, azide or carboxylic acid.
According to the present invention, $C_{1-5}$ alkyl, $C_{3-6}$ cycloalkyl or $C_{7-14}$ aralkyl of $R^1, R^2, R^3, R^4, R^5, R^6, R^7, R^8, R^{10}$, U, W, Y and Z may be substituted with one or more substituent(s) selected from the group consisting of $C_{1-4}$ alkyl, halogen, hydroxyl, nitro, cyano, alkoxy, amino, ester and carboxylic group.

According to the present invention, $C_{6-10}$ aryl of A may be substituted with one or more substituent(s) selected from the group consisting of $C_{1-4}$ alkyl, halogen, hydroxyl, alkoxy, ester and carboxylic group.

According to the present invention, the above pharmaceutically acceptable salt, when the compound represented by Chemical Formula 1 contains a negatively charged component, comprises a cation or a cationic group selected from the group consisting of potassium, sodium, lithium, ammonium, silver, calcium and magnesium, or when the compound represented by Chemical Formula 1 contains a positively charged component, comprises an anion or an anionic group selected from the group consisting of $F^-$, $Cl^-$, $Br^-$, $I^-$, $ClO_4^-$, $BF_4^-$, $HCO_3^-$, $CH_3CO_2^-$, $CH_3SO_3^-$, $CH_3C_6H_4SO_3^-$, $CF_3SO_3^-$, $H_2PO_4^-$ and $B(C_6H_5)_4^-$, but are not limited thereto.

Polyazamacrocyclic compounds or pharmaceutically acceptable salts thereof according to the present invention serve as a BFC, and conjugate to a protein, a peptide, an antibody or an antibody fragment via an isothiocyanate group or an activated ester group.

Examples of polyazamacrocyclic compounds or pharmaceutically acceptable salts thereof according to the present invention include 1,8-bis-(carboxymethyl)-4-(4'-isothiocyanatobenzyl)-1,4,8,11-tetraazacyclotetradecane represented by Chemical Formula 2, 1,8-bis-(carboxymethyl)-4-(4'-isothiocyanatophenethyl)-1,4,8,11-tetraazacyclotetradecane represented by Chemical Formula 3, 1,7-bis-(carboxymethyl)-4-(4'-isothiocyanatobenzyl)-1,4,7,10-tetraazacyclododecane represented by Chemical Formula 4, 1,7-bis-(carboxymethyl)-4-(4'-isothiocyanatophenethyl)-1,4,7,10-tetraazacyclododecane represented by Chemical Formula 5, 1,8-bis-(carboxymethyl)-4-(4'-nitrophenethyl)-1,4,8,11-tetraazacyclotetradecane represented by Chemical Formula 6, and 1,8-bis-(carboxymethyl)-4-(methyl)-1,4,8,11-tetraazacyclotetradecane represented by Chemical Formula 7.

[Chemical Formula 2]

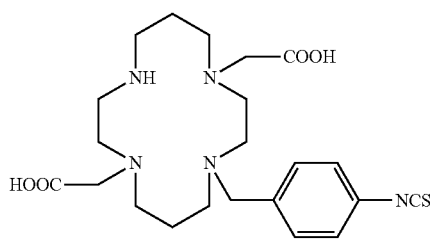

[Chemical Formula 3]

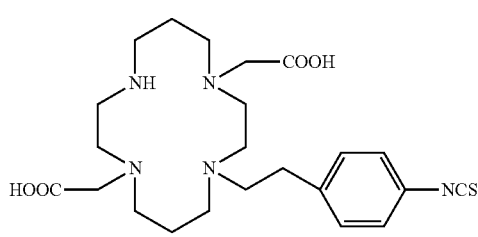

[Chemical Formula 4]

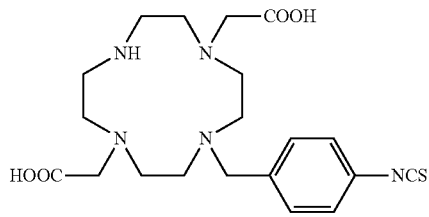

[Chemical Formula 5]

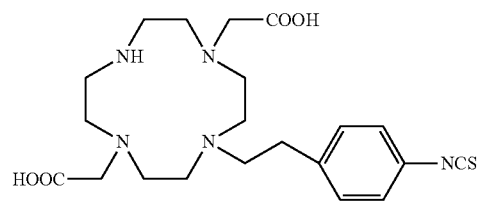

[Chemical Formula 6]

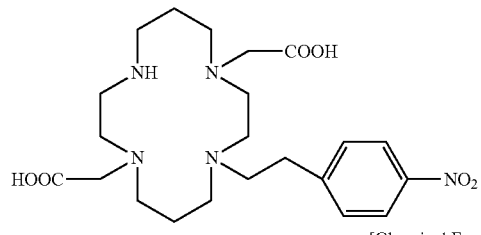

[Chemical Formula 7]

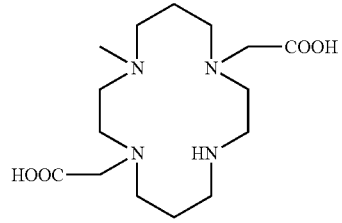

Metals which chelate polyazamacrocyclic compounds or pharmaceutically acceptable salts according to the present invention may be radioactive or non-radioactive, and selected from transition metals, lanthanide elements, actinide elements and metal main group elements. For example, chelating radioactive metals include $^{43}$Sc, $^{43}$V, $^{44}$Sc, $^{45}$Ti, $^{51}$Mn, $^{51}$Cr, $^{52}$Mn, $^{52}$Fe, $^{53}$Fe, $^{55}$Co, $^{56}$Co, $^{57}$Co, $^{58}$Co, $^{59}$Fe, $^{60}$Cu, $^{61}$Cu, $^{62}$Cu, $^{62}$Zn, $^{63}$Zn, $^{64}$Cu, $^{65}$Zn, $^{66}$Ga, $^{66}$Ge, $^{67}$Ge, $^{67}$Cu, $^{67}$Ga, $^{68}$CU, $^{68}$Ga, $^{69}$Ge, $^{69}$As, $^{70}$As, $^{70}$Se, $^{71}$Se, $^{71}$As, $^{72}$As, $^{73}$Se, $^{74}$Kr, $^{74}$Br, $^{75}$Se, $^{75}$Br, $^{76}$Br, $^{77}$Br, $^{77}$Kr, $^{78}$Br, $^{78}$Rb, $^{79}$Rb, $^{79}$Kr, $^{81}$Rb, $^{82}$Rb, $^{83}$Sr, $^{84}$Rb, $^{84}$Zr, $^{85}$Y, $^{86}$Y, $^{87}$Y, $^{87}$Zr, $^{88}$Y, $^{89}$Zr, $^{90}$Y, $^{89}$Zr, $^{92}$Tc, $^{93}$Tc, $^{94}$Tc, $^{95}$Tc, $^{95}$Ru, $^{95}$Rh, $^{96}$Rh, $^{97}$Rh, $^{97}$Ru, $^{98}$Rh, $^{99}$Rh, $^{94m}$Tc, $^{99m}$Tc, $^{100}$Rh, $^{101}$Ag, $^{102}$Ag, $^{102}$Rh, $^{103}$Ag, $^{103}$Ru, $^{104}$Ag, $^{105}$Ag, $^{105}$Ru, $^{106}$Ag, $^{108}$In, $^{109}$In, $^{110}$In, $^{111}$In, $^{113m}$In, $^{115}$Sb, $^{116}$Sb, $^{117}$Sb, $^{115}$Te, $^{116}$Te, $^{117}$Te, $^{117}$I, $^{118}$I, $^{118}$Xe, $^{119}$Xe, $^{119}$I, $^{119}$Te, $^{120}$I, $^{120}$Xe, $^{121}$Xe, $^{121}$I, $^{122}$I, $^{123}$Xe, $^{124}$I, $^{126}$I, $^{128}$I, $^{129}$La, $^{130}$La, $^{131}$La, $^{132}$La, $^{133}$La, $^{135}$La, $^{136}$La, $^{140}$Sm, $^{141}$Sm, $^{142}$Sm, $^{144}$Gd, $^{145}$Gd, $^{145}$Eu, $^{146}$Gd, $^{146}$Eu, $^{147}$Eu, $^{147}$Gd, $^{148}$Eu, $^{149}$Pr, $^{150}$Eu, $^{153}$Sm, $^{159}$Gd, $^{166}$Ho, $^{169}$Yb, $^{177}$Lu, $^{186}$Re, $^{188}$Re, $^{190}$Au, $^{191}$Au, $^{192}$Au, $^{193}$Au, $^{193}$Tl, $^{194}$Tl, $^{194}$Au, $^{195}$Tl, $^{196}$Tl, $^{197}$Tl, $^{198}$Tl, $^{200}$Tl, $^{200}$Bi, $^{201}$Tl, $^{202}$Bi, $^{203}$Bi, $^{205}$Bi, $^{206}$Bi, $^{211}$As, $^{212}$Bi or $^{225}$Ac, but are not limited thereto.

Suitable radioactive metals for SPECT include $^{67}$Ga, $^{68}$Ga, $^{99m}$Tc and $^{111}$In; suitable radioactive metals for PET include $^{60}$Cu, $^{61}$Cu, $^{62}$Cu, $^{64}$Cu, $^{86}$Y, $^{89}$Zr and $^{94m}$Tc; and suitable radioactive metals for therapy include $^{67}$Cu, $^{90}$Y, $^{153}$Sm, $^{166}$Ho, $^{177}$Lu, $^{186}$Re and $^{188}$Re [S. Liu, Bifunctional coupling agents for radiolabeling of biomolecules and target-specific delivery of metallic radionuclides, *Advanced Drug Delivery Reviews* 2008, 60, (2008) 1347-1370].

Among them, $^{64}$Cu is a useful nuclide for PET imaging and targeted radioactive therapy due to its half-life (12.7 hours), decay property (β+ (19%), β− (39%)), and suitability in terms of productivity in a large scale at high specificity by using a biomedical cyclotron.

The conjugate compounds according to the present invention include compounds represented by Chemical Formula 1 or pharmaceutically acceptable salts thereof, which are conjugated with an amino acid, a peptide, a protein, a nucleoside, a nucleotide, an aptamer, a nucleic acid, an enzyme, a lipid, a nitrogen-containing vitamin, a nitrogen-containing hormone, a medicine, a nanoparticle, an antibody or an antibody fragment.

The metal chelating conjugate compounds according to the present invention include compounds where the above chelate has been conjugated with an amino acid, a peptide, a protein, a nucleoside, a nucleotide, an aptamer, a nucleic acid, an enzyme, a lipid, a nitrogen-containing vitamin, a nitrogen-containing hormone, a medicine, a nanoparticle, an antibody or an antibody fragment; or a radioactive (in case of treatment or diagnosis by nuclear medicine) or non-radioactive (in case of contrast media for MRI) metal ion, derived from, for example, transition metals, lanthanide elements, actinide elements or metal main group elements has been bound to the above conjugate compound. The above metal chelating conjugate compounds are useful for treatment and diagnosis.

Contrast media according to the present invention include compounds represented by Chemical Formula 1 or pharmaceutically acceptable salts thereof. Specifically, using compounds represented by Chemical Formula 1 or pharmaceutically acceptable salts thereof as a chelator, they can be chelated with a metal ion having paramagnetic property, such as Mn, Fe, and Gd, and conjugated with a pathognomonic bio-material, to be used as, for instance, a contrast media for sonogram, for computed tomography (CT), for magnetic resonance imaging (MRI), for treatment/diagnosis via SPECT or PET.

Pharmaceutical formulations according to the present invention comprise the above metal chelating conjugate compounds and pharmaceutically acceptable vehicles, and are used for the diagnosis and treatment of tumor, dementia or mycoplasma, pathogen surface antigens, toxins, enzymes, allergens, medicine, biologically active molecules, bacteria, fungi, viruses, parasites, diseases relating to the autoimmune, heart or nervous system. The pharmaceutical formulations according to the present invention are used for the diagnosis and treatment of tumors, in particular.

Methods for diagnosing or treating a disease, a tumor for example, of a mammal other than human involve administering an effective amount of the above metal chelating conjugate compound to a mammal other than human.

Antibodies with which a chelator or a chelate according to the present invention would conjugate may be a monoclonal antibody or a polyclonal antibody, a chimeric antibody or a heteroantibody, or for example, an antibody containing a protein, which comprises a derivative of annexin, anti-CEA, tositumomab, trastuzumab, HUA33, epratuzumab, cG250, ibritumomab tiuxetan, or the like. Antibodies or antibody fragments that can be bound to the chelator or chelate according to the present invention may be prepared by techniques well known in the art.

Proteins with which a chelator or a chelate according to the present invention would conjugate may include for example albumin, TCII, HSA, annexin and Hb; peptides may include for example RGD-containing peptide, melanocyte-stimulating hormone (MSH) peptide, neurotensin, calcitonin, threotide, bombesin, neurotensin, urotensin II and angiotensin; nitrogen-containing vitamins may include for example vitamin A, B1, B2, B12, C, D2, D3, E, H and K; and nitrogen-containing hormones may include for example estradiol, progesterone and testosteron; but are not limited thereto.

The method of preparing the polyazamacrocyclic compound represented by Chemical Formula 1 or Chemical Formula 8 according to the present invention is described as follows:

[Chemical Formula 8]

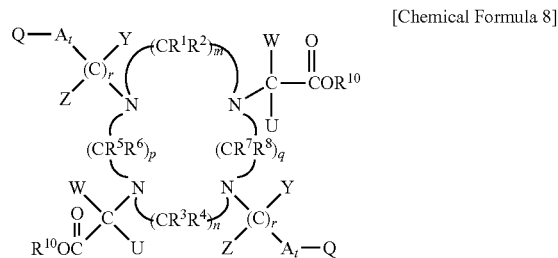

wherein, m, n, p, q, r, t, $R^1$, $R^2$, $R^3$, $R^4$, $R^5$, $R^6$, $R^7$, $R^8$, $R^{10}$, U, W, Y, Z, A and Q are defined as in Chemical Formula 1.

The method of preparing a polyazamacrocyclic compound represented by Chemical Formula 1 or 8 according to the present invention involves the steps of (i) reacting a compound represented by Chemical Formula 9 with α-halocarboxylic ester (X—CUW—CO$_2$R$^9$) to obtain a trans-N,N'-disubstituted compound represented by Chemical Formula 10, (ii) reacting the compound represented by Chemical Formula 10 with a base to obtain a compound represented by Chemical Formula 11, and (iii) incorporating a functional group —(CYZ)$_r$-A$_t$-Q [wherein, r, t, Y, Z, A and Q are defined as in Chemical Formula 1] to a secondary amine group in the cycle of compound represented by Chemical Formula 11 to form a compound represented by Chemical Formula 1 or 8:

[Chemical Formula 9]

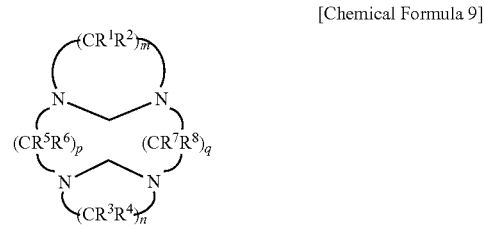

[Chemical Formula 10]

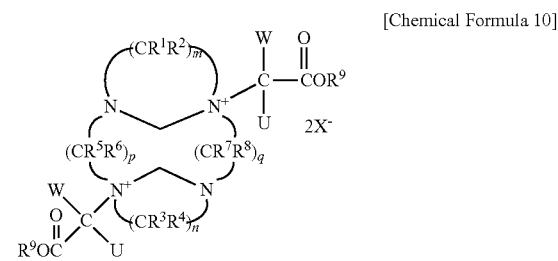

[Chemical Formula 11]

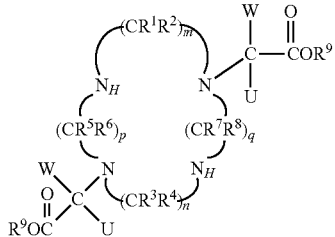

wherein m, n, p, q, $R^1$, $R^2$, $R^3$, $R^4$, $R^5$, $R^6$, $R^7$, $R^8$, U and W are defined as in Chemical Formula 1, $R^9$ represents $C_{1-5}$ alkyl, $C_{3-6}$ cycloalkyl, or $C_{7-14}$ aralkyl, and X represents F, Cl, Br or I.

In the compounds according to the present invention, $C_{1-5}$ alkyl, $C_{3-6}$ cycloalkyl or $C_{7-14}$ aralkyl of $R^9$ may be substituted with one or more substituent(s) selected from the group consisting of $C_{1-4}$ alkyl, halogen, hydroxyl, nitro, cyano, alkoxy, amino, ester and carboxylic group.

In the method of preparing a polyazamacrocyclic compound represented by Chemical Formula 1 or 8 according to the present invention, the reaction for introducing Q can be carried out according to a method well known in the art. For example, if Q of said Chemical Formula is H, step (iii) involves reacting the compound of Chemical Formula 11 with X—$(CYZ)_r$-$A_t$-H (X is defined as in Chemical Formula 10) to provide the compound of Chemical Formula 12 or 13. If Q of said Chemical Formula is nitro, amino, isothiocyanato or maleimido, step (iii) involves reacting the compound of Chemical Formula 11 with X—$(CYZ)_r$-$A_t$-$NO_2$ (X is defined as in Chemical Formula 10) to provide the compound of Chemical Formula 14 or 15.

[Chemical Formula 12]

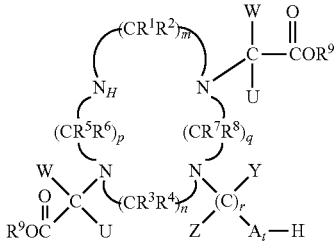

[Chemical Formula 13]

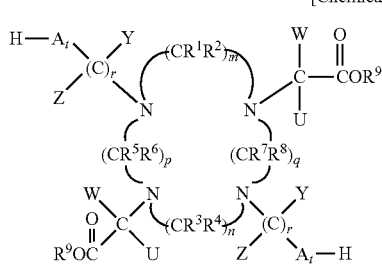

[Chemical Formula 14]

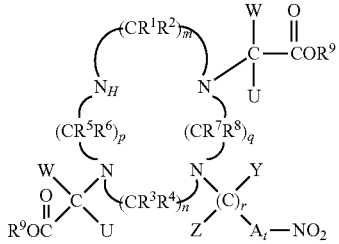

[Chemical Formula 15]

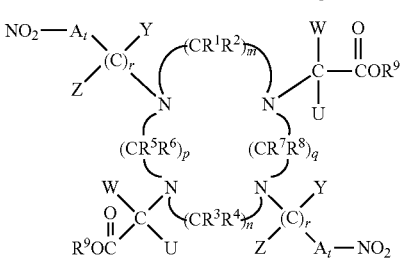

wherein m, n, p, q, $R^1$, $R^2$, $R^3$, $R^4$, $R^5$, $R^6$, $R^7$, $R^8$, U, W, Y, Z and A are defined as in Chemical Formula 1, and $R^9$ and X are defined as in Chemical Formula 10.

In the method of preparing a polyazamacrocyclic compound represented by Chemical Formula 1 or 8 according to the present invention, the additional reaction to introduce Q into the compound of Chemical Formula 14 or 15 can be carried out according to a method well known in the art. For example, if Q of said Chemical Formula is amino, step (iii) further involves the step of reducing the nitro group of the compound of Chemical Formula 14 or 15 to an amine group. If Q of said Chemical Formula is isothiocyanato, step (iii) further involves the step of reducing the nitro group of the compound of Chemical Formula 14 or 15 to an amine group, which is then reacted with thiophosgen. If Q is maleimido, step (iii) further involves the step of reducing the nitro group of the compound of Chemical Formula 14 or 15 to an amine group, which is then reacted with maleic anhydride.

Reaction of conventional cyclens or cyclams with 2 equivalents of alkyl or aryl halide form mixtures of monosubstituted-, disubstituted-, and even trisubstituted-macrocyclic molecules. Furthermore, depending on the relative position of the pendent arms, there would be three types of N,N'-disubstituted cyclic polyamines, i.e. two types of cis-disubstituted derivatives and one type of trans-disubstituted derivative. Among them, trans-N,N'-disubstituted cyclen and cyclam are particularly remarkable, because they can derive a stable 6-coordinated compound during chelate formation. Besides, trans-N,N'-double protected cyclen and cyclam are convenient precursors for synthesizing three-dimensional systems such as cryptands (cyclic polyether polyamine) based on cyclens or cyclams.

According to the present invention, a bisaminal compound (compound 9) is prepared as the starting material, which is then reacted with α-halocarboxylic ester (X—CUW—$CO_2R^9$) to obtain a trans-N,N'-disubstituted polyazamacrocyclic compound or derivatives thereof (compound 1, 8, 10 to 15) easily and with high yield.

In the present invention, $R^9$ as a protective group for carboxylic acid may be $C_{1-5}$ alkyl such as methyl, ethyl, n-propyl, isopropyl, n-butyl and tert-butyl, $C_{3-6}$ cycloalkyl such as cyclopentyl and cyclohexyl, $C_{6-12}$ aryl such as phenyl and α-naphthyl, phenyl-$C_{1-2}$ alkyl such as benzyl and phenethyl, $C_{7-14}$ aralkyl such as α-naphthyl-$C_{1-2}$ alkyl (e.g. α-naphthylmethyl), or silyl. The protective group may be substituted with one or more substituent(s) from $C_{1-4}$ alkyl, halogen, hydroxyl, nitro, cyano, alkoxy, amino, ester and carboxyl group, but are not limited thereto.

Among them, benzyl and tert-butyl as protective groups for the carboxylic group are desirable since they are stable in a basic environment but are easily removable under acidic conditions. In this regard, tert-butylbromoacetate or benzyl bromoacetate, for example, is used as α-halocarboxylic ester.

In order to remove the protective group for carboxylic groups, any conventional method can be used including, for example, reduction or acidolysis processes.

The above reduction process may include contact reduction using catalysts such as Pd/C, palladium black and platinum oxide, reduction by sodium in liquid ammonium, or reduction by means of dithiothreitol. The above acidolysis process may include acidolysis by means of an inorganic acid such as hydrogen fluoride, hydrogen bromide and hydrogen chloride, or an organic acid such as trifluoroacetic acid, methanesulfonic acid and trifluoromethanesulfonic acid, or a mixture thereof.

Inert solvents used for the method of preparation according to the present invention may include water, methanol, ethanol, isopropanol, isobutyl alcohol, tert-butyl alcohol, acetonitrile (MeCN), tetrahydrofuran (THF), chloroform ($CHCl_3$), dimethylformamide (DMF), dimethylsulfoxide (DMSO), benzene, toluene, xylene, dichloromethane, ethylene glycol, acetone, n-propyl ketone, trichloroethylene, ether, cyclohexanone, butyrolactone or a mixture thereof, but are not limited thereto.

In the method of preparation according to the present invention, the base used for the basic hydrolysis of compound represented by Chemical Formula 10 may include KOH, NaOH, $Ca(OH)_2$, $Li[NTf_2]$, $KF/Al_2O_3$ and the like, but are not limited thereto.

The trans-N,N'-disubstitution according to the present invention is carried out at an ambient temperature, but may be carried out at temperatures higher or lower than that, if necessary.

The reaction times for each step in the method of preparation according to the present invention are generally from 1 hour to 5 days, specifically from 3 hours to 2 days, but may be longer or shorter than that, if necessary.

Advantageous Effects

The polyazamacrocyclic compounds according to the present invention can be easily synthesized and conveniently purified in high yield while minimizing separation by chromatography which requires intensive time and labor.

According to the present invention, trans-N,N'-disubstituted cyclic polyamine can be selectively synthesized by reacting bisaminal and α-halocarboxylic ester.

The polyazamacrocyclic compounds according to the present invention act as a useful BFC, and can be applied in the biomedical field, for example for radioactive labeling of target molecules such as peptides, by chelating with a radionuclide such as $^{64}Cu$.

DETAILED DESCRIPTION

Figure 1:
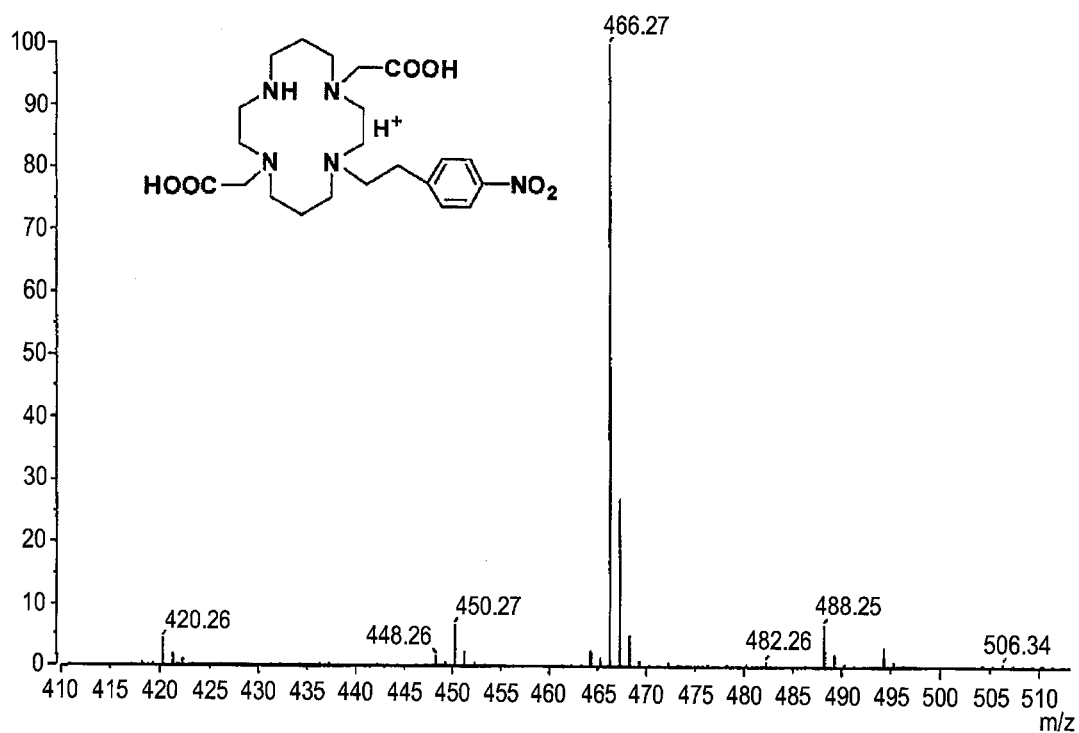
FIG. 1 shows a mass spectrum of TE2A-$NO_2$ according to an Example.

The present invention is described in further detail by Reference Examples and Examples provided below. However, those Reference Examples and Examples are merely for illustration to help understand the present invention, of which the scope is not limited thereto.

Reference Examples 1~8

By employing tert-butylbromoacetate and benzyl bromoacetate as an α-halocarboxylic ester (X—CUW—CO$_2$R$^9$), the conditions for reaction with compound (1) of Reaction Scheme (1) were examined.

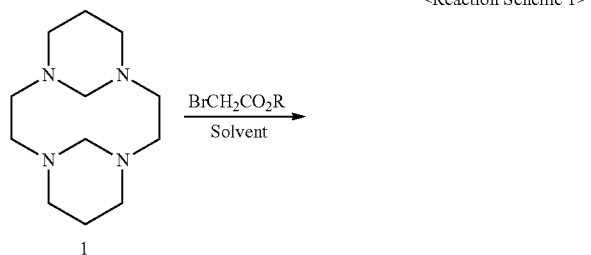

<Reaction Scheme 1>

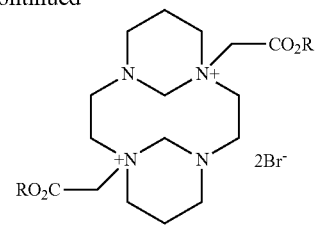

R = t-Bu, Bn

Specifically, as shown in Table 1 below, trans-N,N'-disubstituted cyclam was synthesized by varying the types of solvent and equivalent amounts of α-halocarboxylic ester.

TABLE 1

| Ref. Ex. | Reactants | Equivalent | Solvent | Yield (%) |
|---|---|---|---|---|
| 1 | tert-Butylbromoacetate | 4 | CH$_3$CN | 95 |
| 2 | tert-Butylbromoacetate | 2 | CH$_3$CN | 62 |
| 3 | tert-Butylbromoacetate | 4 | THF | 40 |
| 4 | tert-Butylbromoacetate | 4 | CHCl$_3$ | 45 |
| 5 | Benzyl bromoacetate | 4 | CH$_3$CN | 88 |
| 6 | Benzyl bromoacetate | 2 | CH$_3$CN | 52 |
| 7 | Benzyl bromoacetate | 4 | THF | 42 |
| 8 | Benzyl bromoacetate | 4 | CHCl$_3$ | 46 |

Reaction conditions: compound (1) = 0.325 g (1.44 mmol), solvent = 20 ml, ambient temperature, 24 hours As shown in Table 1 above, the most effective result of 95% yield was obtained when tert-butylbromoacetate was used as an alkylating agent, and CH$_3$CN (MeCN) as a solvent (Reference Example 1 of Table 1). When using THF and CHCl$_3$, moderate yields (40%, 45%) were obtained, respectively (Reference Examples 3 and 4 of Table 1). The amount of tert-butylbromoacetate used for the reaction was 2 equivalents or 4 equivalents, and better selectivity and yield were obtained when using 4 equivalents of tert-butylbromoacetate (Reference Examples 1 and 2 of Table 1).

Examples 1 and 2

By using tert-butylbromoacetate and benzyl bromoacetate as α-halocarboxylic ester (X—CUW—CO$_2$R$^9$), TE2A (1,8-bis-(carboxymethyl)-1,4,8,11-tetraazacyclotetradecane (compound (6)) was synthesized according to the route illustrated by the following Reaction Scheme:

<Reaction Scheme 2>

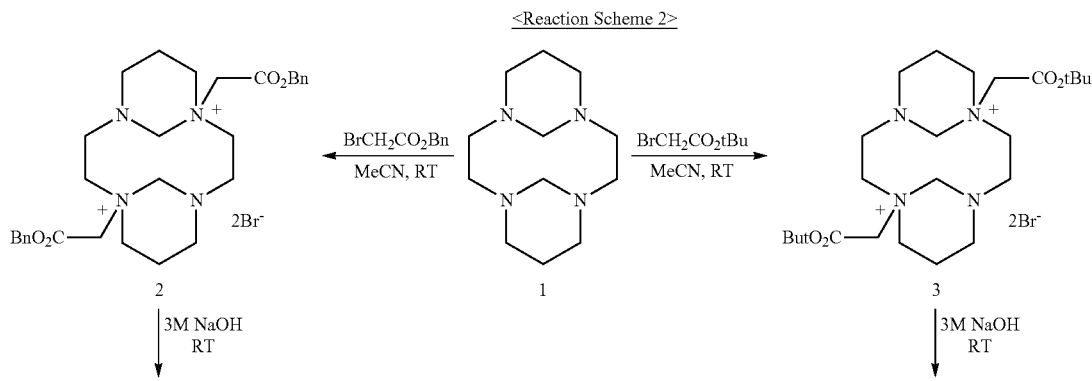

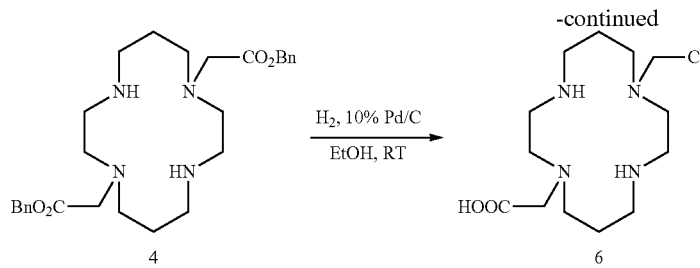

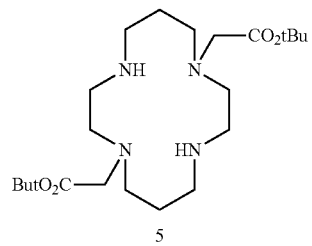

Example 1

Preparation of TE2A (6) using benzyl 2-bromoacetate

Preparation of 1,4,8,11-tetraazacyclo[9.3.1.1]-hexadecane (1)

Compound (1) was prepared according to a modified procedure which was previously reported by R. Guilard, C. Lecomte et al. in a amplified scale. In short, 2 equivalents of formaldehyde (15.1 ml, 37% in water) were rapidly added to an aqueous solution of cyclam (20.3 g, 0.10 M in 200 ml of distilled water) at a temperature of 0~5° C. After warming the reaction mixture to an ambient temperature, it was stirred for 2 hours. Then the reaction mixture was cooled to a temperature of 0 to 5° C., and a white precipitate thus generated was filtered and washed with cold water (2×10 ml). The obtained white solid was dissolved in $CHCl_3$ (200 ml) and dried over $MgSO_4$. Chloroform was evaporated under reduced pressure to obtain compound (1) (20.95 g, 92% yield). The spectrometric data of compound (1) exactly matched those reported previously. $^1H$ NMR (400 MHz, $CDCl_3$): δ 5.63-5.60 (dt, 2H, J=10.8 Hz), 3.14-3.12 (d, 4H, J=9.8 Hz), 2.90-2.87 (d, 2H, J=10.8 Hz), 2.84-8.80 (m, 4H), 2.65-2.58 (m, 4H), 2.38-2.35 (d, 4H, J=9.9 Hz), 2.3-2.1 (m, 2H), 1.17-1.14 (m, 2H); $^{13}C$ NMR (100.6 MHz, $CDCl_3$): δ 69.3, 54.1, 49.8, 20.6.

Preparation of 1,8-bis-(benzyloxycarbonylmethyl)-4,11-diazoniatricyclo[9.3.1.1]hexadecane dibromide (2)

Four equivalents of benzyl 2-bromoacetate (10.29 ml, 15.03 g, 65.6 mmol) were added to a portion of a stirred solution of compound (1) (3.68 g, 16.40 mmol) in MeCN (100 ml). The reaction mixture was stirred at an ambient temperature for 24 hours. A yellowish white precipitate thus generated was filtered and washed with MeCN (2×20 ml), and dried in vacuo. The crude product was recrystallized from ethanol to obtain compound (2) as a white solid (10.3 g, 92% yield). $^1H$ NMR (500 MHz, DMSO-$d_6$): δ 7.32-7.41 (m, 10H, ArH), 5.16 (s, 4H), 3.52 (s, 4H), 3.33 (s, 4H), 3.09 (brs, 8H), 2.85 (brs, 4H), 2.76-2.74 (t, 4H, J=5 Hz), 1.86 (brs, 4H); $^{13}C$ NMR (125 MHz, DMSO-$d_6$): δ 172.2, 135.5, 128.4, 128.2, 128.0, 66.4, 55.9, 54.0, 52.8, 51.2, 47.3, 44.1, 22.1, 18.5; HRMS (ESI) calculated for $C_{30}H_{42}N_4O_4$: 523.3284 [(M+H)$^+$], measured value: 523.3281 [(M+H)$^+$].

Preparation of 1,8-bis-(benzyloxycarbonylmethyl)-1,4,8,11-tetraazacyclotetradecane (4)

To compound (2) (9.23 g, 13.52 mmol) was added a 3 M NaOH solution (200 ml). After stirring for 3 hours, the resultant solution was extracted with $CHCl_3$ (3×100 ml), and the combined organic layer was washed with brine and dried over $MgSO_4$. Evaporation of the solvent under reduced pressure gave oil, which was then solidified to obtain compound (4) (6.58 g, 98% yield). $^1H$ NMR (500 MHz, $CDCl_3$): δ 7.20-7.14 (m, 10H, ArH), 4.92 (s, 4H), 3.25 (s, 4H), 2.71-2.66 (m, 12H), 2.49-2.47 (t, 4H, J=4.2 Hz), 1.70 (brs, 4H); $^{13}C$ NMR (125 MHz, $CDCl_3$): δ 171.3, 135.0, 128.3, 128.1, 127.8, 66.2, 54.7, 54.0, 51.9, 49.1, 46.3, 24.3; HRMS (FAB) calculated for $C_{28}H_{41}N_4O_4$: 497.3128 [(M+H)$^+$], measured value: 497.3129 [(M+H)$^+$].

Preparation of 1,8-bis-(carboxymethyl)-1,4,8,11-tetraazacyclotetradecane (TE2A) (6)

To a solution of compound (4) (0.48 g, 0.96 mmol) in absolute ethanol (40 ml) was added 10% Pd/C (0.12 g). The resultant mixture was stirred at an ambient temperature under $H_2$ atmosphere for 10 hours. The reaction mixture was filtered through a celite pad, and washed with ethanol (2×10 ml). The combined filtrate was evaporated in vacuo to give an oily residue, which was then treated with diethyl ether ($Et_2O$) to obtain an off-white solid (0.29 g, 98% yield). $^1H$ NMR (500 MHz, $D_2O$): δ 3.48 (brs, 2H), 3.01-3.19 (m, 10H), 2.80 (brs, 6H), 2.67 (brs, 2H), 1.84 (brs, 4H); $^{13}C$ NMR (125 MHz, $D_2O$): δ 179.0, 56.3, 55.7, 48.9, 45.4, 22.8; HRMS (FAB) calculated for $C_{14}H_{28}N_4O_4$: 317.2189 [(M+H)$^+$], measured value: 317.2185 [(M+H)$^+$].

Example 2

Preparation of TE2A (6) using tert-butylbromoacetate

Preparation of 1,8-bis-(carbo-tert-butoxymethyl)-4,11-diazoniatricyclo[9.3.1.1]hexadecane dibromide (3)

Four equivalents of tert-butylbromoacetate (9.38 ml, 12.38 g, 63.48 mmol) were added to a portion of a stirred solution of compound (1) (3.56 g, 15.87 mmol) in MeCN (100 ml). The reaction mixture was stirred at an ambient temperature for 24 hours. A yellowish white precipitate thus generated was filtered and washed with MeCN (2×20 ml), and dried in vacuo. The crude product was recrystallized from ethanol to obtain compound (3) as white solid (9.26 g, 95% yield). $^1H$ NMR (500 MHz, DMSO-$d_6$): δ 1.48 (s, 18H), 1.76-1.78 (d, 2H, J=8.5 Hz), 2.35-2.45 (m, 4H), 2.70-2.73 (d, 2H, J=15 Hz), 3.08-3.09 (d, 2H, J=5 Hz), 3.24-3.38 (m, 4H), 3.53-3.58 (m, 2H), 3.64-3.66 (d, 2H, J=10 Hz), 3.79-3.81 (d, 2H, J=11.5 Hz), 4.33-4.38 (t, 2H, J=14 Hz), 4.43-4.46 (d, 2H, J=16.5 Hz), 4.59-4.62 (d, 2H, J=16.5 Hz), 5.23-5.25 (d, 2H, J=9.5 Hz); $^{13}C$ NMR (125 MHz, DMSO-$d_6$): δ 163.5, 84.2, 76.5, 59.8, 57.2, 50.6, 47.7, 46.3, 27.5, 19.2; HRMS (ESI) calculated for $C_{24}H_{47}N_4O_4$: 455.3591 [(M+H)$^+$], measured value: 455.3594 [(M+H)$^+$].

Preparation of 1,8-bis-(carbo-tert-butoxymethyl)-1,4,8,11-tetraazacyclotetradecane (5)

To compound (3) (9.15 g, 14.89 mmol) was added a 3 M NaOH solution (200 ml). After stirring for 3 hours, the resultant solution was extracted with CHCl$_3$ (3×100 ml), and the combined organic layer was washed with brine and dried over MgSO$_4$. Evaporation of the solvent under reduced pressure gave oil, which was then solidified to obtain compound (5) (6.25 g, 98% yield). $^1$H NMR (500 MHz, CDCl$_3$): δ 3.25 (s, 4H), 2.72-2.59 (m, 16H), 1.71-1.69 (m, 4H), 1.37 (s, 18H); $^{13}$C NMR (125 MHz, CDCl$_3$): δ 170.43, 80.57, 54.74, 54.13, 52.47, 50.02, 47.59, 28.09, 25.78; HRMS (FAB) calculated for $C_{22}H_{45}N_4O_4$: 429.3441 [(M+H)$^+$], measured value: 429.3439 [(M+H)$^+$].

Preparation of 1,8-bis-(carboxymethyl)-1,4,8,11-tetraazacyclotetradecane (TE2A.2TFA) (6.2TFA)

Compound (5) (1.12 g, 2.61 mmol) was dissolved in a mixture of CF$_3$CO$_2$H (TFA) and CH$_2$Cl$_2$ (1:1 (v/v), 40 ml). The resultant mixture was stirred at an ambient temperature for 24 hours. The solvent was evaporated under reduced pressure to give an oily residue, which was then treated with Et$_2$O to obtain an off-white solid of compound (6) (1.39 g, 98% yield, calculated as 2 equivalents of TFA for the basic weight). $^1$H NMR (500 MHz, D$_2$O): δ 3.31 (brs, 2H), 3.22-2.95 (m, 8H), 2.94-2.72 (m, 8H), 2.64 (brs, 2H), 1.83 (brs, 4H); $^{13}$C NMR (125 MHz, D$_2$O): δ 180.9, 57.5, 56.9, 55.4, 49.2, 46.2, 23.7; HRMS (FAB) calculated for $C_{14}H_{28}N_4O_4$: 317.2189 [(M+H)$^+$], measured value: 317.2185 [(M+H)$^+$].

Examples 3 and 4

TE2A-NCS, to which different isothiocyanates have been introduced and functionalized, was prepared from compound (5) obtained from Example 2, via either one of the two routes shown in Reaction Scheme 3 below.

<Reaction Scheme 3>

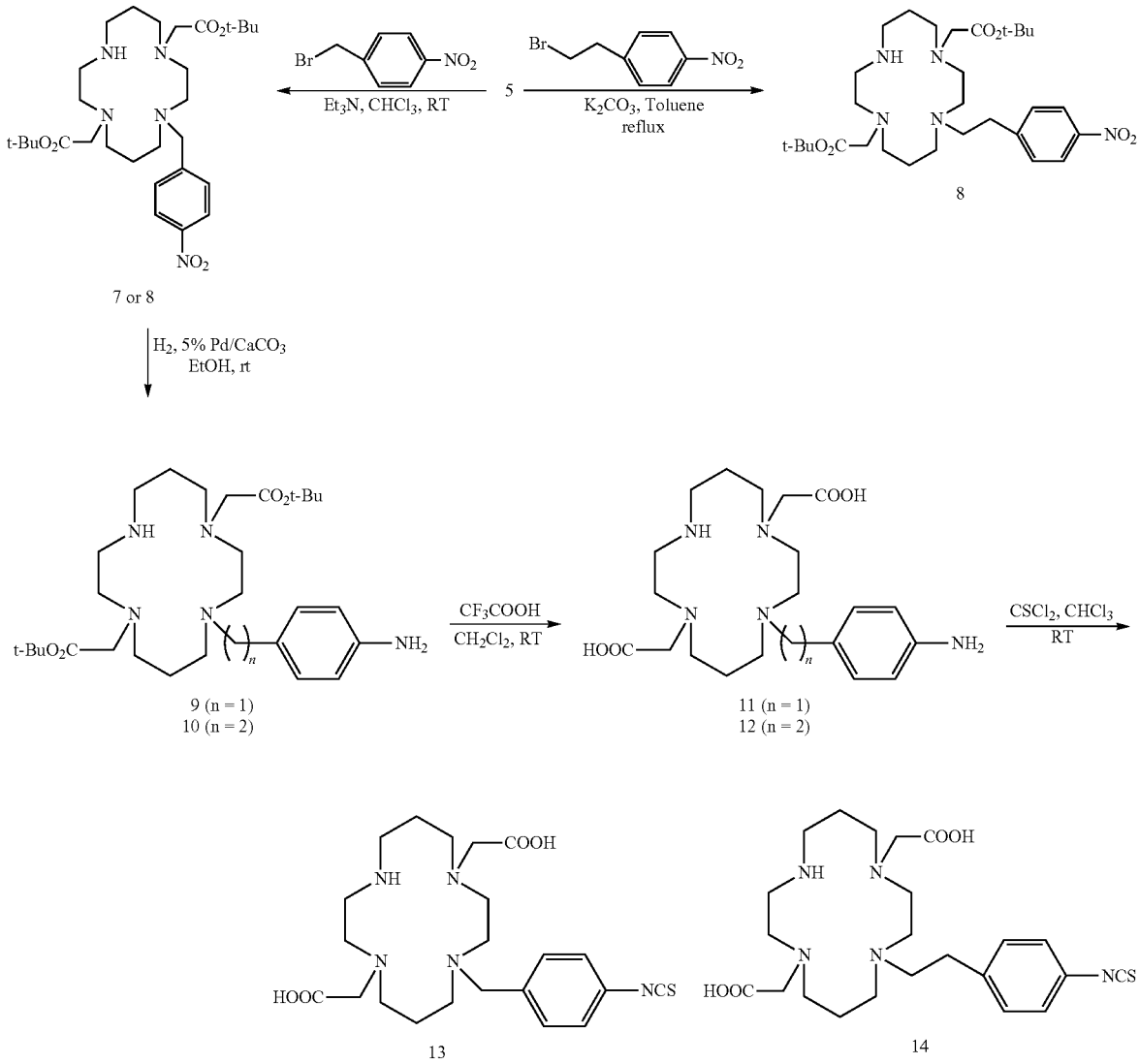

Example 3

Preparation of 1,8-bis-(carboxymethyl)-4-(4'-isothiocyanatobenzyl)-1,4,8,11-tetraazacyclotetradecane (13) using tert-butylbromoacetate

Preparation of 1,8-bis-(carbo-tert-butoxymethyl)-4-(4'-nitrobenzyl)-1,4,8,11-tetraazacyclotetradecane (7)

To a solution of compound (5) (1.27 g, 2.96 mmol) in dry $CHCl_3$ (50 ml) were added triethylamine (1.21 ml, 0.90 g, 8.88 mmol) and 4-nitrobenzyl bromide (0.64 g, 2.96 mmol). After stirring at an ambient temperature for 10 hours, the solvent was removed under reduced pressure, and the residue was purified through column chromatography on alumina (basic). Extraction with a mixture of ethyl acetate and methanol (10:2) gave a purified clear oil, which was then solidified to obtain compound (7) (1.30 g, 78% yield). $^1$H NMR (500 MHz, $CDCl_3$): δ 8.11-8.10 (dd, 2H), 7.55-7.53 (dd, 2H), 3.56 (s, 2H), 3.24 (s, 2H), 3.20-3.06 (m, 6H), 3.01 (brs, 2H), 2.70-2.58 (m, 4H), 2.54-2.42 (m, 4H), 2.39 (brs, 2H), 1.93 (brs, 2H), 1.75 (brs, 2H), 1.39-1.36 (dd, 18H); $^{13}$C NMR (125 MHz, $CDCl_3$): δ 171.3, 170.5, 147.0, 146.6, 130.1, 123.3, 81.9, 81.2, 58.1, 56.4, 55.8, 54.9, 53.1, 51.6, 51.5, 51.2, 49.6, 48.5, 46.1, 28.0, 25.1, 22.7; HRMS (FAB) calculated for $C_{29}H_{50}N_5O_6$: 564.3761 [(M+H)$^+$], measured value: 564.3757 [(M+H)$^+$].

Preparation of 1,8-bis-(carbo-tert-butoxymethyl)-4-(4'-aminobenzyl)-1,4,8,11-tetraazacyclotetradecane (9)

To a solution of compound (7) (1.22 g, 2.16 mmol) in absolute ethanol (100 ml) was added 5% Pd/$CaCO_3$ (0.31 g) to which lead (Pb) had been added as an inhibitor. The resultant mixture was stirred at an ambient temperature under $H_2$ atmosphere for 12 hours. The reaction mixture was filtered through a celite pad and washed with ethanol (2×20 ml). The combined filtrate was evaporated in vacuo to give an oily residue, which was then treated with $Et_2O$ to obtain an off-white solid of compound (9) (1.13 g, 98% yield). $^1$H NMR (500 MHz, $CDCl_3$): δ 7.07-7.06 (dd, 2H), 6.67-6.65 (dd, 2H), 3.39 (s, 4H), 3.30-3.14 (m, 4H), 3.12-3.01 (m, 4H), 2.77-2.75 (m, 2H), 2.70-2.42 (m, 8H), 1.96 (brs, 2H), 1.80 (brs, 2H), 1.46-1.45 (dd, 18H); $^{13}$C NMR (125 MHz, $CDCl_3$): δ 171.1, 170.7, 145.6, 130.7, 127.6, 115.0, 81.6, 81.2, 57.9, 55.4, 54.7, 54.1, 51.6, 51.5, 49.8, 49.7, 49.4, 46.0, 28.2, 24.3, 24.1, 22.5; HRMS (FAB) calculated for $C_{29}H_{52}N_5O_4$: 534.4019 [(M+H)$^+$], measured value: 534.4024 [(M+H)$^+$].

Preparation of 1,8-bis-(carboxymethyl)-4-(4'-aminobenzyl)-1,4,8,11-tetraazacyclotetradecane.2TFA (11.2TFA)

Compound (9) (0.92 g, 1.72 mmol) was dissolved in a mixture of TFA and $CH_2Cl_2$ (1:1 (v/v), 28 ml). The resultant mixture was stirred at an ambient temperature for 24 hours. The solvent was evaporated under reduced pressure to give an oily residue, which was then treated with $Et_2O$ to obtain an off-white solid of compound (11) (1.11 g, 99% yield, calculated as 2 equivalents of TFA for the basic weight). $^1$H NMR (500 MHz, $D_2O$): δ 7.20-7.10 (dd, 2H), 6.83-6.71 (dd, 2H), 4.1 (s, 2H), 3.52-2.42 (m, 20H), 2.1-1.62 (m, 4H); $^{13}$C NMR (125 MHz, $D_2O$): δ 192.7, 180.5, 180.4, 149.5, 148.2, 145.3, 133.1, 129.8, 128.8, 117.76, 116.4, 116.2, 114.0, 58.3, 57.1, 56.5, 55.0, 51.1, 48.8, 46.5, 45.8, 45.4, 23.7, 23.3, 22.7; HRMS (FAB) calculated for $C_{21}H_{36}N_5O_4$: 422.2767 [(M+H)$^+$], measured value: 422.2768 [(M+H)$^+$].

Preparation of 1,8-bis-(carboxymethyl)-4-(4'-isothiocyanatobenzyl)-1,4,8,11-tetraazacyclotetradecane-2TFA (13.2TFA)

To a solution of compound (11) (0.98 g, 1.51 mmol) in 0.5 M HCl (10 ml) was carefully added thiophosgene ($CSCl_2$) (3.47 ml, 5.21 g, 45.30 mmol) in $CHCl_3$ (10 ml). The reaction mixture was stirred at an ambient temperature for five hours to separate the layers. After removing the aqueous layer, the organic $CHCl_3$ layer was washed with water (2×50 ml). The combined aqueous layer was washed with $CHCl_3$ (3×50 ml) to remove the unreacted thiophosgene. Finally, the aqueous layer was lyophilized to obtain a white solid of compound (13) (1.02 g, 98% yield). $^1$H NMR (500 MHz, $D_2O$): δ 7.66-7.64 (dd, 2H), 7.49-7.47 (dd, 2H), 4.03 (s, 2H), 3.50-2.51 (m, 20H), 2.09 (brs, 2H), 1.87 (brs, 2H); $^{13}$C NMR (125 MHz, $D_2O$): δ 192.6, 176.2, 175.7, 133.7, 132.8, 132.0, 123.9, 56.4, 56.2, 54.5, 54.0, 51.4, 50.6, 50.2, 49.9, 49.28, 47.7, 45.0, 22.6, 21.7, 13.4; HRMS (FAB) calculated for $C_{22}H_{34}N_5O_4S$: 464.2332 [(M+H)$^+$], measured value: 464.2329 [(M+H)$^+$].

Example 4

Preparation of 1,8-bis-(carboxymethyl)-4-(4'-isothiocyanatophenethyl)-1,4,8,11-tetraazacyclotetradecane (14) using tert-butylbromoacetate

Preparation of 1,8-bis-(carbo-tert-butoxymethyl)-4-(4'-nitrophenethyl)-1,4,8,11-tetraazacyclotetradecane (8)

A solution of compound (5) (1.37 g, 3.19 mmol), 4-nitrophenethyl bromide (1.47 g, 6.38 mmol), anhydrous $K_2CO_3$ (1.32 g, 9.57 mmol) and KI (1.59 g, 9.57 mmol) dissolved in dry toluene (150 ml) was stirred under reflux for 24 hours. The solvent was evaporated from the reaction mixture under reduced pressure, and $CH_2Cl_2$ (250 ml) was added thereto. The resultant brown slurry was filtered through a celite pad, and washed with $CH_2Cl_2$ (2×30 ml). The solvent was evaporated from the combined filtrate under reduced pressure. The residue thus obtained was purified via alumina (basic) column chromatography using EtOAc/methanol (10:2) as an eluent to provide compound (8) as a yellow oil (1.26 g, 68% yield). $^1$H NMR (500 MHz, $CDCl_3$): δ 8.07-8.06 (dd, 2H), 7.35-7.33 (dd, 2H), 3.23-3.20 (dd, 4H), 2.97 (brs, 4H), 2.87-2.82 (m, 4H), 2.71-2.51 (m, 12H), 1.88 (brs, 2H), 1.61 (brs, 2H), 1.39-1.37 (dd, 18H); $^{13}$C NMR (125 MHz, $CDCl_3$): δ 170.7, 170.5, 148.6, 146.3, 129.5, 123.5, 81.3, 81.1, 55.7, 55.3, 55.0, 52.5, 52.0, 50.2, 49.5, 48.4, 46.1, 32.0, 28.1, 24.4, 24.3, 23.2; HRMS (FAB) calculated for $C_{30}H_{52}N_5O_6$: 578.3918 [(M+H)$^+$], measured value: 578.3915 [(M+H)$^+$].

Preparation of 1,8-bis-(carbo-tert-butoxymethyl)-4-(4'-aminophenethyl)-1,4,8,11-tetraazacyclotetradecane (10)

To a solution of compound (8) (1.15 g, 1.99 mmol) in absolute ethanol (100 ml) was added 5% Pd/$CaCO_3$ (0.31 g) to which lead (Pb) had been added as an inhibitor. The resultant mixture was stirred at an ambient temperature under $H_2$ atmosphere for 12 hours. The reaction mixture was filtered through a celite pad and washed with ethanol (2×20 ml). The solvent was evaporated from the combined filtrate in vacuo to give an oily residue, which was then treated with $Et_2O$ to obtain a white solid of compound (10) (1.09 g, 98% yield). $^1$H NMR (500 MHz, CDCl$_3$): δ 6.90-6.88 (dd, 2H), 6.55-6.54 (dd, 2H), 3.28-3.25 (dd, 4H), 2.96-2.94 (m, 2H), 2.88-2.86 (m, 2H), 2.81-2.79 (m, 2H), 2.70-2.68 (m, 2H), 2.64-2.62 (m, 2H), 2.56 (brs, 8H), 2.47 (brs, 2H), 1.86 (brs, 2H), 1.60 (brs, 2H), 1.39-1.37 (dd, 18H); $^{13}$C NMR (125 MHz, CDCl$_3$): δ 178.1, 170.5, 170.4, 144.5, 129.9, 129.2, 115.1, 81.1, 80.9, 55.3, 55.0, 54.8, 52.0, 51.7, 51.3, 50.4, 48.6, 48.3, 48.22, 45.8, 30.9, 28.1, 24.4, 23.8, 22.8; HRMS (FAB) calculated for C$_{30}$H$_{54}$N$_5$O$_4$: 548.4176 [(M+H)$^+$], measured value: 548.4172 [(M+H)$^+$].

Preparation of 1,8-bis-(carboxymethyl)-4-(4'-aminophenethyl)-1,4,8,11-tetraazacyclotetradecane.2TFA (12.2TFA)

Compound (10) (0.95 g, 1.73 mmol) was dissolved in a mixture of TFA and CH$_2$Cl$_2$ (1:1 (v/v), 28 ml). The resultant mixture was stirred at an ambient temperature for 24 hours. The solvent was evaporated under reduced pressure to give an oily residue, which was then treated with Et$_2$O to obtain a white solid of compound (12) (1.14 g, 99% yield, calculated as 2 equivalents of TFA for the basic weight). $^1$H NMR (500 MHz, D$_2$O): δ 7.45-7.43 (dd, 2H), 7.38-7.36 (dd, 2H), 3.49-3.12 (m, 18H), 2.82-2.62 (m, 6H), 1.91 (brs, 4H); $^{13}$C NMR (125 MHz, D$_2$O): δ 177.0, 176.6, 163.4, 163.1, 162.8, 162.5, 137.4, 130.4, 128.9, 123.4, 119.9, 117.5, 115.2, 112.9, 56.0, 54.9, 54.4, 53.3, 51.6, 50.5, 48.8, 47.3, 45.0, 31.5, 27.6, 22.8, 21.3; HRMS (FAB) calculated for C$_{22}$H$_{38}$N$_5$O$_4$: 436.2924 [(M+H)$^+$], measured value: 436.2925 [(M+H)$^+$].

Preparation of 1,8-bis-(carboxymethyl)-4-(4'-isothiocyanatophenethyl)-1,4,8,11-tetraazacyclotetradecane-2TFA (14.2TFA)

To a solution of compound (12) (1.05 g, 1.58 mmol) in 0.5 M HCl (10 ml) was carefully added thiophosgene (CSCl$_2$) (3.63 ml, 5.45 g, 47.40 mmol) in CHCl$_3$ (10 ml). The reaction mixture was stirred at an ambient temperature for 5 hours to separate the layers. After removing the aqueous layer, the organic CHCl$_3$ layer was washed with water (2×50 ml). The combined aqueous layer was washed with CHCl$_3$ (3×50 ml) to remove the unreacted thiophosgene. Finally, the aqueous layer was lyophilized to obtain a white solid of compound (14) (1.09 g, 98% yield). $^1$H NMR (500 MHz, D$_2$O): δ 7.67-7.65 (dd, 2H), 7.50-7.48 (dd, 2H), 3.923 (s, 4H), 3.48-2.52 (m, 20H), 1.98 (brs, 2H), 1.88 (brs, 2H); $^{13}$C NMR (125 MHz, D$_2$O): δ 187.9, 174.4, 173.2, 145.7, 137.5, 136.8, 135.1, 129.1, 128.6, 125.5, 122.6, 121.6, 60.4, 59.7, 57.8, 57.2, 56.9, 56.1, 54.5, 48.5, 35.5, 29.7, 23.3, 20.7; HRMS (FAB) calculated for C$_{23}$H$_{36}$N$_5$O$_4$S: 478.2488 [(M+H)$^+$], measured value: 478.2484 [(M+H)$^+$].

Example 5

From compound (4) prepared according to Example 1, functionalized TE2A-NCS compound (13), to which an isothiocyanate group was introduced, was prepared via the route illustrated in Reaction Scheme 4 below.

<Reaction Scheme 4>

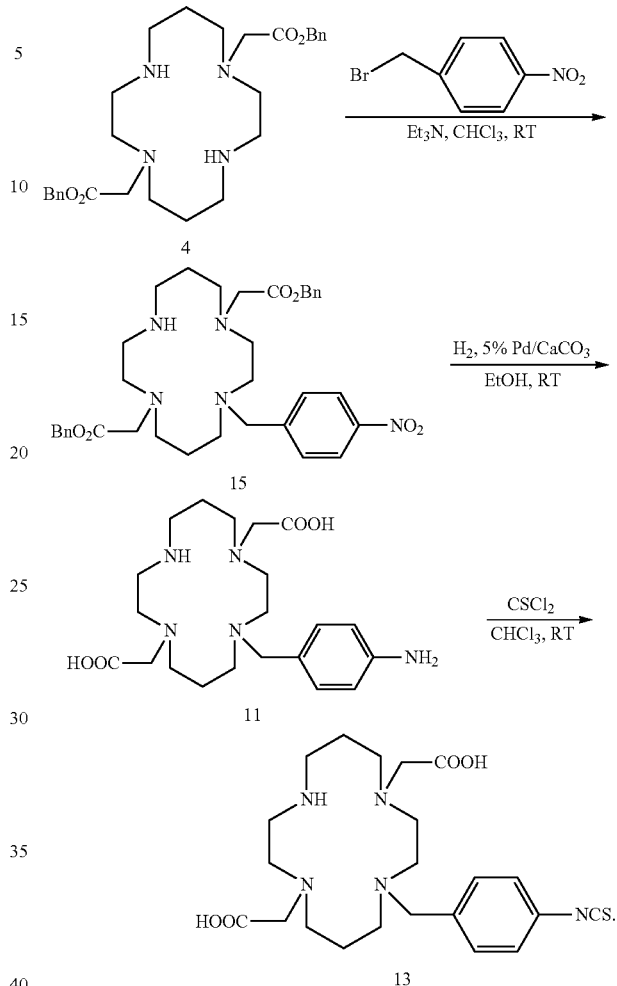

Preparation of 1,8-bis-(carboxymethyl)-4-(4'-isothiocyanatobenzyl)-1,4,8,11-tetraazacyclotetradecane (13) using benzyl 2-bromoacetate Preparation of 1,8-bis-(benzyloxycarbonylmethyl)-4-(4'-nitrobenzyl)-1,4,8,11-tetraazacyclotetradecane (15)

To a solution of compound (4) (1.17 g, 2.36 mmol) in dry CHCl$_3$ (50 ml) were added triethylamine (0.99 ml, 0.72 g, 7.08 mmol) and 4-nitrobenzyl bromide (0.51 g, 2.36 mmol). After stirring at an ambient temperature for 10 hours, the solvent was removed under reduced pressure, and the residue was purified through column chromatography on alumina (basic). Extraction with a mixture of acetate and methanol (10:2) gave a purified clear oil, which was then solidified to obtain compound (15) (1.13 g, 76% yield). $^1$H NMR (500 MHz, CDCl$_3$): δ 8.12-8.10 (dd, 2H), 7.51-7.49 (dd, 2H), 7.34-7.27 (m, 10H), 5.11 (s, 2H), 5.05 (s, 2H), 3.55 (s, 2H), 3.39 (s, 2H), 3.34 (s, 2H), 2.81 (brs, 2H), 2.74-2.72 (m, 4H), 2.67-2.64 (m, 6H), 2.59-2.57 (m, 2H), 2.46-2.44 (m, 2H), 1.71 (brs, 2H), 1.61-1.59 (m, 2H); $^{13}$C NMR (125 MHz, CDCl$_3$): δ 171.3, 170.8, 148.1, 146.9, 135.7, 129.3, 128.5, 128.2, 128.1, 123.3, 66.0, 65.8, 58.1, 55.5, 53.6, 53.1, 52.5,

Preparation of 1,8-bis-(carboxy)-4-(4'-aminobenzyl)-1,4,8,11-tetraazacyclotetradecane (11)

To a solution of compound (15) (1.08 g, 1.71 mmol) in absolute ethanol (100 ml) was added 5% Pd/CaCO$_3$ (0.31 g) to which lead (Pb) had been added as an inhibitor. The resultant mixture was stirred at an ambient temperature under H$_2$ atmosphere for 12 hours. The reaction mixture was filtered through a celite pad and washed with ethanol (2×20 ml). The combined filtrate was evaporated in vacuo to give an oily residue, which was then treated with Et$_2$O to obtain an off-white solid of compound (11) (0.71 g, 98% yield). $^1$H NMR (500 MHz, D$_2$O): δ 7.20-7.10 (dd, 2H), 6.83-6.71 (dd, 2H), 4.1 (s, 2H), 3.52-2.42 (m, 20H), 2.1-1.62 (m, 4H); $^{13}$C NMR (125 MHz, D$_2$O): δ 192.7, 180.5, 180.4, 149.5, 148.2, 145.3, 133.1, 129.8, 128.8, 117.76, 116.4, 116.2, 114.0, 58.3, 57.1, 56.5, 55.0, 51.1, 48.8, 46.5, 45.8, 45.4, 23.7, 23.3, 22.7; HRMS calculated for C$_{21}$H$_{36}$N$_5$O$_4$: 422.2767 [(M+H)$^+$], measured value: 422.2768 [(M+H)$^+$].

Preparation of 1,8-bis(carboxymethyl)-4-(4'-isothiocyanatobenzyl)-1,4,8,11-tetraazacyclotetradecane (13)

To a solution of compound (11) (0.89 g, 2.11 mmol) in 0.5 M HCl (10 ml) was carefully added thiophosgene (CSCl$_2$) (4.85 ml, 7.28 g, 63.3 mmol) in CHCl$_3$ (10 ml). The reaction mixture was stirred at an ambient temperature for 5 hours to separate the layers. After removing the aqueous layer, the organic CHCl$_3$ layer was washed with water (2×50 ml). The combined aqueous layer was washed with CHCl$_3$ (3×50 ml) to remove the unreacted thiophosgene. Finally, the aqueous layer was lyophilized to obtain a white solid of compound (13) (0.96 g, 98% yield). $^1$H NMR (500 MHz, D$_2$O): δ 7.66-7.64 (dd, 2H), 7.49-7.47 (dd, 2H), 4.03 (s, 2H), 3.50-2.51 (m, 20H), 2.09 (brs, 2H), 1.87 (brs, 2H); $^{13}$C NMR (125 MHz, D$_2$O): δ 192.6, 176.2, 175.7, 133.7, 132.8, 132.0, 123.9, 56.4, 56.2, 54.5, 54.0, 51.4, 50.6, 50.2, 49.9, 49.28, 47.7, 45.0, 22.6, 21.7, 13.4; HRMS (FAB) calculated for C$_{22}$H$_{34}$N$_5$O$_4$S: 464.2332 [(M+H)$^+$], measured value: 464.2329 [(M+H)$^+$].

Example 6

From compound (4) prepared according to Example 1, functionalized TE2A-NCS compound (14), to which an isothiocyanate group was introduced, was prepared via the route illustrated in Reaction Scheme 5 below.

<Reaction Scheme 5>

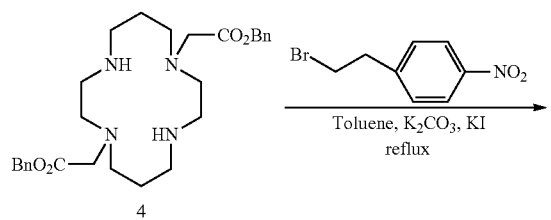

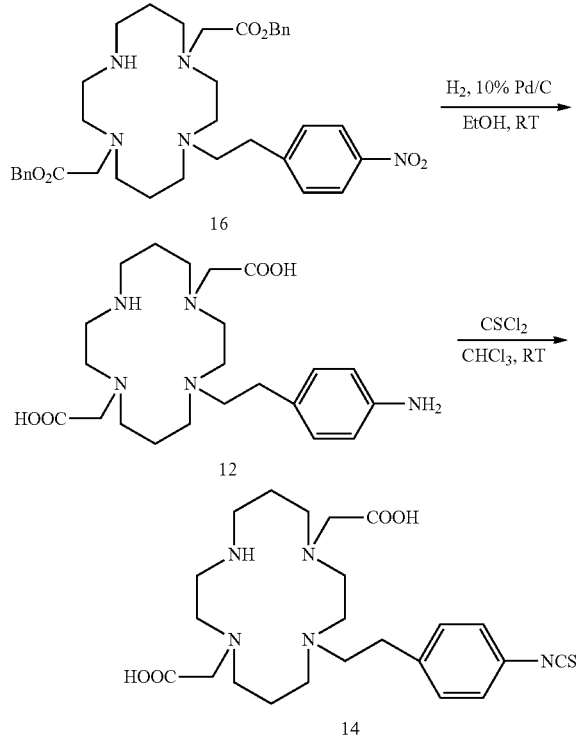

Preparation of 1,8-bis-(carboxymethyl)-4-(4'-isothiocyanatophenethyl)-1,4,8,11-tetraazacyclotetradecane (14) using benzyl 2-bromoacetate

Preparation of 1,8-bis-(benzyloxycarbonylmethyl)-4-(4'-nitrophenethyl)-1,4,8,11-tetraazacyclotetradecane (16)

A solution of compound (4) (1.19 g, 2.39 mmol), 4-nitrophenethyl bromide (1.09 g, 4.78 mmol), anhydrous K$_2$CO$_3$ (0.99 g, 7.17 mmol) and KI (1.19 g, 7.17 mmol) dissolved in dry toluene (150 ml) was stirred under reflux for 24 hours. The solvent was evaporated from the reaction mixture under reduced pressure, and CH$_2$Cl$_2$ (250 ml) was added thereto. The resultant brown slurry was filtered through a celite pad, and washed with CH$_2$Cl$_2$ (2×30 ml). The solvent was evaporated from the combined filtrate under reduced pressure. The residue thus obtained was purified via alumina (basic) column chromatography using EtOAc/methanol (10:2) as an eluent to provide compound (16) as a yellow oil (1.08 g, 70% yield). $^1$H NMR (500 MHz, CDCl$_3$): δ 8.14-8.12 (dd, 2H), 7.49-7.47 (dd, 2H), 7.33-7.28 (m, 10H), 5.09 (s, 2H), 5.03 (s, 4H), 3.46 (s, 2H), 3.36 (s, 2H), 3.25 (s, 2H), 2.87 (brs, 2H), 2.76-2.72 (m, 4H), 2.65-2.63 (m, 6H), 2.59-2.57 (m, 2H), 2.44-2.42 (m, 2H), 1.69 (brs, 2H), 1.62-1.59 (m, 2H); $^{13}$C NMR (125 MHz, CDCl$_3$): δ 171.3, 170.8, 148.1, 146.9, 135.7, 129.3, 128.5, 128.2, 128.1, 123.3, 66.0, 65.8, 58.1, 55.5, 53.6, 53.1, 52.5, 52.0, 51.2, 49.6, 47.9, 47.2, 25.7; HRMS (FAB) calculated for C$_{36}$H$_{48}$N$_5$O$_6$: 646.3605 [(M+H)$^+$], measured value: 646.3602 [(M+H)$^+$].

Preparation of 1,8-bis-(carboxymethyl)-4-(4'-aminophenethyl)-1,4,8,11-tetraazacyclotetradecane (12)

To a solution of compound (16) (0.86 g, 1.33 mmol) in absolute ethanol (100 ml) was added 10% Pd/C (0.26 g). The resultant mixture was stirred at an ambient temperature under H$_2$ atmosphere for 12 hours. The reaction mixture was filtered through a celite pad and washed with ethanol (2×20 ml). The solvent was evaporated from the combined filtrate in vacuo to give an oily residue, which was then treated with Et$_2$O to obtain a white solid of compound (12) (0.57 g, 98% yield). $^1$H NMR (500 MHz, D$_2$O): δ 7.45-7.43 (dd, 2H), 7.38-7.36 (dd, 2H), 3.49-3.12 (m, 18H), 2.82-2.62 (m, 6H), 1.91 (brs, 4H); $^{13}$C NMR (125 MHz, D$_2$O): δ 177.0, 176.6, 163.4, 163.1, 162.8, 162.5, 137.4, 130.4, 128.9, 123.4, 119.9, 117.5, 115.2, 112.9, 56.0, 54.9, 54.4, 53.3, 51.6, 50.5, 48.8, 47.3, 45.0, 31.5, 27.6, 22.8, 21.3; FIRMS (FAB) calculated for C$_{22}$H$_{38}$N$_5$O$_4$: 436.2924 [(M+H)$^+$], measured value: 436.2925 [(M+H)$^+$].

Preparation of 1,8-bis(carboxymethyl)-4-(4'-isothiocyanatophenethyl)-1,4,8,11-tetraazacyclotetradecane (14)

To a solution of compound (12) (0.79 g, 1.81 mmol) in 0.5 M HCl (10 ml) was carefully added thiophosgene (CSCl$_2$) (4.17 ml, 6.26 g, 54.4 mmol) in CHCl$_3$ (10 ml). The reaction mixture was stirred at an ambient temperature for 5 hours to separate the layers. After removing the aqueous layer, the organic CHCl$_3$ layer was washed with water (2×50 ml). The combined aqueous layer was washed with CHCl$_3$ (3×50 ml) to remove the unreacted thiophosgene. Finally, the aqueous layer was lyophilized to obtain a white solid of compound (14) (0.85 g, 98% yield). $^1$H NMR (500 MHz, D$_2$O): δ 7.67-7.65 (dd, 2H), 7.50-7.48 (dd, 2H), 3.923 (s, 4H), 3.48-2.52 (m, 20H), 1.98 (brs, 2H), 1.88 (brs, 2H); $^{13}$C NMR (125 MHz, D$_2$O): δ 187.9, 174.4, 173.2, 145.7, 137.5, 136.8, 135.1, 129.1, 128.6, 125.5, 122.6, 121.6, 60.4, 59.7, 57.8, 57.2, 56.9, 56.1, 54.5, 48.5, 35.5, 29.7, 23.3, 20.7; HRMS (FAB) calculated for C$_{23}$H$_{36}$N$_5$O$_4$S: 478.2488 [(M+H)$^+$], measured value: 478.2484 [(M+H)$^+$].

Example 7

Functionalized DO2A (1,7-bis-(carboxymethyl)-1,4,7,10-tetraazacyclododecane)-NCS (compound (24)), to which an isothiocyanate group was introduced, was synthesized via the route illustrated in Reaction Scheme 6 below.

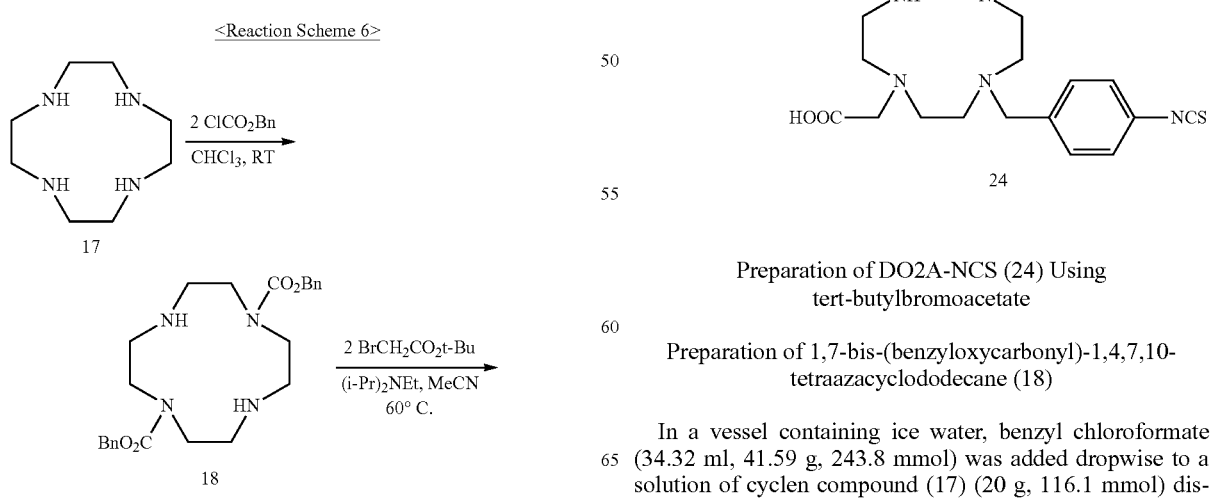

Preparation of DO2A-NCS (24) Using tert-butylbromoacetate

Preparation of 1,7-bis-(benzyloxycarbonyl)-1,4,7,10-tetraazacyclododecane (18)

In a vessel containing ice water, benzyl chloroformate (34.32 ml, 41.59 g, 243.8 mmol) was added dropwise to a solution of cyclen compound (17) (20 g, 116.1 mmol) dissolved in CHCl$_3$ (200 ml). The temperature was maintained below 0° C. When the addition was completed, the mixture was stirred at an ambient temperature for 10 hours so that sufficient solid was formed. The solvent was then evaporated under reduced pressure to obtain a white solid, to which ether (200 ml) was added. The solid was filtered and washed with ether (2×50 ml). Drying in vacuo while maintaining the temperature at 45° C. gave dihydrochloride salt (59.01 g, 99% yield) as a white solid. To the solid was added 3 M NaOH (250 ml) to obtain the free base. The aqueous layer was extracted with $CHCl_3$ (3×200 ml), and the combined extract was washed with brine and dried over $MgSO_4$. The solvent was removed by using a rotary evaporator, and the residue was dried in vacuo for several hours to obtain a solidified clear oily compound (18) (50.12 g, 98% yield). $^1$H NMR (400 MHz, $CDCl_3$): δ 7.52-7.32 (m, 10H), 5.18 (s, 4H), 3.83-3.65 (m, 8H), 3.10-2.83 (m, 8H); $^{13}$C NMR (100.6 MHz, $CDCl_3$): δ 156.5, 136.3, 136.2, 129.0, 128.8, 128.7, 128.4, 128.3, 128.2, 68.1, 68.0, 50.9, 50.8, 50.6, 50.5, 50.3, 50.0, 49.6, 49.3.

Preparation of 1,7-bis-(benzyloxycarbonyl)-4,10-bis (carbo-tert-butoxymethyl)-1,4,7,10-tetraazacyclododecane (19)

To a solution of compound (18) (6.84 g, 15.53 mmol) in dry MeCN (150 ml) were added N,N'-diisopropylethyl amine (13.52 ml, 10.03 g, 77.63 mmol) and tert-butyl bromoacetate (4.82 ml, 6.36 g, 32.61 mmol). The reaction mixture was slowly heated to 60° C., and stirred for 10 hours. The solvent was evaporated under reduced pressure, and the residue was dissolved in a $Na_2CO_3$ solution (100 ml). The aqueous layer was extracted with $CH_2Cl_2$ (3×100 ml), and the combined extract was washed with brine and dried over $MgSO_4$ to obtain a concentrated white oil. The oil was recrystallized from $Et_2O$ to provide compound (19) as a white solid (9.55 g, 92% yield). $^1$H NMR (500 MHz, $CDCl_3$): δ 7.26-7.19 (m, 10H), 5.04 (s, 4H), 3.34-3.05 (m, 12H), 2.9-2.6 (m, 8H), 1.35 (s, 18H); $^{13}$C NMR (125 MHz, $CDCl_3$): δ 170.4, 156.3, 136.7, 128.3, 127.8, 127.7, 80.8, 66.8, 55.8, 54.2, 46.9, 46.5, 28.1; HRMS (FAB) calculated for $C_{36}H_{53}N_4O_8$: 669.3863 [(M+H)$^+$], measured value: 669.3860 [(M+H)$^+$].

Preparation of 1,7-bis(carbo-tert-butoxymethyl)-1,4,7,10-tetraazacyclododecane (20)

To a solution of compound (19) (8.52 g, 12.74 mmol) in ethanol (130 ml) was added 10% Pd/C (2.6 g). The resultant mixture was stirred at an ambient temperature in the presence of $H_2$ (g) for 12 hours. The reaction mixture was filtered through a celite pad and washed with ethanol (2×20 ml). The filtrate was evaporated in vacuo to give an oily residue, which was then treated with $Et_2O$ to obtain a white solid of compound (20) (4.85 g, 97% yield). $^1$H NMR (500 MHz, $CD_3OD$): δ 3.44 (s, 4H), 2.91 (s, 16H), 1.47 (s, 18H); $^{13}$C NMR (125 MHz, $CD_3OD$): δ 173.0, 82.8, 57.4, 52.2, 46.5, 28.5; HRMS (FAB) calculated for $C_{20}H_{41}N_4O_4$: 401.3128 [(M+H)$^+$], measured value: 401.3132 [(M+$^1$-1)$^+$].

Preparation of 1,7-bis-(carbo-tert-butoxymethyl)-4-(4'-nitrobenzyl)-1,4,7,10-tetraazacyclododecane (21)

To a solution of compound (20) (1.85 g, 4.62 mmol) in dry $CHCl_3$ (50 ml) were added triethylamine (1.93 ml, 1.40 g, 13.86 mmol) and 4-nitrobenzylbromide (0.99 g, 4.62 mmol). After stirring the mixture at an ambient temperature for 10 hours, the solvent was removed under reduced pressure, and the residue was purified via alumina (basic) column chromatography. Extraction with ethyl acetate/methanol (10:2) gave a solidified clear oily compound (21) (1.98 g, 80% yield).

Preparation of 1,7-bis-(carbo-tert-butoxymethyl)-4-(4'-aminobenzyl)-1,4,7,10-tetraazacyclododecane (22)

To a solution of compound (21) (1.72 g, 3.21 mmol) in absolute ethanol (100 ml) was added 5% $Pd/CaCO_3$ (0.31 g) to which lead (Pb) had been added as an inhibitor. The resultant mixture was stirred at an ambient temperature in the presence of $H_2$ (g) for 12 hours. The reaction mixture was filtered through a celite pad and washed with ethanol (2×20 ml). The filtrate was evaporated in vacuo to give an oily residue, which was then treated with $Et_2O$ to obtain a white solid of compound (22) (1.59 g, 98% yield).

Preparation of 1,7-bis-(carboxymethyl)-4-(4'-aminobenzyl)-1,4,7,10-tetraazacyclododecane.2TFA (23.2TFA)

Compound (22) (1.48 g, 2.93 mmol) was dissolved in a mixture of TFA and $CH_2Cl_2$ (1:1 (v/v), 48 ml). The mixture was stirred at an ambient temperature for 24 hours. The solvent was removed under reduced pressure to give an oily residue, which was then treated with $Et_2O$ to obtain a white solid of compound (23) (1.80 g, 99% yield; calculated as 2 equivalents of TFA for the basic weight).

Preparation of 1,7-bis-(carboxymethyl)-4-(4'-isothiocyanatobenzyl)-1,4,7,10-tetraazacyclododecane.2TFA (24.2TFA)

To a solution of compound (23) (1.56 g, 2.51 mmol) in 0.5 M HCl (10 ml) was carefully added thiophosgene ($CSCl_2$) (5.77 ml, 8.66 g, 75.30 mmol) dissolved in $CHCl_3$ (10 ml). The reaction mixture was stirred at an ambient temperature for 5 hours, and the resultant layers were separated. The aqueous layer was extracted, and the organic $CHCl_3$ layer was washed with water (2×50 ml). The combined aqueous layer was washed with $CHCl_3$ (3×50 ml) to remove the unreacted thiophosgene. Finally, the aqueous layer was lyophilized to obtain a white solid of compound (24) (1.63 g, 98% yield).

Example 8

Functionalized DO2A-NCS compound (28), to which an isothiocyanate group was introduced, was prepared by using tert-butylbromoacetate as an α-halocarboxylic ester (X—CUW—$CO_2R^9$) via the route illustrated in Reaction Scheme 7 below.

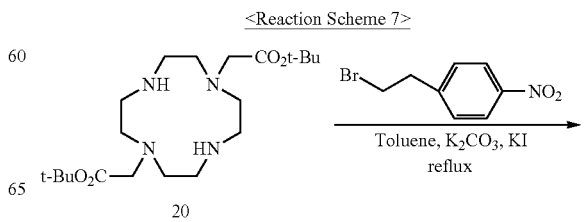

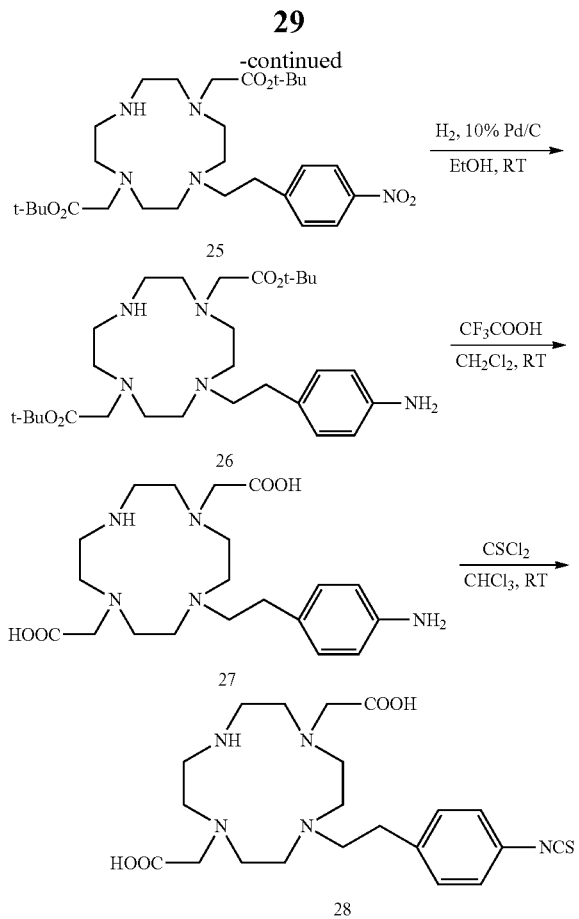

Preparation of DO2A-NCS (28) using tert-butylbromoacetate

Preparation of 1,7-bis-(carbo-tert-butoxymethyl)-4-(4'-nitrophenethyl)-1,4,7,10-tetraazacyclododecane (25)

A solution of compound (20) (1.56 g, 3.89 mmol), 4-nitrophenethyl bromide (1.79 g, 7.78 mmol), anhydrous $K_2CO_3$ (1.61 g, 11.67 mmol) and KI (1.94 g, 11.67 mmol) dissolved in dry toluene (150 ml) was stirred for 24 hours. The solvent was evaporated from the reaction mixture under reduced pressure, and $CH_2Cl_2$ (250 ml) was added thereto. The resultant brown slurry was filtered through a celite pad, and washed with $CH_2Cl_2$ (2×30 ml). The solvent was evaporated from the combined filtrate under reduced pressure. The residue thus obtained was purified via alumina (basic) column chromatography using EtOAc/methanol (10:2) as an eluent to provide compound (25) as a yellow oil (1.46 g, 68% yield).

Preparation of 1,7-bis-(carbo-tert-butoxymethyl)-4-(4'-aminophenethyl)-1,4,7,10-tetraazacyclododecane (26)

To a solution of compound (25) (1.35 g, 2.46 mmol) in absolute ethanol (100 ml) was added 10% Pd/C (0.41 g). The resultant mixture was stirred at an ambient temperature in the presence of $H_2$ (g) for 12 hours. The reaction mixture was filtered through a celite pad and washed with ethanol (2×20 ml). The filtrate was evaporated in vacuo to give an oily residue, which was then treated with $Et_2O$ to obtain a white solid of compound (26) (1.25 g, 98% yield).

Preparation of 1,7-bis-(carboxymethyl)-4-(4'-aminophenethyl)-1,4,7,10-tetraazacyclododecane.2TFA (27.2TFA)

Compound (26) (1.12 g, 2.16 mmol) was dissolved in a mixture of TFA and $CH_2Cl_2$ (1:1 (v/v), 35 ml). The mixture was stirred at an ambient temperature for 24 hours. The solvent was removed under reduced pressure to give an oily residue, which was then treated with $Et_2O$ to obtain a white solid of compound (27) (1.37 g, 99% yield; calculated as 2 equivalents of TFA for the basic weight).

Preparation of 1,7-bis-(carboxymethyl)-4-(4'-isothiocyanatophenethyl)-1,4,7,10-tetraazacyclododecane.2TFA (28.2TFA)

To a solution of compound (27) (1.25 g, 1.97 mmol) in 0.5 M HCl (10 ml) was carefully added thiophosgene ($CSCl_2$) (4.53 ml, 6.79 g, 59.10 mmol) dissolved in $CHCl_3$ (10 ml). The reaction mixture was stirred at an ambient temperature for 5 hours, and the resultant layers were separated. The aqueous layer was extracted, and the organic $CHCl_3$ layer was washed with water (2×50 ml). The combined aqueous layer was washed with $CHCl_3$ (3×50 ml) to remove the unreacted thiophosgene. Finally, the aqueous layer was lyophilized to obtain a white solid of compound (28) (1.31 g, 98% yield).

Example 9

A Cu (metal)-coordinated chelate, Cu-TE2A-$NO_2$ (compound 30), was prepared from compound (8) obtained according to Example 4 through the route shown in Reaction Scheme 8 below.

<Reaction Scheme 8>

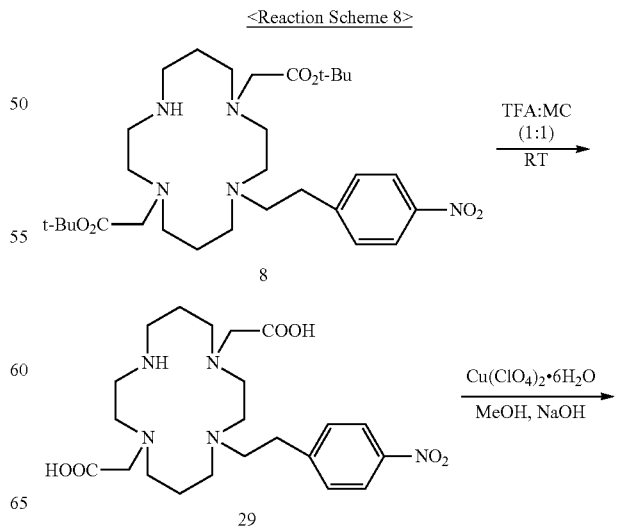

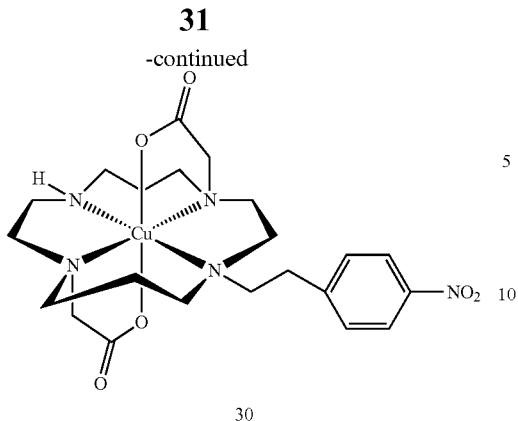

30

Preparation of Cu-TE2A-NO₂ Chelate Compound (30)

Preparation of 1,8-bis-(carboxymethyl)-4-(4'-nitrophenethyl)-1,4,8,11-tetraazacyclotetradecane.2TFA (29.2TFA)

Compound (8) (0.95 g, 1.64 mmol) was dissolved in a mixture of $CF_3CO_2H$ (TFA) and $CH_2Cl_2$ (1:1 (v/v), 35 ml). The resultant mixture was stirred at an ambient temperature for 24 hours. The solvent was evaporated under reduced pressure to give an oily residue, which was then treated with $Et_2O$ to obtain a white solid of compound (29) (1.14 g, 97% yield; calculated as 2 equivalents of TFA for the basic weight). $^1$H NMR (500 MHz, $D_2O$): δ 8.14-8.12 (dd, 2H), 7.49-7.48 (dd, 2H), 3.49 (br s, 4H), 3.45-2.92 (m, 14H), 2.90-2.61 (m, 6H), 1.97-1.91 (m, 4H); $^{13}$C NMR (125 MHz, $D_2O$): δ 176.9, 176.6, 146.7, 144.4, 129.9, 124.0, 56.0, 54.9, 54.4, 52.9, 51.7, 50.5, 47.4, 45.0, 28.0, 22.9, 21.0; HRMS (FAB) calculated for $C_{22}H_{36}N_5O_6$: 466.2666 [(M+H)$^+$], measured value: 466.2661 [(M+H)$^+$].

The mass spectrum of compound (29) is shown in FIG. 1.

Preparation of Cu-TE2A-NO₂ Chelate Compound (30)

To a solution of compound (29) (247 mg, 0.36 mmol) and $Cu(ClO_4)_2.6H_2O$ (132 mg, 0.36 mmol) was added an aqueous 1M NaOH solution (2.16 ml). A clear blue solution thus obtained was heated under reflux for 2 hours. After cooling, the reaction mixture was filtered through a celite pad. The filtered substance was subjected to $Et_2O$ diffusion. The deposited blue crystals were collected and dried to obtain compound (30) (163 mg, 87% yield). HRMS (FAB) calculated for $C_{22}H_{33}CuNaN_5O_6$: 549.1625 [(M+Na)$^+$], measured value: 549.1629 [(M+Na)$^+$]; Visible electron spectrum: λmax (5 M HCl)/561 nm (ε=171 M−1 cm-1)

Figure 2:
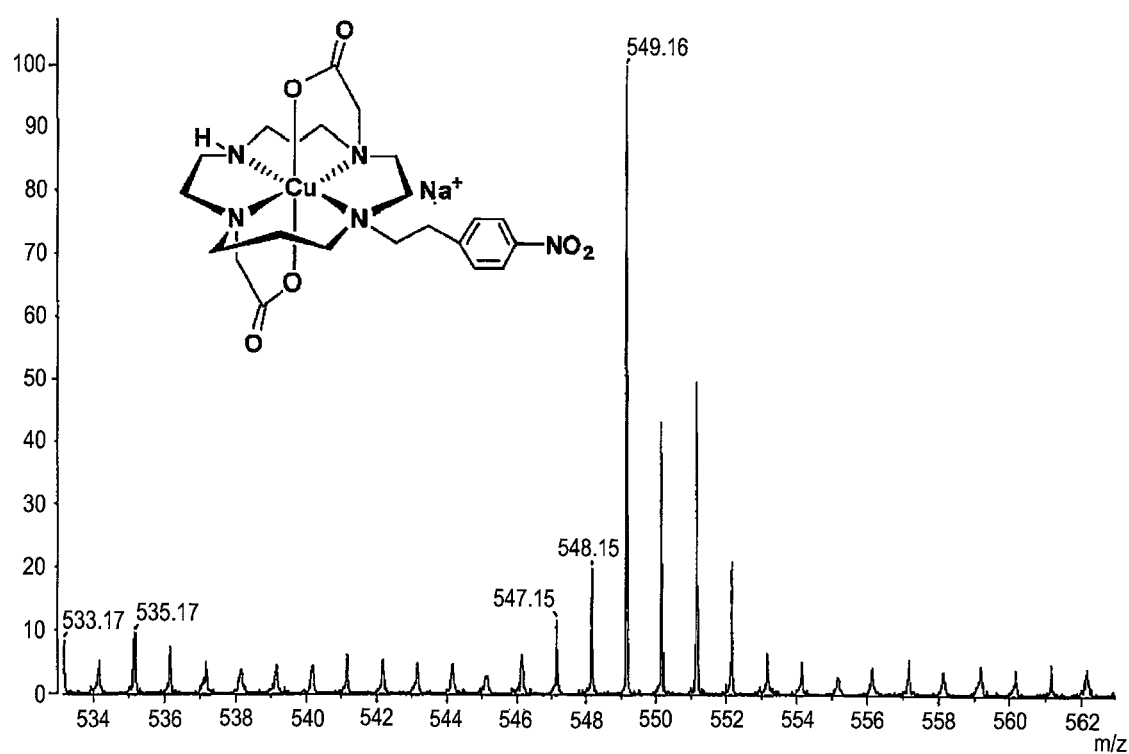
FIG. 2 shows a mass spectrum of Cu-TE2A-$NO_2$ according to an Example.

The mass spectrum of compound (30) is shown in FIG. 2.

Example 10

Acid Decomplexing Experiment of Cu-TE2A-NO₂ Chelate Compound (30)

Figure 3A:
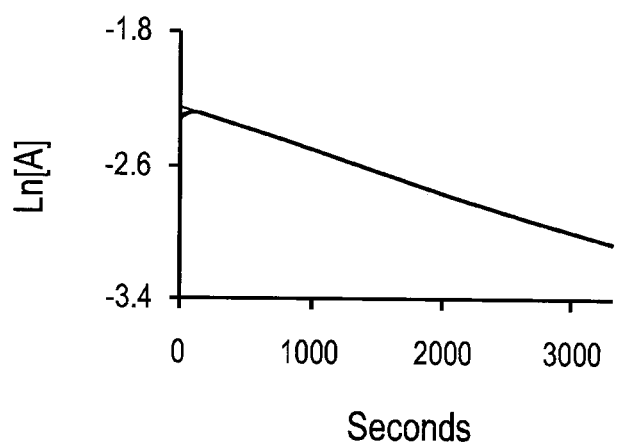
FIGS. 3A and 3B show natural log of absorbance vs. time plots of Cu-TE2A (Comparative Example) and Cu-TE2A-$NO_2$ (Example), respectively from an experiment of acid decomplexation monitored by a UV-VIS spectrophotometer.
Figure 3B:
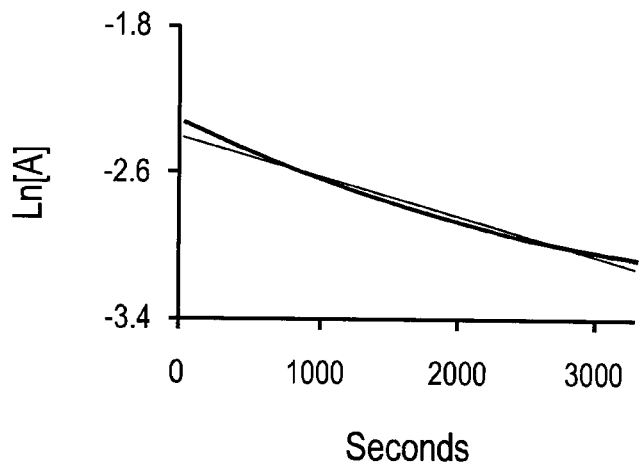

By using a sample of compound (30) in a concentration of 2.2 mmol in 5 M HCl (2 ml), an acid decomplexing experiment was carried out at 90° C., under similar initial conditions. Changes in maximum absorption over time were monitored in a thermostated cell by using a Shimadzu UV-Vis spectrophotometer (UV-1650PC). By utilizing the decreasing absorptivity at the $λ_{max}$ of each spectrum (Cu-TE2A 549 nm, Cu-TE2A-NO₂ 561 nm), the progress of the decomplexing reaction was monitored. From the slope of the linear ln (absorbance) vs. time plots, the half-life was calculated. Each experiment was repeated 2-3 times, and the average half-life was obtained. The measured results are shown in Table 2 and FIGS. 3A and 3B.

Example 11

Electrochemical Experiment for Cu-TE2A-NO₂ Chelate Compound (30)

Figure 4A:
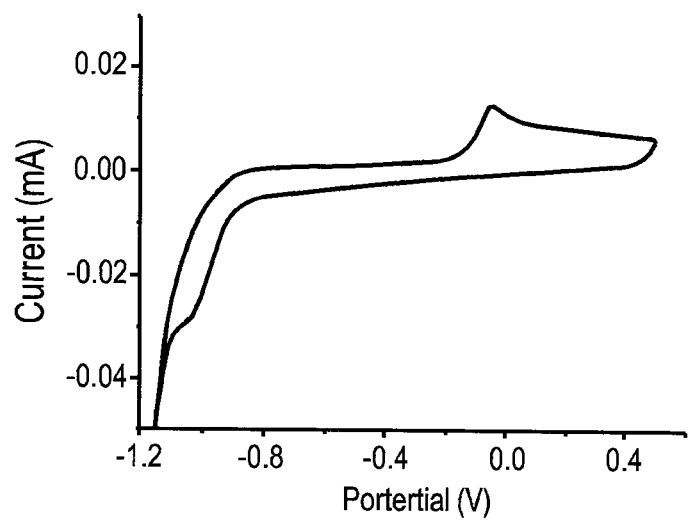
FIGS. 4A and 4B show the results of measured cyclic voltammograms of Cu-TE2A (Comparative Example) and Cu-TE2A-$NO_2$ (Example), respectively.
Figure 4B:
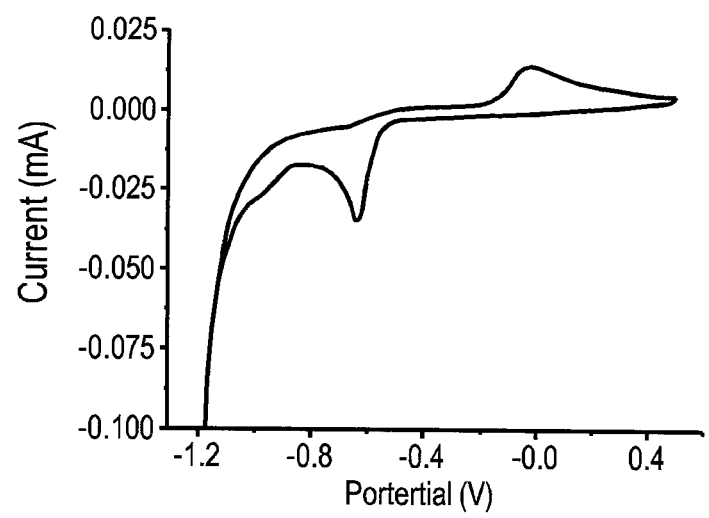

Cyclic voltammetry was carried out by using biological model SP-150 having a 3-electrode structure. The working electrode was made of glassy carbon (diameter=3 mm), the reference electrode Ag/AgCl (saturated KCl), and the counter electrode Pt wire. A sample (2 mM) of compound (30) was operated at a scanning speed of 100 mV/s in a 0.1 M aqueous sodium acetate solution adjusted to pH 7.0 with glacial acetic acid. From the solution, oxygen was removed by bubbling Ar for 30 minutes. During the measurement, the system was maintained under Ar atmosphere. The measured results are shown in Table 2 and FIGS. 4A and 4B.

TABLE 2

| Sample | Half-life (5M HCl, 90° C.) | $E_{red}$ (V) for Ag/AgCl |
|---|---|---|
| Cu-TE2A | 46.2 min | −1.05 (irrev) |
| Compound (30) | 47.7 min | −0.98 (irrev) |

The kinetic inertness and reduction potential of compound (30) were nearly identical to those of Cu-TE2A. Based on those results, it can be recognized that the introduction of a third orthogonal pendant arm having a NCS functional group for conjugation with a peptide or an antibody to the TE2A backbone does not inhibit higher kinetic inertness than a TETA (half-life: 4.7 min) analogue that has been most conventionally used.

Example 12

From compound (5) according to Example 2, TE2A-mono-Me (compound 32), to which a methyl group was introduced, was prepared via the route shown in Reaction Scheme 9 below.

<Reaction Scheme 9>

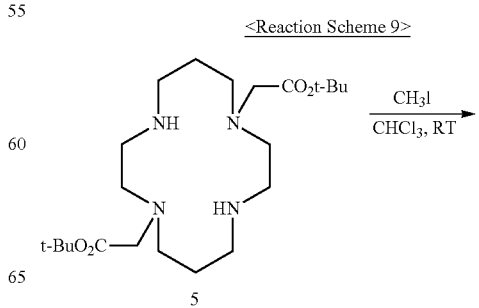

5

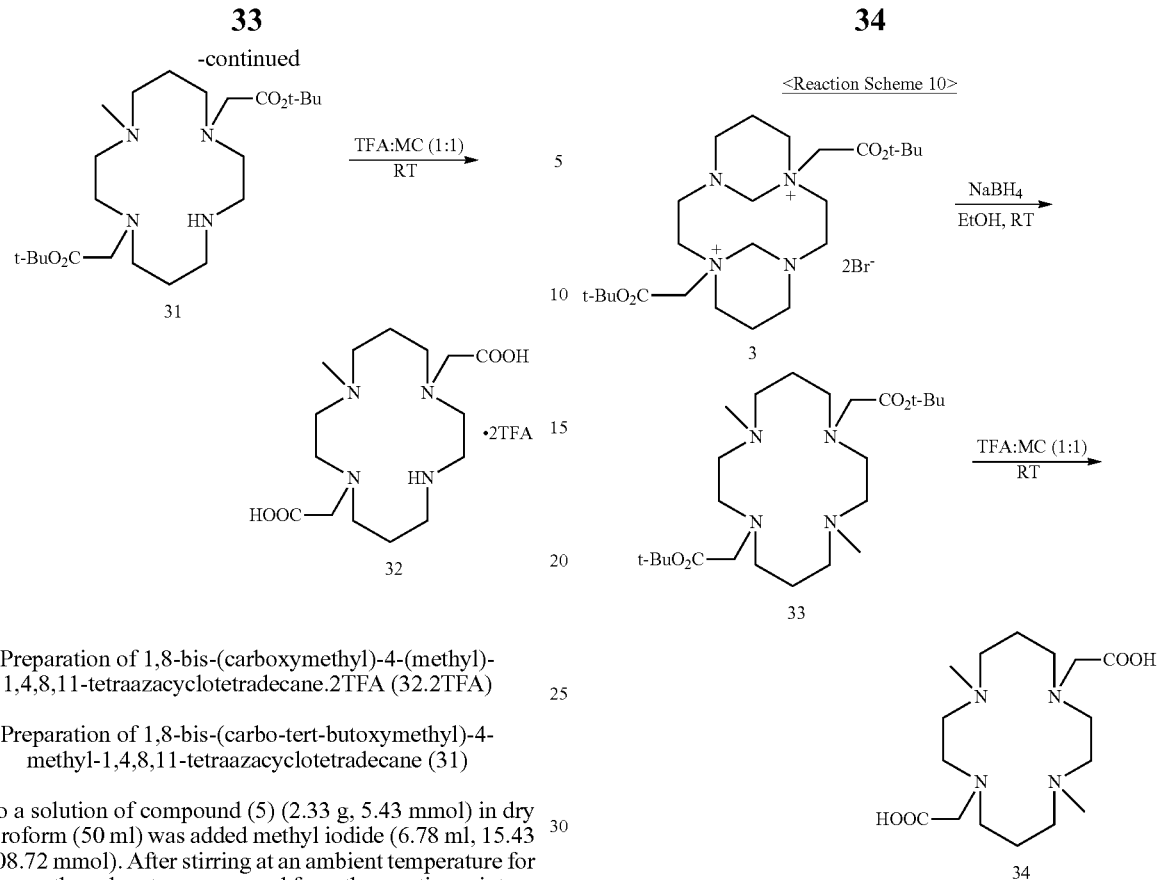

Preparation of 1,8-bis-(carboxymethyl)-4-(methyl)-1,4,8,11-tetraazacyclotetradecane.2TFA (32.2TFA)

Preparation of 1,8-bis-(carbo-tert-butoxymethyl)-4-methyl-1,4,8,11-tetraazacyclotetradecane (31)

To a solution of compound (5) (2.33 g, 5.43 mmol) in dry chloroform (50 ml) was added methyl iodide (6.78 ml, 15.43 g, 108.72 mmol). After stirring at an ambient temperature for 24 hours, the solvent was removed from the reaction mixture under reduced pressure. The residue was purified via column chromatography on silica using chloroform/isopropyl amine (20:2) as an eluent, to obtain compound (31) as a clear oil (2.41 g, 84% yield). $^1$H NMR (500 MHz, CDCl$_3$): δ 3.27-3.25 (dd, 4H), 2.84-2.43 (m, 16H), 2.16 (s, 3H), 1.73-1.59 (m, 4H), 1.45 (s, 18H); $^{13}$C NMR (125 MHz, CDCl$_3$): δ 170.94, 170.68, 80.57, 55.99, 55.93, 54.80, 53.77, 53.40, 52.26, 50.11, 48.34, 47.41, 47.17, 41.88, 28.18, 25.59, 25.00; HRMS (FAB) calculated for C$_{23}$H$_{47}$N$_4$O$_4$: 443.3597 [(M+H)$^+$], measured value: 443.3600 [(M+H)$^+$].

Figure 5:
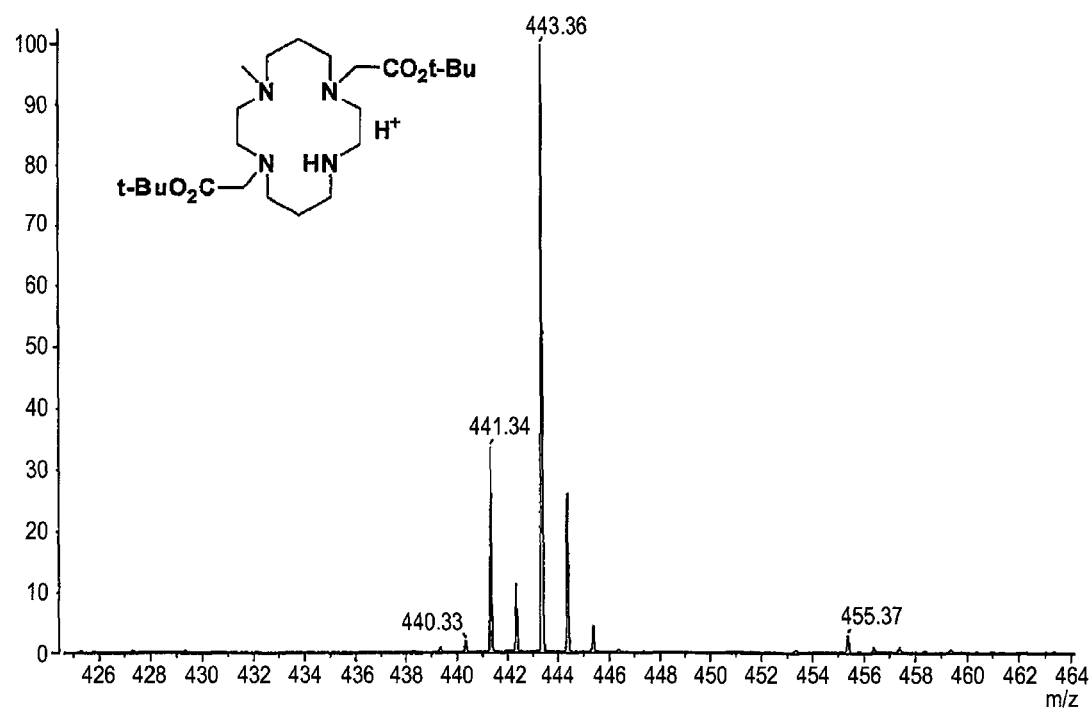
FIG. 5 shows a mass spectrum of TE2A-mono-methyl to which tert-butyl has been introduced as a protective group for carboxylic acid, according to an Example.

The mass spectrum of compound (31) is shown in FIG. 5.

Preparation of 1,8-bis-(carboxymethyl)-4-(methyl)-1,4,8,11-tetraazacyclotetradecane.2TFA (32.2TFA)

Compound (31) (1.56 g, 3.52 mmol) was dissolved in a mixture of CF$_3$CO$_2$H (TFA) and CH$_2$Cl$_2$ (1:1 (v/v), 60 ml). The resultant mixture was stirred at an ambient temperature for 24 hours. The solvent was removed under reduced pressure to give an oily residue, which was then treated with Et$_2$O to obtain a white solid of compound (32) (1.95 g, 99% yield; calculated as 2 equivalents of TFA for the basic weight). $^1$H NMR (500 MHz, D$_2$O): δ 3.60-3.05 (m, 13H), 2.98-2.641 (m, 10H), 2.12-1.82 (m, 4H); $^{13}$C NMR (125 MHz, D$_2$O): δ 177.20, 175.83, 56.71, 55.87, 54.50, 54.22, 52.92, 48.268, 44.94, 41.15, 22.61, 20.64; HRMS (FAB) calculated for C$_{15}$H$_{31}$N$_4$O$_4$: 331.2345 [(M+H)$^+$], measured value: 331.2347 [(M+H)$^+$].

Figure 6:
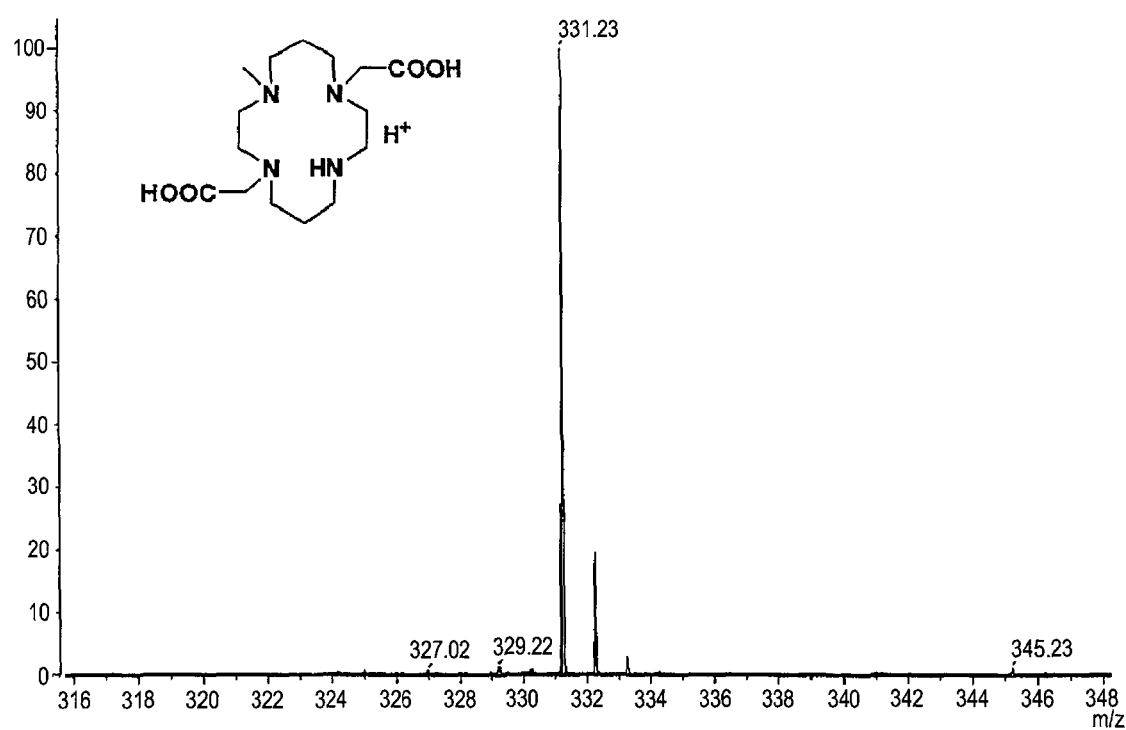
FIG. 6 shows a mass spectrum of TE2A-mono-methyl from which the protective group for carboxylic acid has been removed, according to an Example.

The mass spectrum of compound (32) is shown in FIG. 6.

Example 13

From compound (3) according to Example 1, TE2A-di-Me (compound 34), to which two methyl groups were introduced, was prepared via the route shown in Reaction Scheme 10 below.

Preparation of 1,8-bis-(carboxymethyl)-4,11-bis-(methyl)-1,4,8,11-tetraazacyclotetradecane (34)

Preparation of 1,8-bis-(carbo-tert-butoxymethyl)-4,11-bis-(methyl)-1,4,8,11-tetraazacyclotetradecane (33)

To a solution of compound (3) (3.06 g, 7.14 mmol) in absolute ethanol (80 ml) was added NaBH$_4$ (8.10 g, 214.2 mmol). After stirring at an ambient temperature for 24 hours, the solvent was removed under reduced pressure. The residue was dissolved in CH$_2$Cl$_2$ (150 ml), and filtered. The filtered substance was dried, and the residue was purified via column chromatography on silica using chloroform/isopropyl amine (20:2) as an eluent, to obtain compound (33) as a clear oil (3.05 g, 94% yield). $^1$H NMR (500 MHz, CDCl$_3$): δ 3.23 (s, 4H), 2.80-2.62 (m, 8H), 2.43 (br s, 8H), 2.19 (s, 6H), 1.68-1.58 (m, 4H), 1.42 (s, 18H); $^{13}$C NMR (125 MHz, CDCl$_3$): δ 170.89, 80.61, 56.50, 54.51, 53.91, 51.00, 50.55, 43.29, 28.15, 24.66; HRMS (FAB) calculated for C$_{24}$H$_{49}$N$_4$O$_4$: 457.3754 [(M+H)$^+$], measured value: 457.3756 [(M+H)$^+$].

Figure 7:
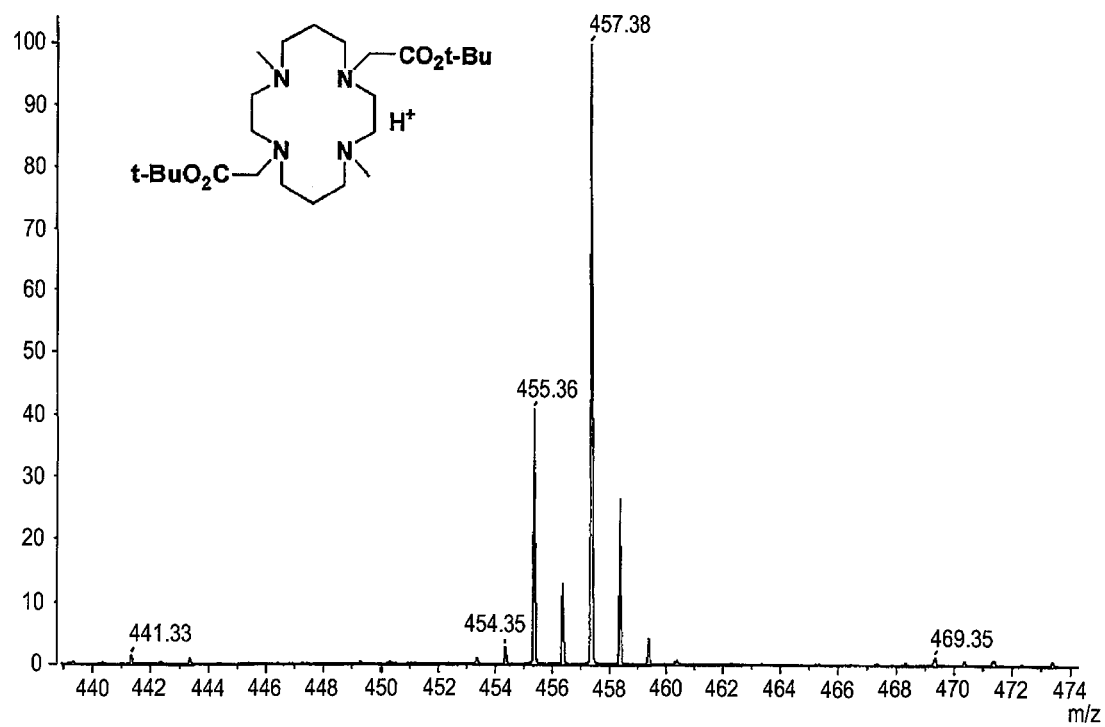
FIG. 7 shows a mass spectrum of TE2A-di-methyl to which tert-butyl has been introduced as a protective group for carboxylic acid, according to an Example.

The mass spectrum of compound (33) is shown in FIG. 7.

Preparation of 1,8-bis-(carboxymethyl)-4,11-bis-(methyl)-1,4,8,11-tetraazacyclotetradecane (34)

Compound (33) (1.46 g, 3.19 mmol) was dissolved in a mixture of CF$_3$CO$_2$H (TFA) and CH$_2$Cl$_2$ (1:1 (v/v), 50 ml). The resultant mixture was stirred at an ambient temperature for 24 hours. The solvent was removed under reduced pressure to give an oily residue, which was then treated with Et₂O to obtain a white solid of compound (34) (1.09 g, 99% yield). HRMS (FAB) calculated for $C_{16}H_{33}N_4O_4$: 345.2502 [(M+H)⁺], measured value: 345.2506 [(M+H)⁺].

Figure 8:
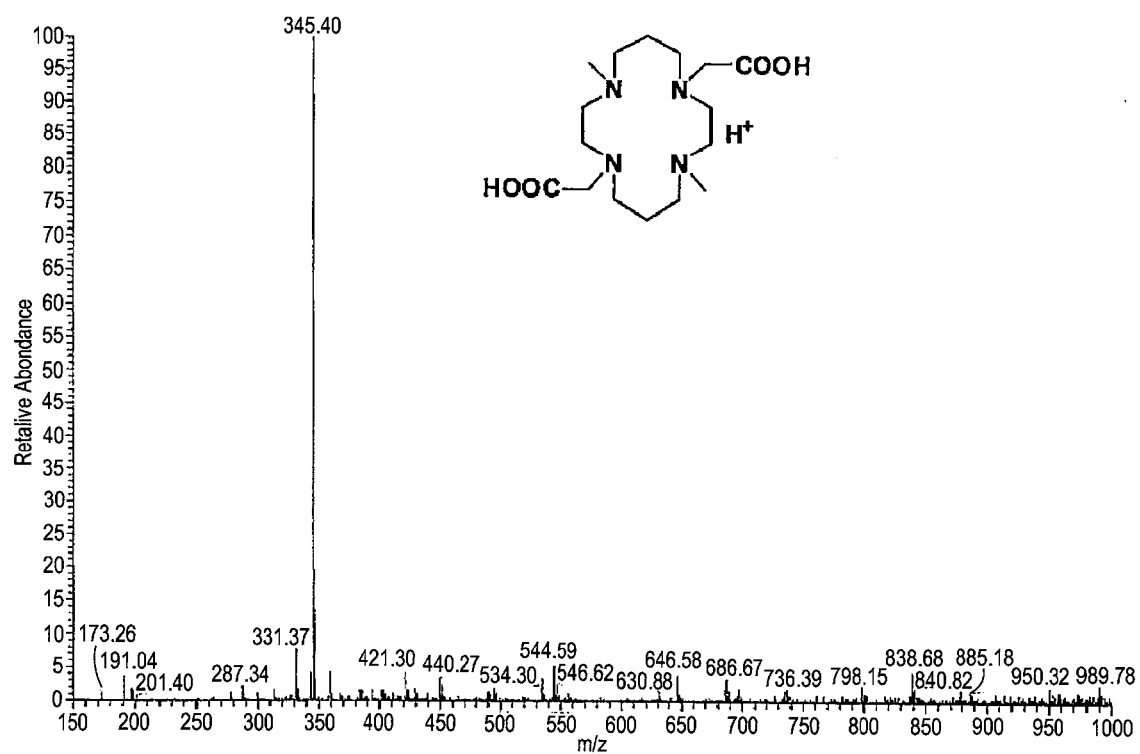
FIG. 8 shows a mass spectrum of TE2A-di-methyl from which the protective group for carboxylic acid has been removed, according to an Example.

The mass spectrum of compound (34) is shown in FIG. 8.

As shown in Example 13, according to the present invention, compounds in which substituents have been symmetrically introduced to amine, such as compound (34), as well as compounds in which substituents have been asymmetrically introduced to amine, such as compound (32), can be synthesized.

Example 14

A Cu-chelated compound, Cu-TE2A-mono-Me (compound 35), was prepared from compound (32) obtained according to Example 12 via the route shown in Reaction Scheme 11 below.

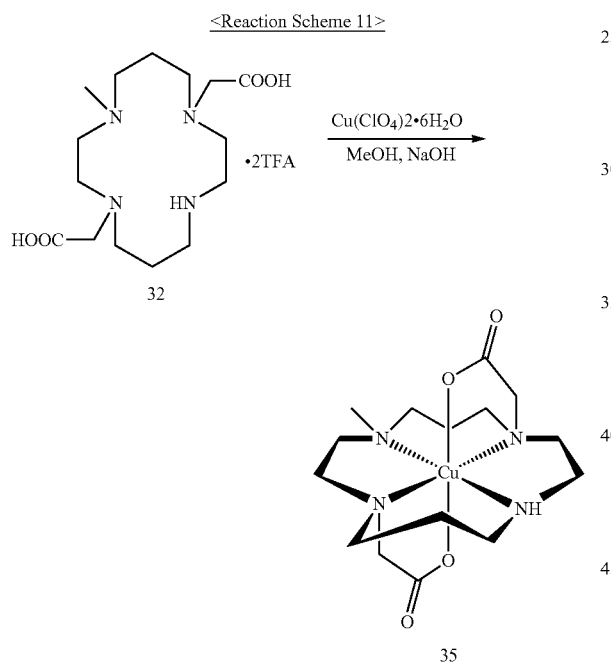

Preparation of Cu-TE2A-mono-Me Chelate Compound (35)

To a solution of compound (32) (265 mg, 0.47 mmol) and Cu(ClO₄)₂.6H₂O (176 mg, 0.47 mmol) in 22 ml of methanol was added an aqueous 1M NaOH solution (2.82 ml). A blue solution thus obtained was heated under reflux for 2 hours. After cooling, the reaction mixture was filtered through a celite pad. The filtered substance was subjected to Et₂O diffusion. The deposited blue crystals were collected and dried to obtain compound (35) (166 mg, 89% yield). HRMS (FAB) calculated for $C_{15}H_{28}CuNaN_4O_4$: 414.1304 [(M+Na)⁺], measured value: 414.1302 [(M+Na)⁺].

Figure 9:
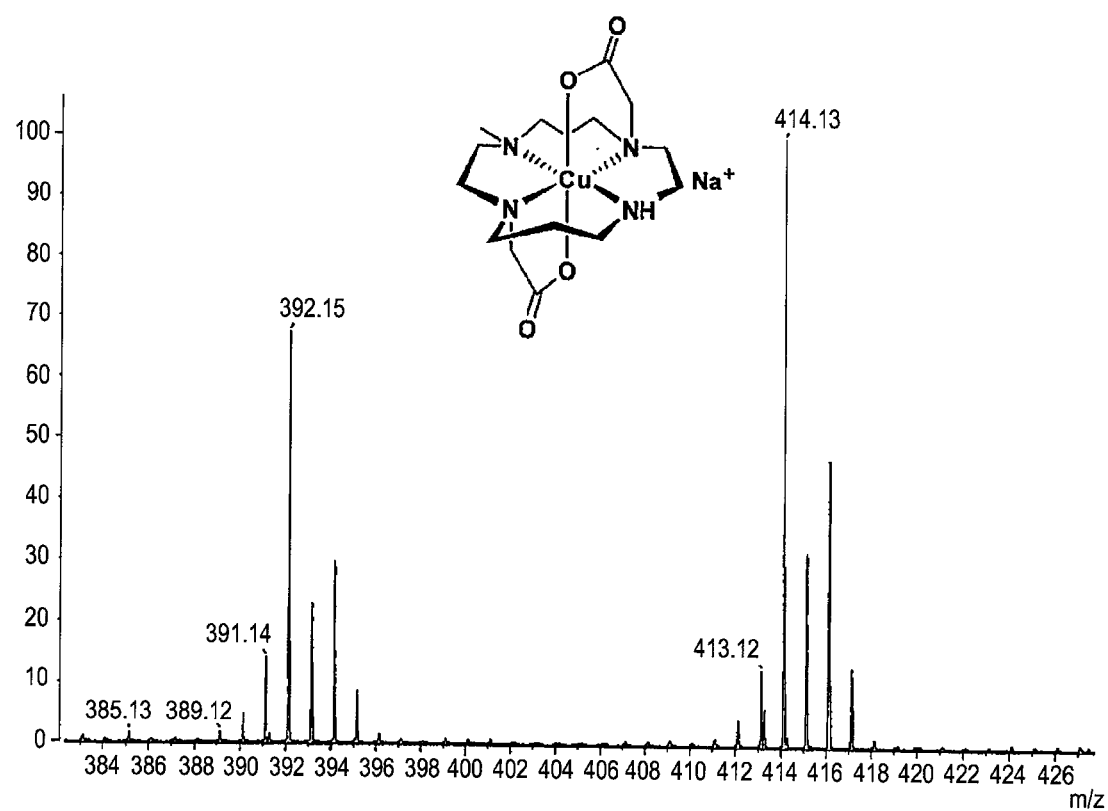
FIG. 9 shows a mass spectrum of Cu-TE2A-mono-methyl according to an Example.

The mass spectrum of compound (35) is shown in FIG. 9.

Example 15

A Cu-chelated compound, Cu-TE2A-di-Me (compound 36), was prepared from compound (34) obtained according to Example 13 via the route shown in Reaction Scheme 12 below.

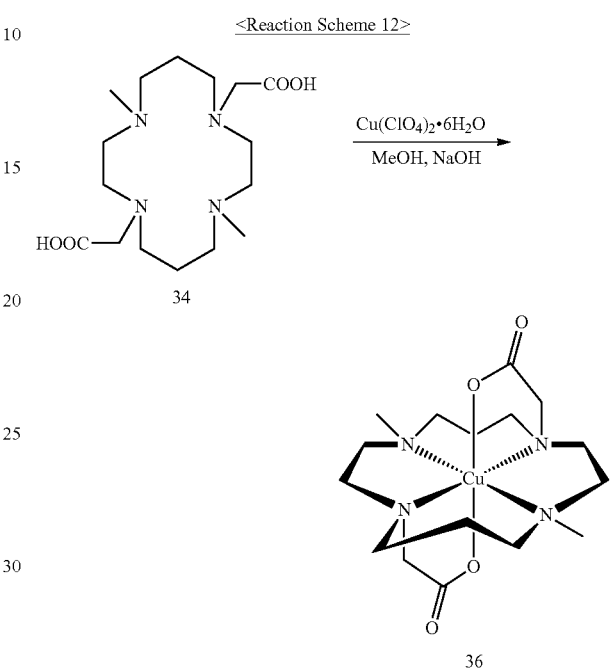

Preparation of Cu-TE2A-di-Me Chelate Compound (36)

To a solution of compound (34) (253 mg, 0.73 mmol) and Cu(ClO₄)₂.6H₂O (272 mg, 0.73 mmol) in 25 ml of methanol was added an aqueous 1M NaOH solution (4.38 ml). A blue solution thus obtained was heated under reflux for 2 hours. After cooling, the reaction mixture was filtered through a celite pad. The filtered substance was subjected to Et₂O diffusion. The deposited blue crystals were collected and dried to obtain compound (36) (253 mg, 85% yield). HRMS (FAB) calculated for $C_{16}H_{30}CuNaN_4O_4$: 428.1461 [(M+Na)⁺], measured value: 428.1462 [(M+Na)⁺].

Figure 10:
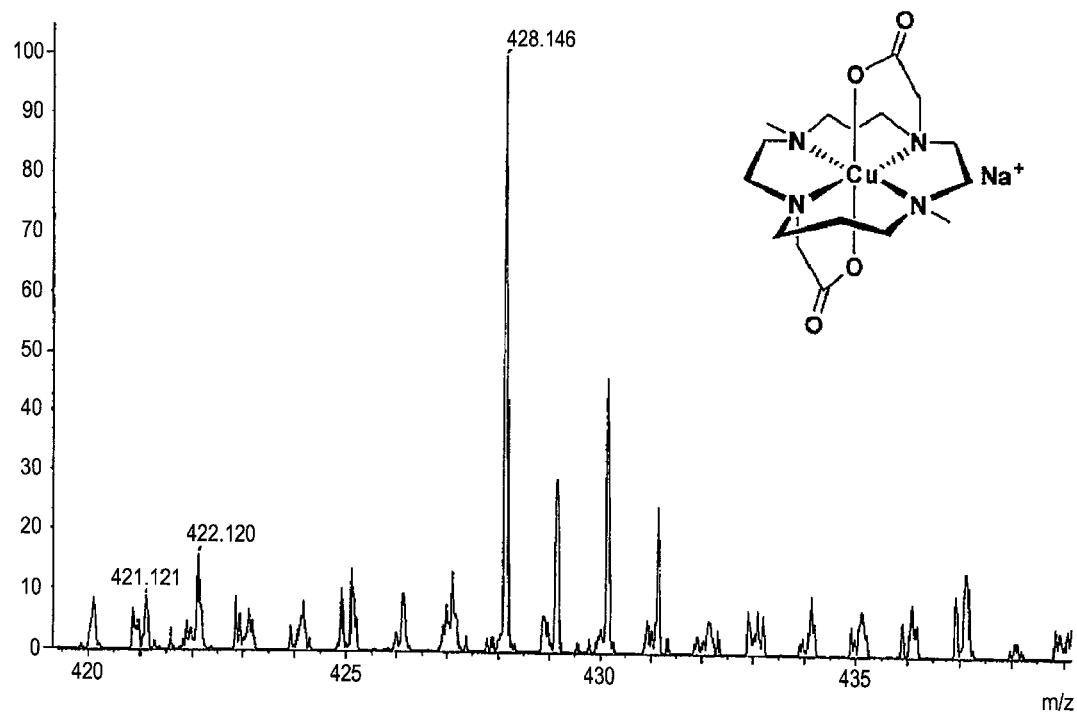
FIG. 10 shows a mass spectrum of Cu-TE2A-di-methyl according to an Example.

The mass spectrum of compound (36) is shown in FIG. 10.

Example 16

A metal chelating conjugate compound can be prepared by binding BFC to a bioactive molecule such as a peptide, and chelating the metal, or by binding a bioactive molecule such as a peptide to a metal-BFC chelate (which was prepared in advance). In the present Example, [⁶⁴Cu-TE2A-c(RGDyK)] metal chelating conjugate compound (38) was prepared by binding TE2A-NCS compound (14) (prepared according to the Example described above) via the route shown in Reaction Scheme 13 to a peptide c(RGDyK) to provide a conjugate compound, and chelating the metal ⁶⁴Cu.

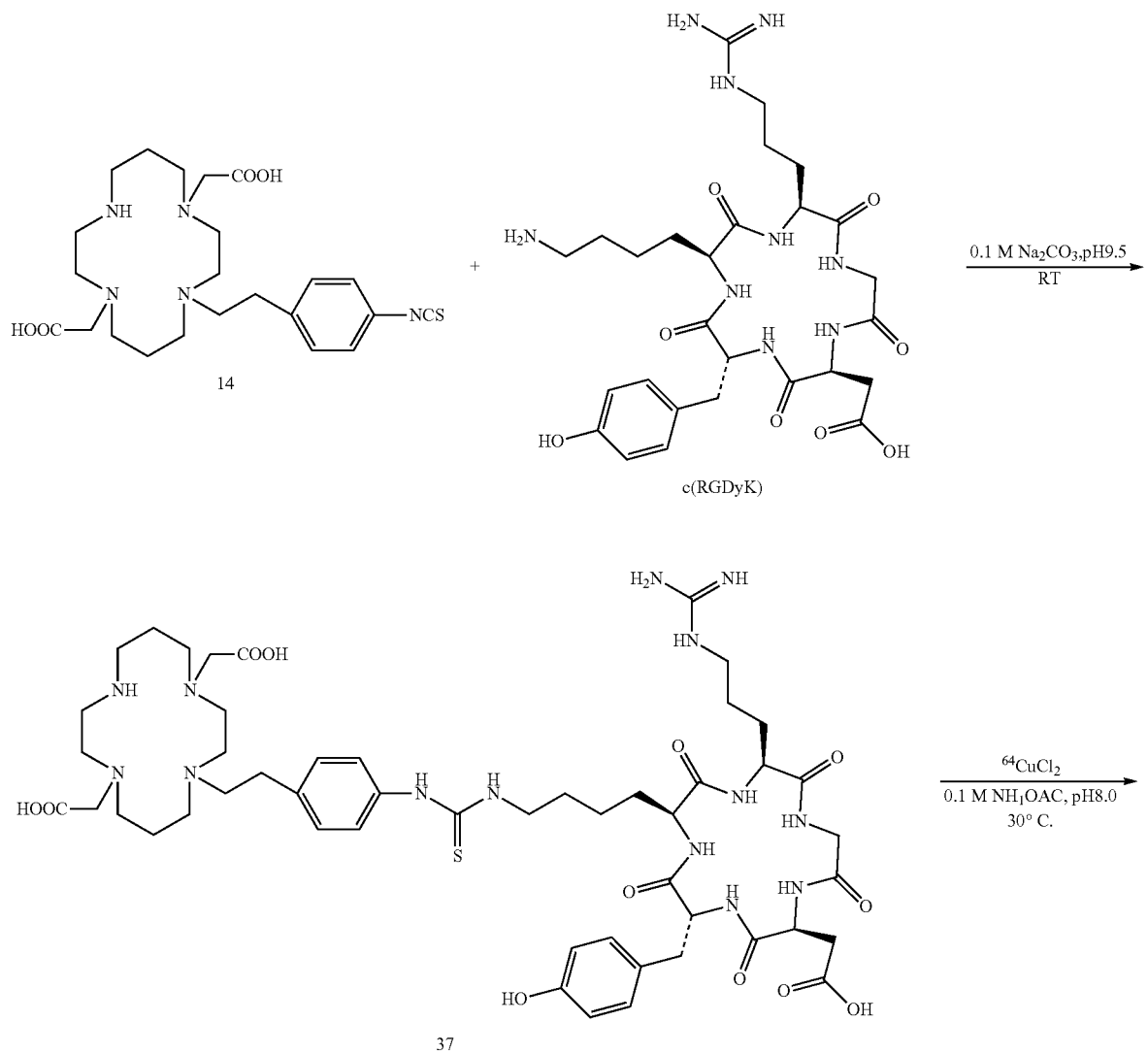
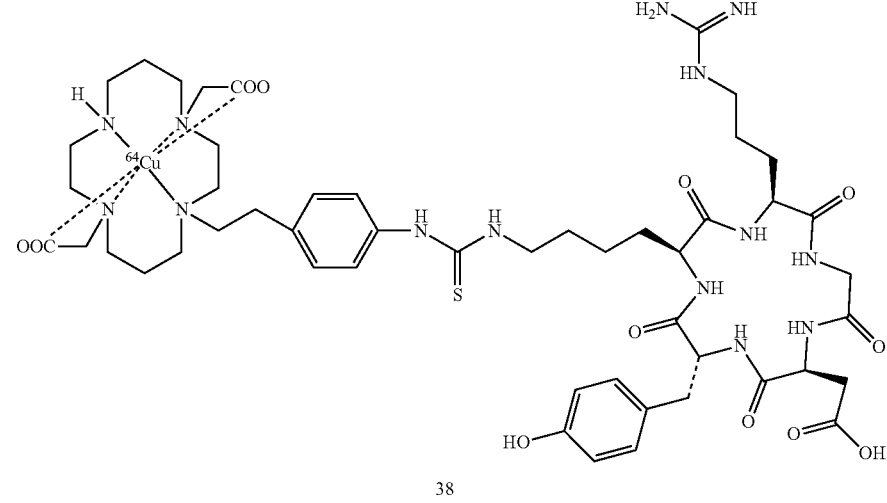

Preparation of [$^{64}$Cu-TE2A-c(RGDyK)] metal chelating conjugate compound (38)

Preparation of a conjugate compound of TE2A-NCS and peptide c(RGDyK) (37)

A solution of TE2A-NCS compound (14) (495 nmol, 2.36 mg) was combined with peptide c(RGDyK) (165 nmol, 1.02 mg) in 0.1 M Na$_2$CO$_3$ buffer (pH 9.5). Under a light-shielded environment, the mixture was stirred at an ambient temperature for 22 hours, and subjected to semi-preparative high performance liquid chromatography (HPLC) (Agilent preparative column C18; 5 μm, 21.2×100 mm; flow rate 3 ml/min, mobile phase: starting with 95% solvent A [aqueous 0.1% TFA solution] and 5% solvent B [0.1% TFA in MeCN] [0-2 min] to 35% solvent A and 65% solvent B at 32 min), to isolate the c(RGDyK) peptide conjugated to TE2A. At the 21.7 min retention time on the HPLC, visible TE2A-c(RGDyK) was collected and lyophilized to provide TE2A-c(RGDyK) compound (37) as a white powder (82% yield). On an analytical HPLC column (Vydac TP C18; 3 μm, 4.6×100 mm; flow rate 1 ml/min, mobile phase: 0.1% TFA/H$_2$O (solvent A) and 0.1% TFA/MeCN (solvent B), and a gradient elution of 1% B to 70% B in 20 minutes), the retention time of TE2A-c(RGDyK) compound (37) was 12.8 min. The purified TE2A-c(RGDyK) compound (37) was identified by using a jet-type mass analyzer (m/z calculated for C$_{50}$H$_{77}$N$_{14}$O$_{12}$S was 1097.55, m/z affirmed for [MH]$^+$ and [MH$_2$]$^{+2}$: 1097.58 and 549.62, respectively).

Figure 11:
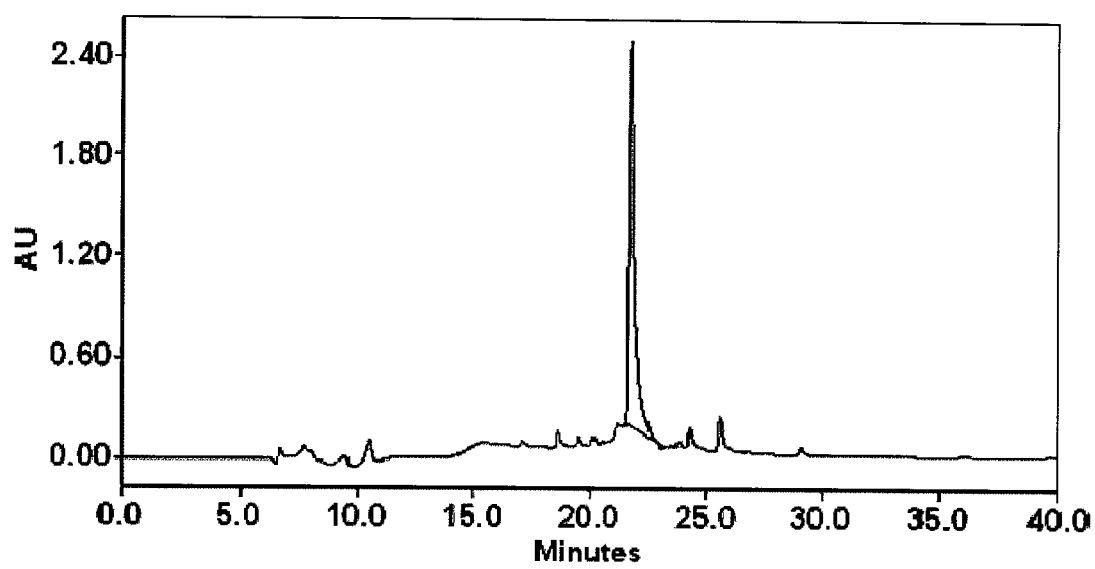
FIG. 11 shows a semi-preparative HPLC chromatogram of TE2A-c(RGDyK) according to an Example.
Figure 12:
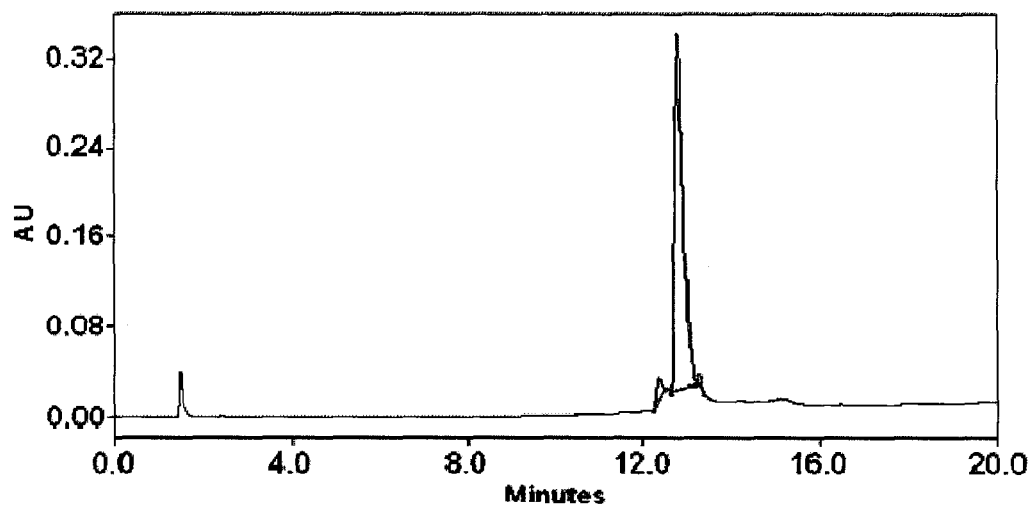
FIG. 12 shows a HPLC chromatogram for analysis of TE2A-c(RGDyK) according to an Example.
Figure 13:
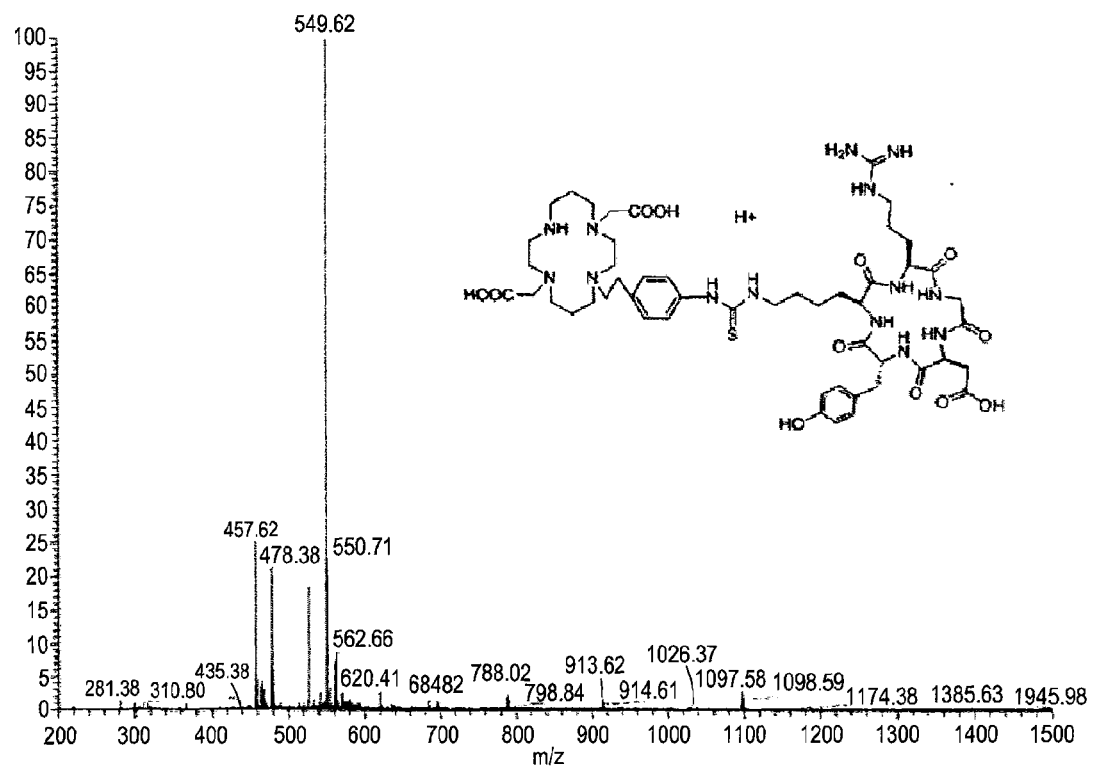
FIG. 13 shows a mass spectrum of TE2A-c(RGDyK) according to an Example.

FIG. 11 shows a chromatogram of TE2A-c(RGDyK) compound (37) on semi-preparative HPLC, while FIG. 12 shows a chromatogram of TE2A-c(RGDyK) compound (37) on analytical HPLC. FIG. 13 shows a mass spectrum of TE2A-c(RGDyK) compound (37).

Preparation of [$^{64}$Cu-TE2A-c(RGDyK)] metal chelating conjugate compound (38)

To TE2A-c(RGDyK) compound (37) (2 μg) in 100 μl of 0.1 M NH$_4$OAc buffer (pH 8.0) was added $^{64}$Cu (0.52 mCi) in 100 μl of 0.1 M NH$_4$OAc buffer (pH 8.0). The mixture was reacted at 30° C. for 5 minutes. The reaction was monitored through radio-TLC using Whatman MKC18F thin layer chromatography (TLC) plate developed by 10% NH$_4$OAc/methanol (30:70) [R$_f$ of $^{64}$Cu-TE2A-c(RGDyK)=0.9]. The $^{64}$Cu-labeled peptide was further purified via reverse-phase (RP) HPLC [Vydac TP C18; 3 μm, 4.6×100 mm; flow rate 1 ml/min, mobile phase: 0.1% TFA/H$_2$O (solvent A) and 0.1% TFA/MeCN (solvent B), and a gradient elution of 1% B to 70% B in 20 minutes]. After collecting $^{64}$Cu-TE2A-c(RGDyK) compound (38) (retention time [t$_R$]: 13.8 min) by using 12 ml of the HPLC solvent, the solvent was evaporated and the residue was recovered with PBS (phosphate-buffered saline). Then the recovered $^{64}$Cu-TE2A-c(RGDyK) compound (38) was filtered through a 0.22 μm Millipore filter, and transferred to a sterile bottle for animal tests.

Figure 14:
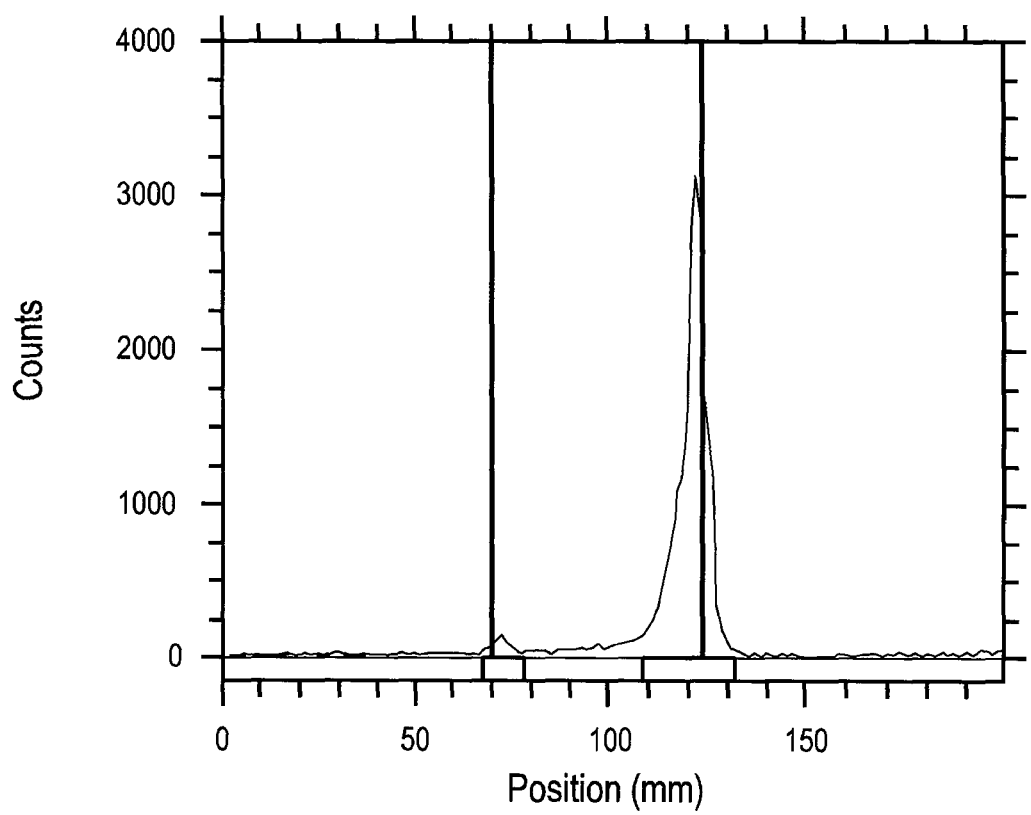
FIG. 14 shows a radio-TLC chromatogram of $^{64}Cu$-TE2A-c(RGDyK) metal chelating conjugate compound in which TE2A-c(RGDyK) has been labeled with $^{64}Cu$, according to an Example.
Figure 15:
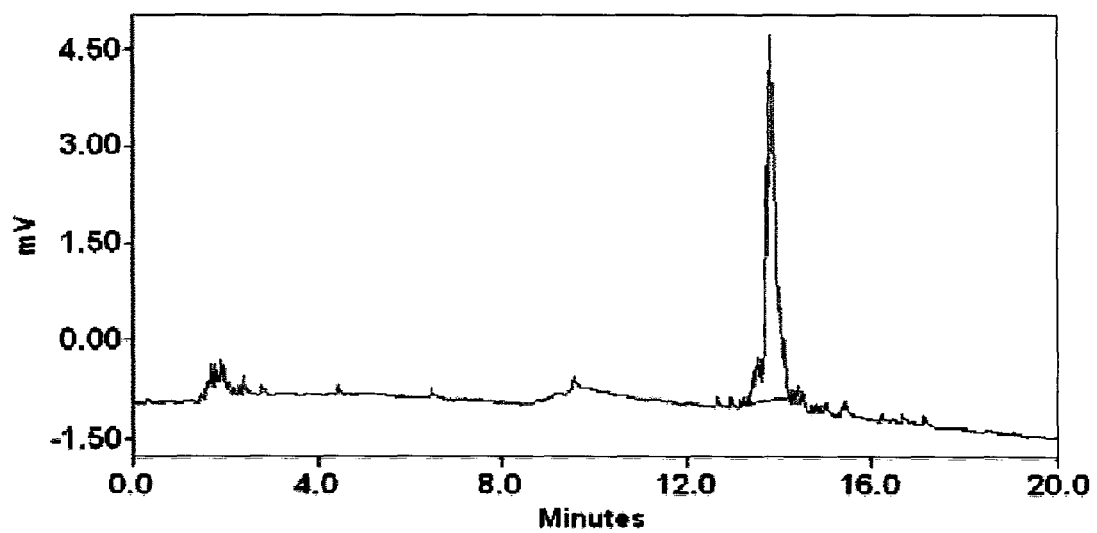
FIG. 15 shows a HPLC radio chromatogram for analysis of $^{64}Cu$-TE2A-c(RGDyK) metal chelating conjugate compound in which TE2A-c(RGDyK) has been labeled with $^{64}Cu$, according to an Example.
Figure 16:
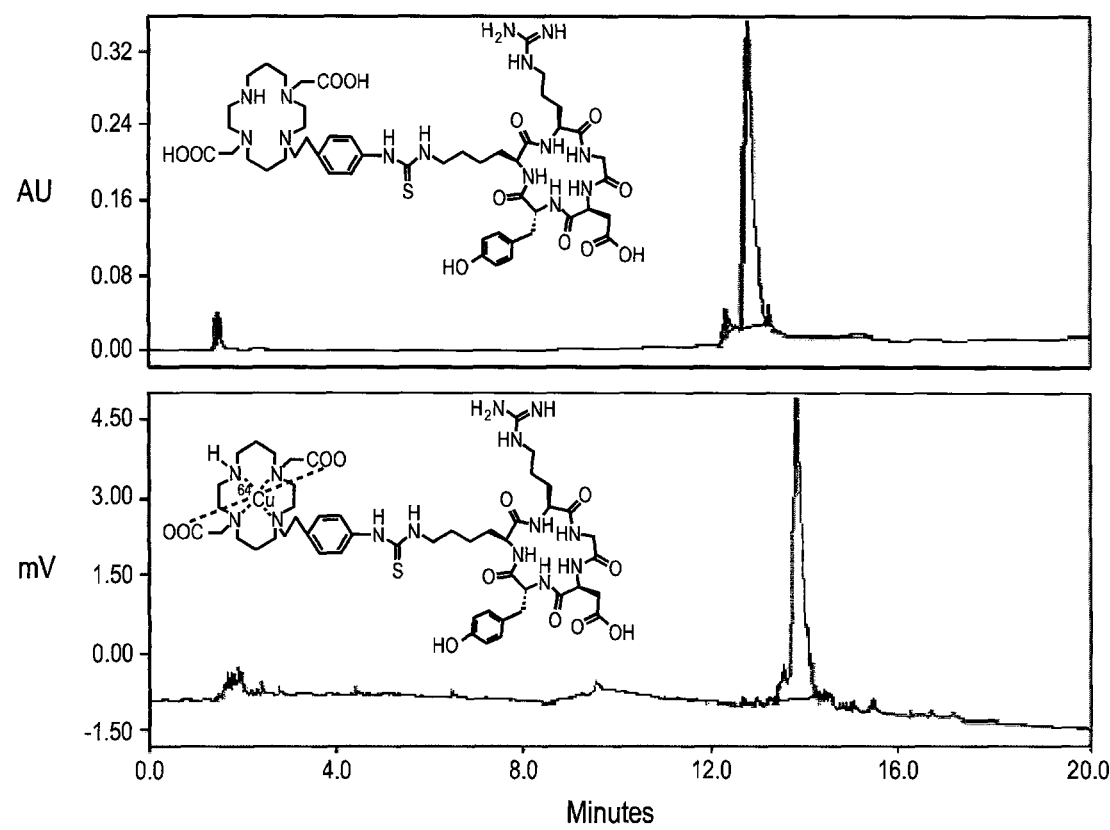
FIG. 16 shows HPLC chromatograms for analysis of both TE2A-c(RGDyK) conjugate compound according to an Example and of $^{64}Cu$-TE2A-c(RGDyK) metal chelating conjugate compound (in which TE2A-c(RGDyK) has been labeled with $^{64}Cu$), respectively, in order to confirm the preparation of the metal chelating conjugate compound.

FIG. 14 shows a radio-TLC chromatogram of $^{64}$Cu-TE2A-c(RGDyK) compound (38), while FIG. 15 shows a radio chromatogram of $^{64}$Cu-TE2A-c(RGDyK) compound (38) on analytical HPLC. FIG. 16 simultaneously shows TE2A-c(RGDyK) compound (37) and $^{64}$Cu-TE2A-c(RGDyK) compound (38) on analytical HPLC, in order to confirm the preparation of the metal chelating conjugate.

Example 17

Experiment for In Vivo Distribution of $^{64}$Cu-TE2A-c(RGDyK)

Figure 17:
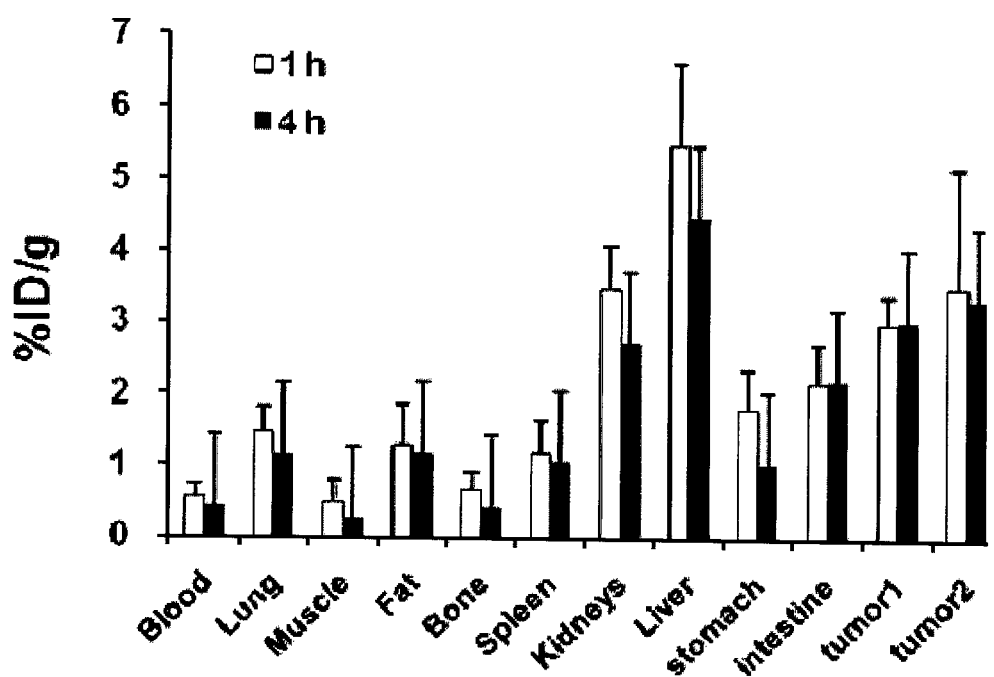
FIG. 17 shows the result of the in vivo distribution test of $^{64}Cu$-TE2A-c(RGDyK) metal chelating conjugate compound in which TE2A-c(RGDyK) has been labeled with $^{64}Cu$, according to an Example.

Compound $^{64}$Cu-TE2A-c(RGDyK) (38) (10 μCi) in PBS (120 μl) was injected to the tails of female nude mice to which U87MG tumor had been transplanted. Two groups were examined at two time points [n=4 per group at 1 hr and 4 hr post injection (pi)]. The subject animals were sacrificed, and the relevant tissues and organs were removed and weighed. A dosimetric procedure was carried out by using a gamma-counter. The calculations were performed by comparing with a reference value of which the percentage of injected amount per gram was known. The test results (% ID/g±SD, n=4) are shown in Table 3 and FIG. 17.

TABLE 3

| Tissue | 1 hr | 4 hr |
| --- | --- | --- |
| Blood | 0.55 ± 0.18 | 0.43 ± 0.09 |
| Lung | 1.46 ± 0.34 | 1.14 ± 0.17 |
| Muscle | 0.49 ± 0.30 | 0.24 ± 0.11 |
| Fat | 1.28 ± 0.55 | 1.15 ± 1.08 |
| Bone | 0.66 ± 0.23 | 0.41 ± 0.06 |
| Spleen | 1.17 ± 0.46 | 1.04 ± 0.46 |
| Kidney | 3.47 ± 0.61 | 2.71 ± 0.45 |
| Liver | 5.45 ± 1.14 | 4.45 ± 0.65 |
| Stomach | 1.78 ± 0.55 | 1.03 ± 0.39 |
| Intestine | 2.14 ± 0.53 | 2.17 ± 0.62 |
| Tumor 1 | 2.98 ± 0.39 | 3.01 ± 1.00 |
| Tumor 2 | 3.49 ± 1.67 | 3.32 ± 0.49 |

Example 18

Micro PET Image Analysis of $^{64}$Cu-TE2A-c(RGDyK)

PET scans and image analyses of the present Example were carried out by using a Micro PET R4 rodent model scanner. The imaging study was carried out with a female nude mouse bearing 41-days U87MG tumors. Compound $^{64}$Cu-TE2A-c(RGDyK) (38) (205 μCi) was injected to the tail of the mouse. After 1 hour, 4 hours, 1 day, 2 days and 3 days after injection, the mouse was anesthetized with 1-2% isoflurane. The mouse was fixed lying its face down, and an image was obtained. The images were reconstituted by an algorithm of 2-dimensional ordered subsets expectation maximization (OSEM), without any correction of attenuation or scattering.

Figure 18:
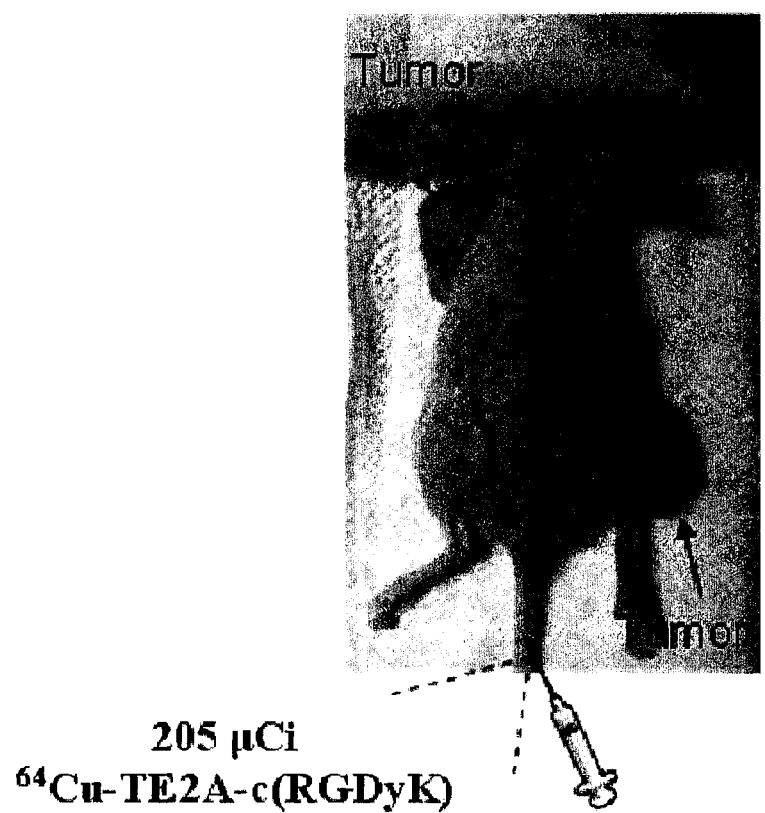
FIG. 18 illustrates administering $^{64}Cu$-TE2A-c(RGDyK) metal chelating conjugate compound in which TE2A-c (RGDyK) has been labeled with $^{64}Cu$, according to an Example, to a female nude mouse having U87MG tumor cells.
Figure 19:
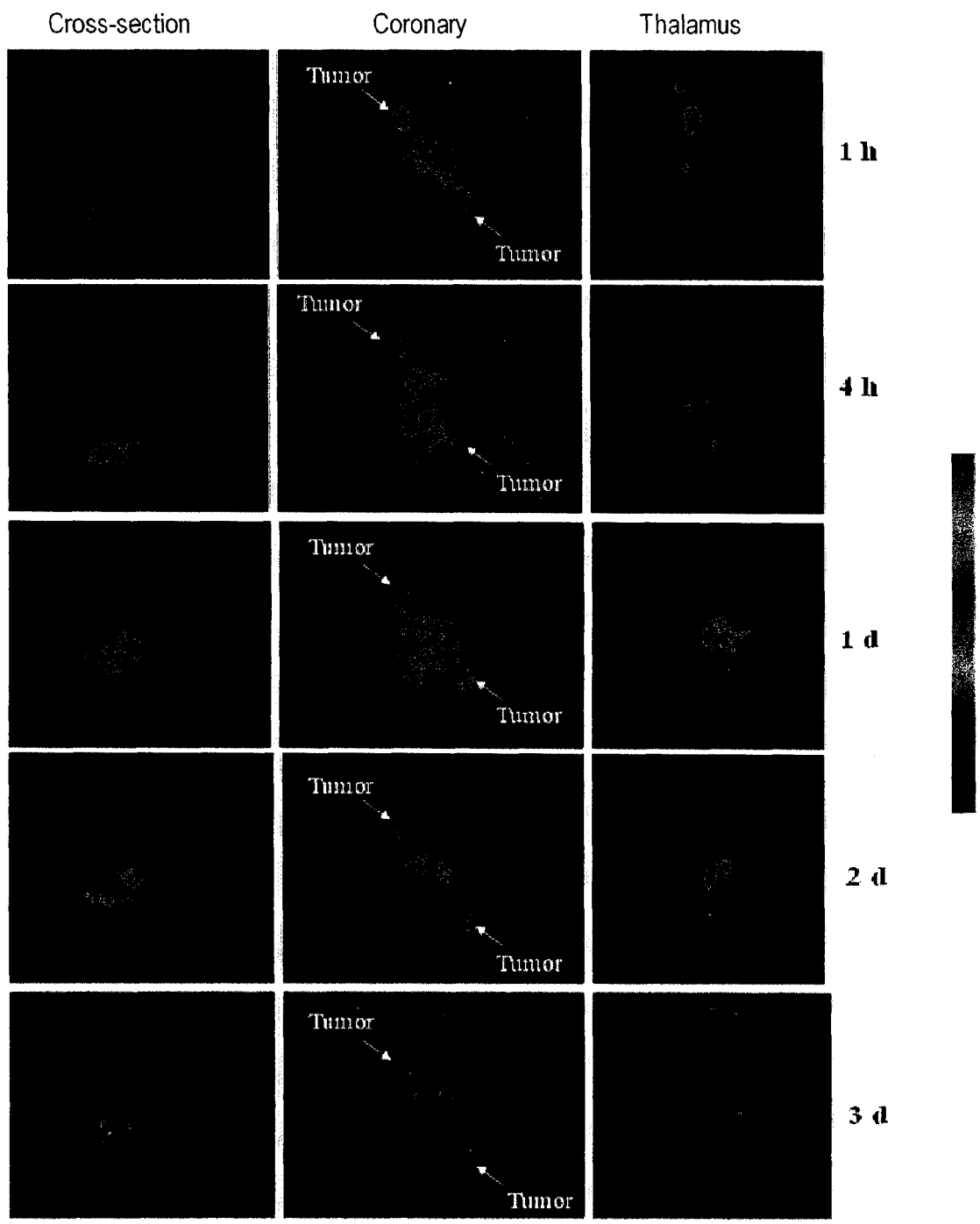
FIG. 19 shows a micro-PET image with the lapse of time after administering $^{64}Cu$-TE2A-c(RGDyK) metal chelating conjugate compound in which TE2A-c(RGDyK) has been labeled with $^{64}Cu$, according to an Example, to a female nude mouse having U87MG tumor cells.

FIG. 18 shows the administration of $^{64}$Cu-TE2A-c(RGDyK) compound (38) to the subject animal, a female nude mouse having U87MG tumor cells. FIG. 19 shows Micro PET images over time (at 1 hour, 4 hours, 1 day, 2 days and 3 days) after administration of $^{64}$Cu-TE2A-c(RGDyK) compound (38).

Example 19

In the present Example, [$^{64}$Cu-TE2A-trastuzumab] metal chelating conjugate compound (40) was prepared via the route shown in Reaction Scheme 14 below, by binding TE2A-NCS compound (14) obtained according to the Example above to an antibody trastuzumab (Herceptin), and chelating $^{64}$Cu metal thereto.

<Reaction Scheme 14>

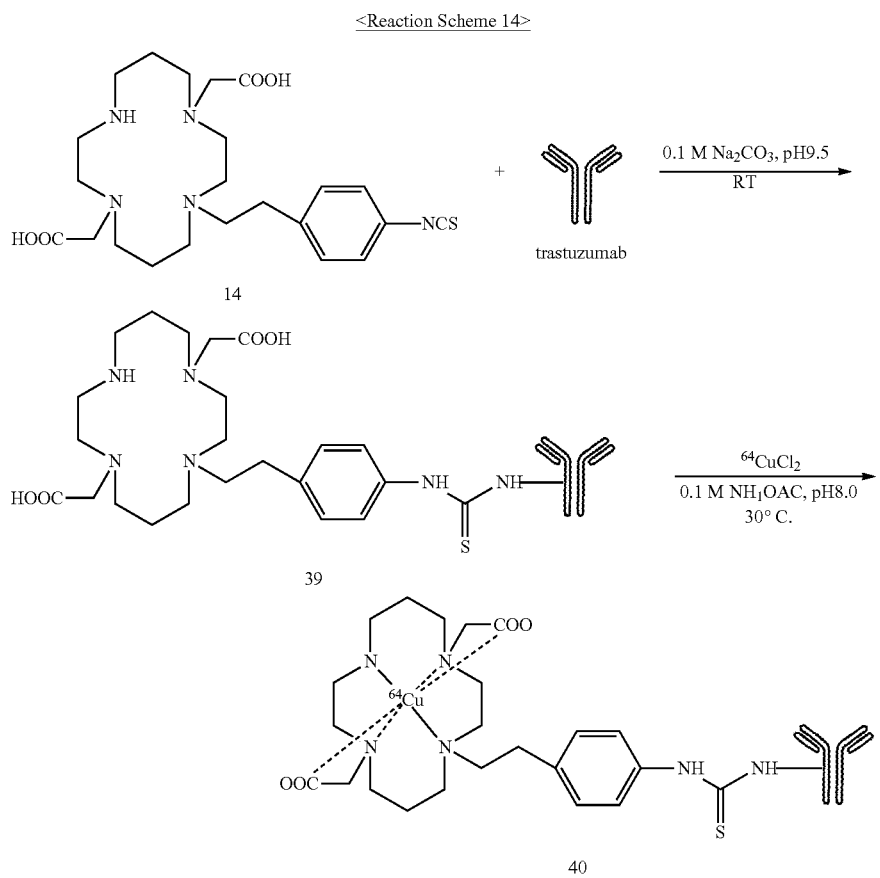

Preparation of [$^{64}$Cu-TE2A-trastuzumab] Metal Chelating Conjugate Compound (40)

Preparation of TE2A-NCS and Antibody Trastuzumab Conjugate Compound (39)

To trastuzumab (2 mg) was added a 50-fold excessive amount of TE2A-NCS compound (14) (0.33 mg) in 0.1 M Na$_2$CO$_3$ (pH 9.5, 100 μl). The solution was gently stirred at an ambient temperature for 24 hours. One day later, the content was transferred to Centricon YM-50, which was centrifuged to decrease the solvent. To the resultant TE2A-trastuzumab was added PBS (pH 7.2, 3×2 ml), and the content was centrifuged to remove the unreacted ligand. To the purified TE2A-trastuzumab compound (39) was added PBS 2.0 ml, and the mixture was maintained at −20° C.

Preparation of [$^{64}$Cu-TE2A-trastuzumab] Metal Chelating Conjugate Compound (40)

To TE2A-trastuzumab compound (39) (50 μg) in 0.1 M NH$_4$OAc buffer (pH 8.0) (100 μl) was added $^{64}$Cu (0.52 mCi) in 0.1 M NH4OAc buffer (pH 8.0). The solution was reacted at 30° C. for 5 minutes. The $^{64}$Cu-labeled TE2A-trastuzumab was purified by centrifugation with Microcon YM-50. The radiochemical purity was identified by size exclusion chromatography (SEC) HPLC (BioSilect SEC 250-5 300×7.8 mm; flow rate 1 ml/min, with the isocratic mobile phase consisting of PBS, pH=7.4) and instant TLC (ITLC-SG, developed by saline).

Figure 20:
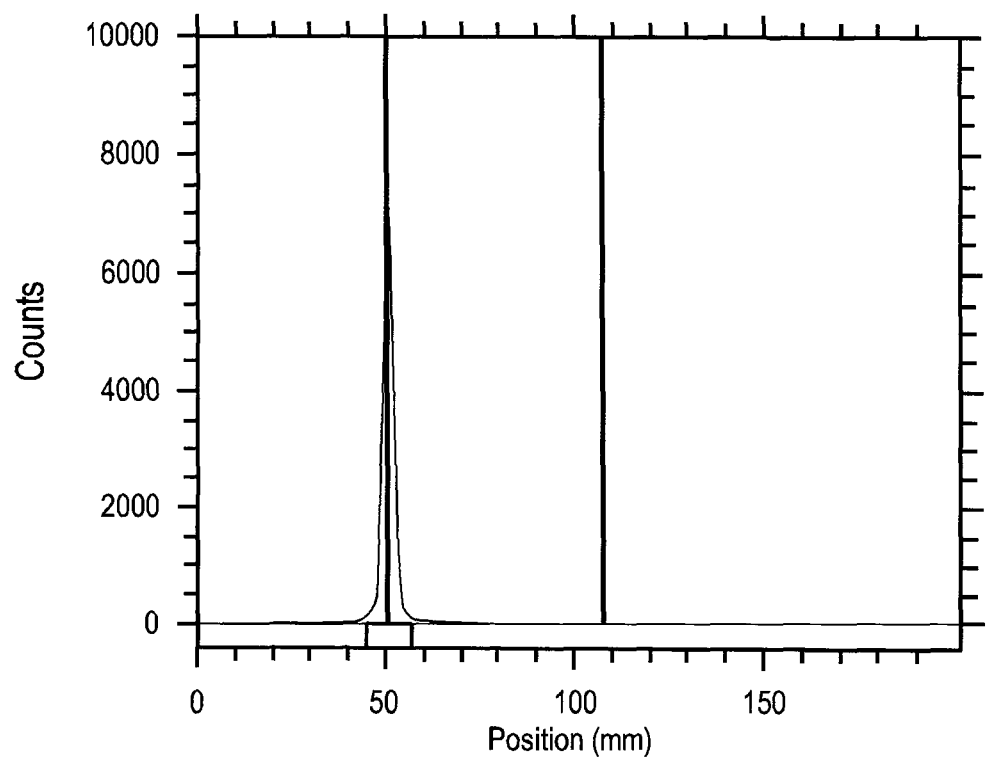
FIG. 20 shows a radio-ITLC chromatogram of $^{64}Cu$-TE2A-trastuzumab metal chelating conjugate compound in which TE2A-trastuzumab has been labeled with $^{64}Cu$, according to an Example.
Figure 21:
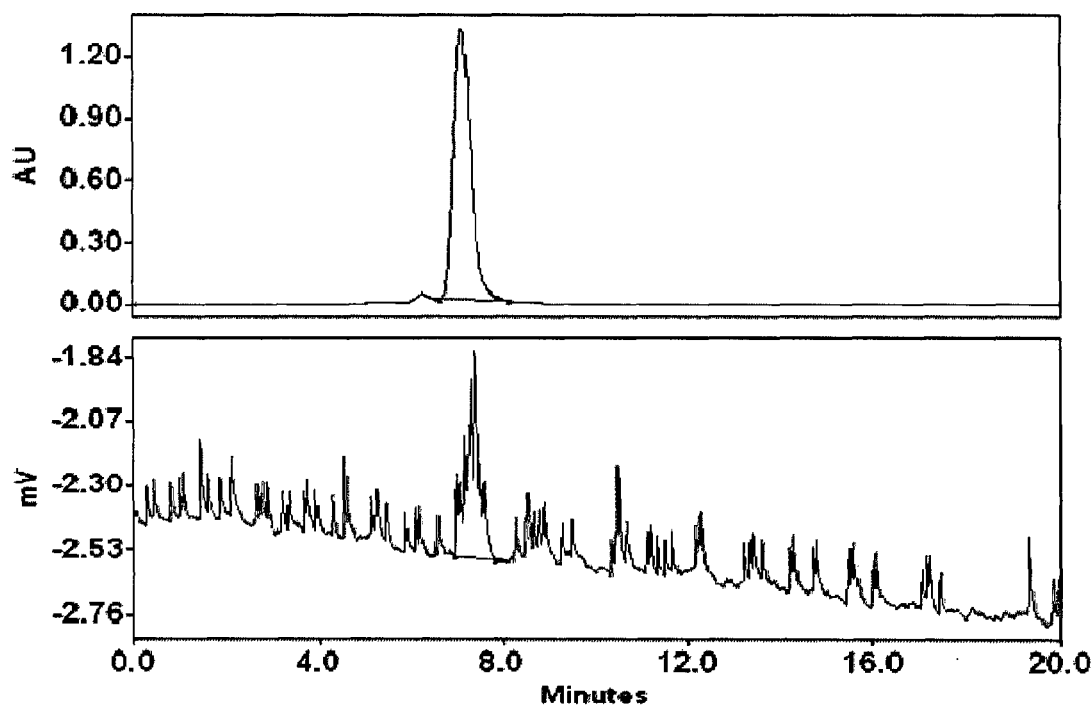
FIG. 21 shows SEC HPLC chromatograms of both TE2A-trastuzumab conjugate compound according to an Example and of $^{64}Cu$-TE2A-trastuzumab metal chelating conjugate compound (in which TE2A-trastuzumab has been labeled with $^{64}Cu$), respectively, in order to confirm the preparation of the metal chelating conjugate compound.

FIG. 20 shows a radio-ITLC chromatogram of $^{64}$Cu-TE2A-trastuzumab compound (40), while FIG. 21 simultaneously shows chromatograms of TE2A-trastuzumab compound (39) and $^{64}$Cu-TE2A-trastuzumab compound (40) on SEC HPLC, in order to confirm the preparation of the metal chelating conjugate compound.

Example 20

Experiment of Distribution In Vivo of $^{64}$Cu-TE2A-Trastuzumab

Figure 22:
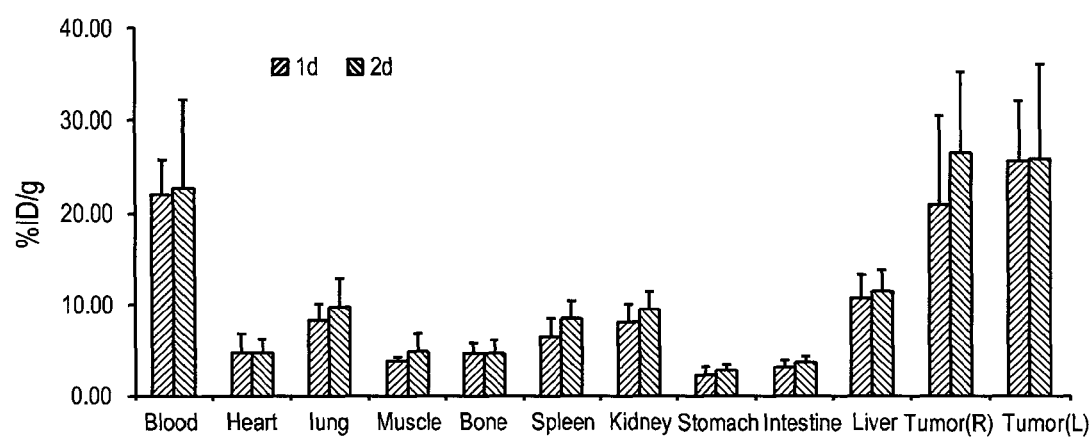
FIG. 22 shows the result of the in vivo distribution test of $^{64}$Cu-TE2A-trastzumab metal chelating conjugate compound in which TE2A-trastuzumab has been labeled with $^{64}$Cu, according to an Example.

Compound $^{64}$Cu-TE2A-trastuzumab (40) (20 μCi) in PBS 120 μl was injected to the tails of female nude mice to which NIH3T6.7 tumor had been transplanted. Two groups were examined at two time points [n=4 per group at 1 day and 2 days post injection (pi)]. The subject animals were sacrificed, and the relevant tissues and organs were collected and weighed. A dosimetric procedure was carried out by using a gamma-counter. The calculations were performed by comparing with a reference value of which the percentage of injected amount per gram was known. The test results (% ID/g±SD, n=4) are shown in Table 4 and FIG. 22.

TABLE 4

| Tissue/organ | Day 1 | Day 2 |
|---|---|---|
| Blood | 21.91 ± 3.74 | 22.56 ± 9.60 |
| Heart | 4.67 ± 2.11 | 4.64 ± 1.47 |
| Lung | 8.28 ± 1.73 | 9.73 ± 3.06 |

TABLE 4-continued

| Tissue/organ | Day 1 | Day 2 |
| --- | --- | --- |
| Muscle | 3.81 ± 0.37 | 4.94 ± 1.84 |
| Bone | 4.53 ± 1.11 | 4.60 ± 1.46 |
| Spleen | 6.51 ± 2.00 | 8.43 ± 1.77 |
| Kidney | 8.15 ± 1.81 | 9.56 ± 1.80 |
| Stomach | 2.18 ± 0.97 | 2.70 ± 0.64 |
| Intestine | 3.16 ± 0.65 | 3.56 ± 0.74 |
| Liver | 10.67 ± 2.54 | 11.50 ± 2.25 |
| Tumor (R) | 20.85 ± 9.57 | 26.34 ± 9.05 |
| Tumor (L) | 25.65 ± 6.54 | 25.86 ± 10.23 |

Example 21

Micro PET Image Analysis of $^{64}$Cu-TE2A-trastuzumab

PET scans and image analyses of the present Example were carried out by using a Micro PET R4 rodent model scanner. The imaging test was carried out with a female nude mouse bearing 31-days NIH3T6.7 tumors. Compound $^{64}$Cu-TE2A-trastuzumab (40) (145 μi) was injected to the tail of the mouse. After 1 hour, 4 hours, 1 day, 2 days, 3 days and 5 days after injection, the mouse was anesthetized with 1-2% isoflurane. The mouse was fixed with its face down, and an image was obtained. The images were reconstituted by an algorithm of 2-dimensional OSEM, without any correction of attenuation or scattering.

Figure 23:
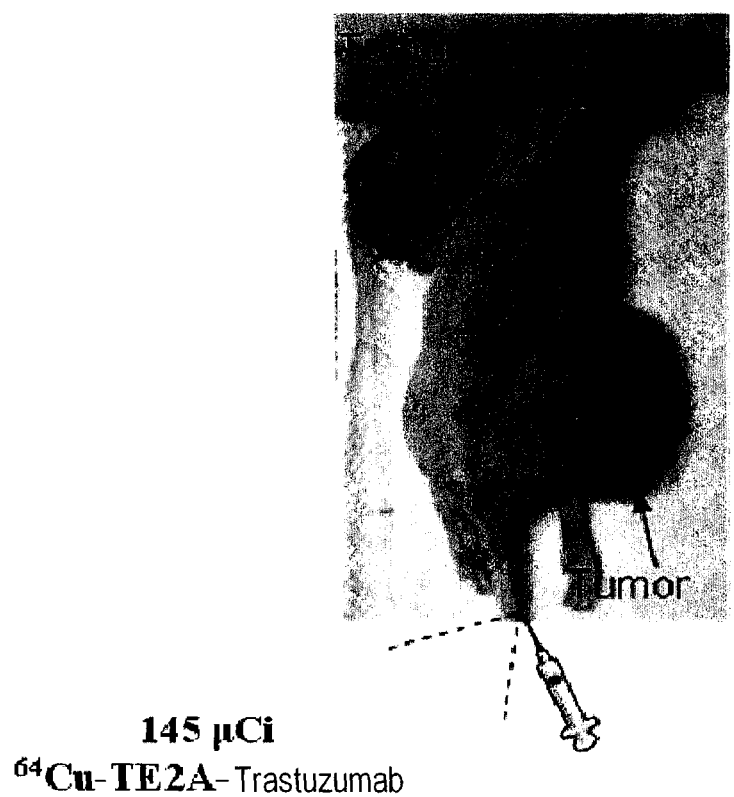
FIG. 23 illustrates administering $^{64}$Cu-TE2A-trastuzumab metal chelating conjugate compound in which TE2A-trastuzumab has been labeled with $^{64}$Cu, according to an Example, to a female nude mouse having NIH3T6.7 tumor cells.
Figure 24:
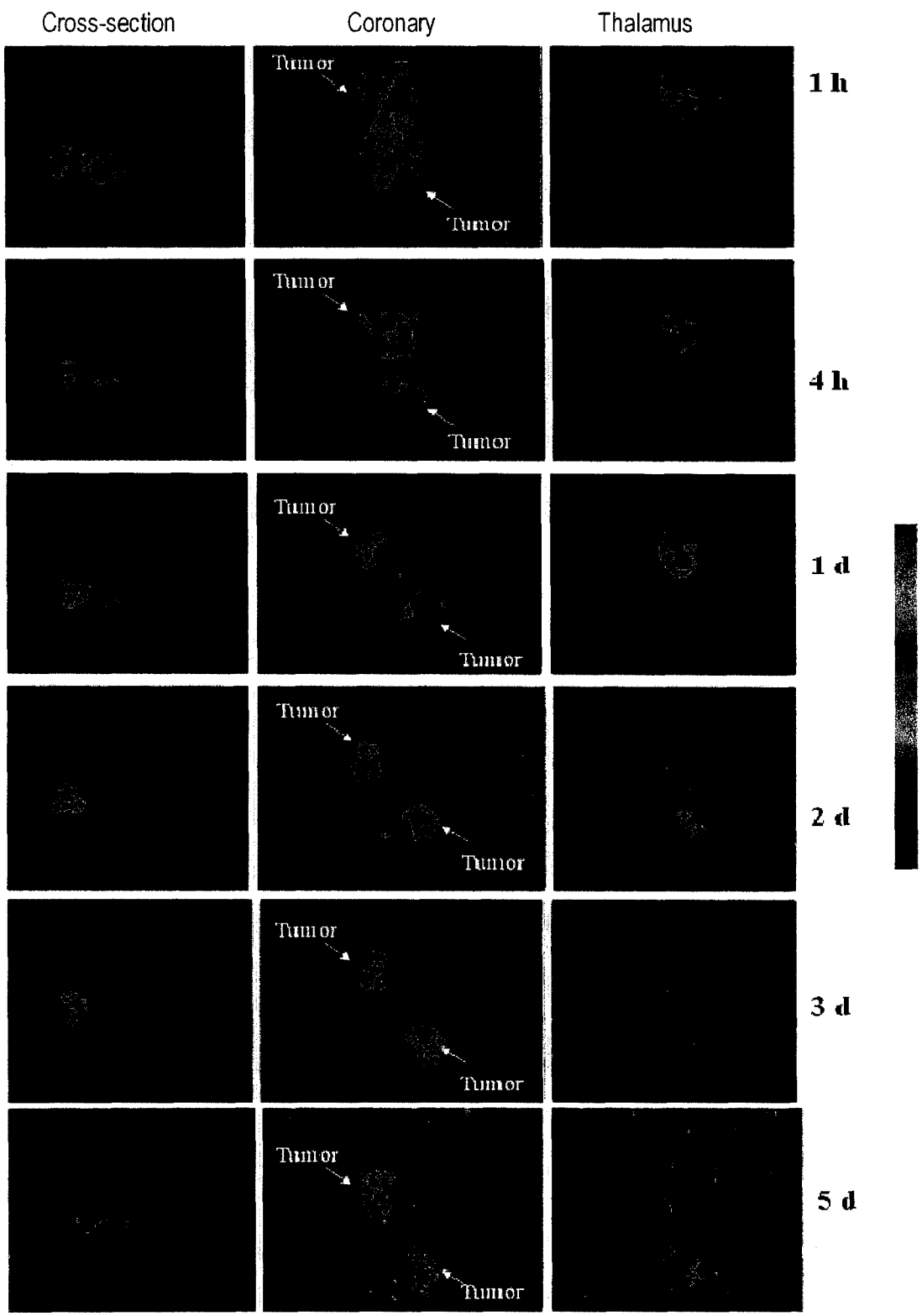
FIG. 24 shows a micro-PET image with the lapse of time after administering $^{64}$Cu-TE2A-trastuzumab metal chelating conjugate compound in which TE2A-trastuzumab has been labeled with $^{64}$Cu, according to an Example, to a female nude mouse having NIH3T6.7 tumor cells.

FIG. 23 shows the administration of $^{64}$Cu-TE2A-trastuzumab compound (40) to the subject animal, a female nude mouse having NIH3T6.7 tumor cells. FIG. 24 shows Micro PET images at 1 hour, 4 hours, 1 day, 2 days, 3 days and 5 days after administration of $^{64}$Cu-TE2A-trastuzumab compound (40).

The various examples described above are not intended to restrict the subject of the present invention, of which authentic scope and purpose are indicated by the claims attached.

What is claimed is:

1. A polyazamacrocyclic compound represented by Chemical Formula 1 or a pharmaceutically acceptable salt thereof:

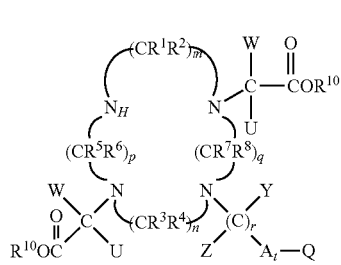

[Chemical Formula 1]

wherein
m, n, p and q are identical to or different from one another, and individually represent an integer of 2 or 3, with the proviso that m, n, p and q are not all two,
r is an integer from 0 to 5,
t is an integer of 0 or 1,
r+t>0,
$R^1$, $R^2$, $R^3$, $R^4$, $R^5$, $R^6$, $R^7$ and $R^8$ are identical to or different from one another, and individually represent H, $C_{1-5}$ alkyl or $C_{3-6}$ cycloalkyl,
$R^{10}$ represents H, $C_{1-5}$ alkyl, $C_{3-6}$ cycloalkyl, or $C_{7-14}$ aralkyl, U and W are identical to or different from one another, and individually represent H, $C_{1-5}$ alkyl or $C_{3-6}$ cycloalkyl,
Y and Z are identical to or different from one another, and individually represent H, $C_{1-5}$ alkyl or $C_{3-6}$ cycloalkyl,
A represents $C_{6-10}$ aryl,
Q represents H, nitro, amino, isothiocyanato, maleimido, alkyne, aminoxy, thiol, or azide.

2. The polyazamacrocyclic compound or pharmaceutically acceptable salt thereof according to claim 1, wherein the pharmaceutically acceptable salt, when the compound represented by Chemical Formula 1 contains a negatively charged component, comprises a cation or a cationic group selected from the group consisting of potassium, sodium, lithium, ammonium, silver, calcium and magnesium, or
when the compound represented by Chemical Formula 1 contains a positively charged component, comprises an anion or an anionic group selected from the group consisting of $F^-$, $Cl^-$, $Br^-$, $I^-$, $ClO_4^-$, $BF_4^-$, $HCO_3^-$, $CH_3CO_2^-$, $CH_3SO_3^-$, $CH_3C_6H_4SO_3^-$, $CF_3SO_3^-$, $H_2PO_4^-$ and $B(C_6H_5)_4^-$.

3. The polyazamacrocyclic compound or pharmaceutically acceptable salt thereof according to claim 1, wherein Q is isothiocyanato.

4. The polyazamacrocyclic compound or pharmaceutically acceptable salt thereof according to claim 1, wherein Q is amino.

5. The polyazamacrocyclic compound or pharmaceutically acceptable salt thereof according to any one of claims 1 to 3, which is
1,8-bis-(carboxymethyl)-4-(4'-isothiocyanatobenzyl)-1,4,8,11-tetraazacyclotetradecane,
1,8-bis-(carboxymethyl)-4-(4'-isothiocyanatophenethyl)-1,4,8,11-tetraazacyclotetradecane,
1,8-bis-(carboxymethyl)-4-(4'-nitrophenethyl)-1,4,8,11-tetraazacyclotetradecane, or
1,8-bis-(carboxymethyl)-4-(methyl)-1,4,8,11-tetraazacyclotetradecane.

6. A method for preparing a polyazamacrocyclic compound represented by Chemical Formula 1, which comprises the steps of
(i) reacting a compound represented by Chemical Formula 9 with α-halocarboxylic ester (X—CUW—CO$_2$R$^9$) to obtain a trans-N,N'-disubstituted compound represented by Chemical Formula 10,
(ii) reacting a compound represented by Chemical Formula 10 with a base to obtain a compound represented by Chemical Formula 11,
(iii) introducing a functional group —(CYZ)$_r$-A$_t$-Q to a secondary amine group in the cycle of compound represented by Chemical Formula 11 to form a compound represented by Chemical Formula 1:

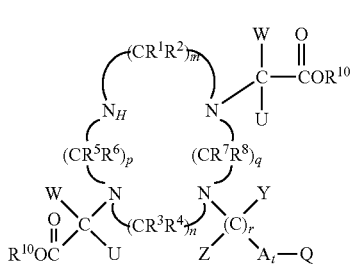

[Chemical Formula 1]

-continued

[Chemical Formula 9]

[Chemical Formula 10]

[Chemical Formula 11]

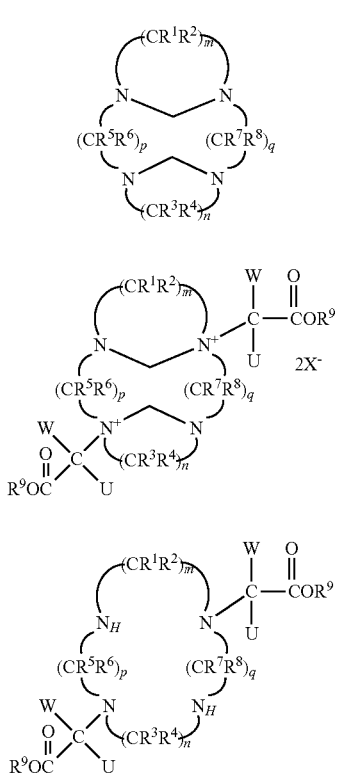

wherein m, n, p and q are identical to or different from one another, and independently represent an integer of 2 or 3, with the proviso that m, n, p and q are not all two, r represents an integer from 0 to 5, t represents an integer of 0 or 1, r+t>0, $R^1, R^2, R^3, R^4, R^5, R^6, R^7, R^8$ are identical to or different from one another, and independently represent H, $C_{1-5}$ alkyl or $C_{3-6}$ cycloalkyl, $R^9$ represents $C_{1-5}$ alkyl, $C_{3-6}$ cycloalkyl, or $C_{7-14}$ aralkyl, $R^{10}$ represents H, $C_{1-5}$ alkyl, $C_{3-6}$ cycloalkyl, or $C_{7-14}$ aralkyl, U and W are identical to or different from one another, and individually represent H, $C_{1-5}$ alkyl or $C_{3-6}$ cycloalkyl, X represents F, Cl, Br or I, Y and Z are identical to or different from one another, and individually represent H, $C_{1-5}$ alkyl or $C_{3-6}$ cycloalkyl, A represents $C_{6-10}$ aryl, and Q represents H, nitro, amino, isothiocyanato, maleimido, alkyne, aminoxy, thiol, or azide.

7. The method according to claim 6 for preparing a polyazamacrocyclic compound of Chemical Formula 1 wherein the α-halocarboxylic ester is tert-butylbromoacetate or benzyl bromoacetate.

* * * * *